(12) United States Patent
Merla et al.

(10) Patent No.: US 7,589,113 B2
(45) Date of Patent: Sep. 15, 2009

(54) SUBSTITUTED OXADIAZOLE COMPOUNDS AND THEIR USE AS OPIOID RECEPTOR LIGANDS

(75) Inventors: Beatrix Merla, Aachen (DE); Stefan Oberboersch, Aachen (DE); Bernd Sundermann, Aachen (DE); Werner Englberger, Stolberg (DE); Hagen-Heinrich Hennies, Simmerath (DE); Heinz Graubaum, Erkner (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 12/143,550

(22) Filed: Jun. 20, 2008

(65) Prior Publication Data

US 2009/0005427 A1    Jan. 1, 2009

Related U.S. Application Data

(63) Continuation of application No. PCT/EP2006/012225, filed on Dec. 19, 2006.

(30) Foreign Application Priority Data

Dec. 22, 2005    (DE) .................. 10 2005 061 427

(51) Int. Cl.
*A61K 31/4245*    (2006.01)
*A61P 25/00*    (2006.01)
*C07D 271/06*    (2006.01)
*C07D 417/02*    (2006.01)

(52) U.S. Cl. ...................... 514/364; 548/131
(58) Field of Classification Search .................. None
See application file for complete search history.

(56) References Cited

FOREIGN PATENT DOCUMENTS

WO    WO 01/49654 A2    7/2001

OTHER PUBLICATIONS

International Search Report dated Mar. 29, 2007 with English translation.

*Primary Examiner*—Kamal A Saeed
(74) *Attorney, Agent, or Firm*—Crowell & Moring LLP

(57) ABSTRACT

Substituted oxadiazole compounds corresponding to formula I:

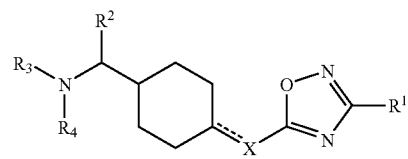

in which X denotes CH, $CH_2$, CH=CH, $CH_2CH_2$, $CH_2CH$=CH or $CH_2CH_2CH_2$; $R^1$ denotes aryl or heteroaryl, in each case unsubstituted or mono- or polysubstituted; or a $C_{1-3}$ alkyl group-linked aryl or heteroaryl group, in each case unsubstituted or mono- or polysubstituted; $R^2$ denotes aryl or heteroaryl, in each case unsubstituted or mono- or polysubstituted; a $C_{1-3}$ alkyl chain-attached aryl group, in each case unsubstituted or mono- or polysubstituted; and $R^3$ and $R^4$ independently denote H; $C_{1-6}$ alkyl, in each case saturated or unsaturated, branched or unbranched, wherein $R^3$ and $R^4$ do not simultaneously mean H; or $R^3$ and $R^4$ together denote $CH_2CH_2OCH_2CH_2$, or $(CH_2)_{3-6}$. The compounds have an affinity for the μ-opioid receptor and may take the form of the racemate; enantiomers, diastereomers, mixtures of enantiomers or diastereomers, an individual enantiomer or diastereomer, a free base, or a salt with a physiologically acceptable acid.

17 Claims, No Drawings

SUBSTITUTED OXADIAZOLE COMPOUNDS AND THEIR USE AS OPIOID RECEPTOR LIGANDS

CROSS REFERENCE TO RELATED APPLICATIONS

This application is a continuation of international patent application no. PCT/EP2006/012225, filed Dec. 19, 2006, designating the United States of America, and published in German on Jul. 19, 2007 as WO 2007/079931, the entire disclosure of which is incorporated herein by reference. Priority is claimed based on Federal Republic of Germany patent application no. DE 10 2005 061 427.2, filed Dec. 22, 2005.

BACKGROUND OF THE INVENTION

The present invention relates to substituted oxadiazole derivatives, to methods for the production thereof, to medicaments containing these compounds and to the use of substituted oxadiazole derivatives for producing medicaments.

The treatment of chronic and non-chronic pain is of great significance in medicine. There is a worldwide need for highly effective pain treatments. The urgency of the requirement for effective therapeutic methods for providing tailored and targeted treatment of chronic and non-chronic pain, this being taken to mean pain treatment which is effective and satisfactory from the patient's standpoint, is evident from the large number of scientific papers relating to applied analgesia and to basic nociception research which have appeared in recent times.

Conventional opioids such as morphine are highly effective in treating severe to extreme pain. However, the use thereof is limited by known side-effects, for example respiratory depression, vomiting, sedation, constipation and development of tolerance. Moreover, they are less effective in treating neuropathic or incidental pain, which is in particular experienced by tumour patients.

J. Med. Chem. 1993, 36, 1529-1538 discloses 5-HT$_{1D}$ agonists which exhibit an action against migraine. These compounds are substituted with an indolyl residue on the oxadiazole ring and do not bear a cyclohexylaminomethyl residue.

SUMMARY OF THE INVENTION

One object underlying the invention was to provide novel analgesically active substances which are suitable for treating pain, in particular including chronic and neuropathic pain.

The present invention therefore provides substituted oxadiazole derivatives of the general formula I,

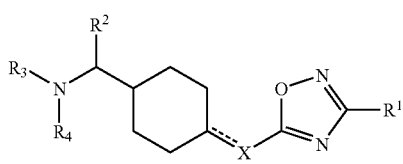

I in which
X means CH, CH$_2$, CH=CH, CH$_2$CH$_2$, CH$_2$CH=CH or CH$_2$CH$_2$CH$_2$
R$^1$ means aryl, heteroaryl, in each case unsubstituted or mono- or polysubstituted; a C$_{1-3}$ alkyl group-linked aryl or heteroaryl residue, in each case unsubstituted or mono- or polysubstituted;
R$^2$ means aryl or heteroaryl, in each case unsubstituted or mono- or polysubstituted; a C$_{1-3}$ alkyl chain-attached aryl residue, in each case unsubstituted or mono- or polysubstituted;
R$^3$ and R$^4$ mutually independently mean H; —C$_{1-6}$ alkyl, in each case saturated or unsaturated, branched or unbranched, wherein R$^3$ and R$^4$ do not simultaneously mean H, or
R$^3$ and R$^4$ together mean CH$_2$CH$_2$OCH$_2$CH$_2$, or (CH$_2$)$_{3-6}$, in the form of the racemate; the enantiomers, diastereomers, mixtures of the enantiomers or diastereomers or of an individual enantiomer or diastereomer; the bases and/or salts of physiologically acceptable acids. The compounds exhibit an affinity for the µ opioid receptor.

The expressions "C$_{1-3}$ alkyl" and "C$_{1-6}$ alkyl" comprise for the purposes of the present invention acyclic saturated or unsaturated hydrocarbon residues, which may be branched or straight-chain and unsubstituted or mono- or polysubstituted, with 1 to 3 C atoms or 1-6 C atoms, i.e. C$_{1-3}$ alkanyls, C$_{2-3}$ alkenyls and C$_{2-3}$ alkynyls or C$_{1-6}$ alkanyls, C$_{2-6}$ alkenyls and C$_{2-6}$ alkynyls. Alkenyls here comprise at least one C—C double bond and alkynyls at least one C—C triple bond. Alkyl is advantageously selected from the group comprising methyl, ethyl, n-propyl, 2-propyl, n-butyl, isobutyl, sec.-butyl, tert.-butyl, n-pentyl, iso-pentyl, neopentyl, n-hexyl, 2-hexyl, ethylenyl (vinyl), ethynyl, propenyl (—CH$_2$CH=CH$_2$, —CH=CH—CH$_3$, —C(=CH$_2$)—CH$_3$), propynyl (—CH—C≡CH, —C≡C—CH$_3$), butenyl, butynyl, pentenyl, pentynyl, hexenyl and hexynyl. Methyl and tert.-butyl are particularly advantageous.

For the purposes of the present invention, the term "aryl" means aromatic hydrocarbons, inter alia phenyls and naphthyls. The aryl residues may also be fused with further saturated, (partially) unsaturated or aromatic ring systems. Each aryl residue may be present in unsubstituted or mono- or polysubstituted form, wherein the aryl substituents may be identical or different and be in any desired and possible position of the aryl. Aryl is advantageously selected from the group which contains phenyl, 1-naphthyl, 2-naphthyl, which may in each case be unsubstituted or mono- or polysubstituted. The phenyl residue is particularly advantageous.

The term "heteroaryl" denotes a 5-, 6- or 7-membered cyclic aromatic residue, which contains at least 1, optionally also 2, 3, 4 or 5 heteroatoms, wherein the heteroatoms are identical or different and the heterocycle may be unsubstituted or mono- or polysubstituted; in the event of substitution on the heterocycle, the substituents may be identical or different and be in any desired and possible position of the heteroaryl. The heterocycle may also be part of a bi- or polycyclic system. Preferred heteroatoms are nitrogen, oxygen and sulfur. It is preferred for the heteroaryl residue to be selected from the group which contains pyrrolyl, indolyl, furyl (furanyl), benzofuranyl, thienyl (thiophenyl), benzothienyl, benzothiadiazolyl, benzothiazolyl, benzotriazolyl, benzodioxolanyl, benzodioxanyl, phthalazinyl, pyrazolyl, imidazolyl, thiazolyl, oxadiazolyl, isoxazolyl, pyridyl, pyridazinyl, pyrimidinyl, pyrazinyl, pyranyl, indazolyl, purinyl, indolizinyl, quinolinyl, isoquinolinyl, quinazolinyl, carbazolyl, phenazinyl, phenothiazinyl or oxadiazolyl, wherein attachment to the compounds of the general structure I may be made via any desired and possible ring member of the heteroaryl residue. Pyridyl, pyrrolyl and thienyl are particularly preferred.

For the purposes of the present invention, the expression "C$_{1-3}$ alkyl-attached aryl or heteroaryl" means that C$_{1-3}$ alkyl and aryl or heteroaryl have the above-defined meanings and the aryl or heteroaryl residue is attached to the compound of the general structure I via a $C_{1-3}$ alkyl group. Benzyl and phenethyl are particularly advantageous for the purposes of the present invention.

In connection with "alkyl", the term "substituted" is taken for the purposes of the present invention to mean the substitution of a hydrogen residue by F, Cl, Br, I, —CN, $NH_2$, NH—$C_{1-6}$-alkyl, NH—$C_{1-6}$-alkyl-OH, —$C_{1-6}$ alkyl, N($C_{1-6}$-alkyl)$_2$, N($C_{1-6}$-alkyl-OH)$_2$, —$NO_2$, SH, S—$C_{1-6}$-alkyl, S-benzyl, —O—$C_{1-6}$-alkyl, OH, O—$C_{1-6}$-alkyl-OH, =O, O-benzyl, C(=O)—$C_{1-6}$-alkyl, $CO_2H$, $CO_2$—$C_{1-6}$-alkyl, or benzyl, wherein polysubstituted residues are taken to mean such residues which are polysubstituted, for example di- or trisubstituted, on either different or the same atoms, for example trisubstituted on the same C atom, as in the case of $CF_3$, or —$CH_2$—$CF_3$, or at different locations as in the case of —CH(OH)—CH=CH—$CHCl_2$. Polysubstitution may proceed with identical or different substituents.

With regard to "aryl" and "heteroaryl", "mono- or polysubstituted" is taken for the purposes of the present invention to mean mono- or polysubstitution, for example di-, tri- or tetrasubstitution of one or more hydrogen atoms of the ring system by F, Cl, Br, I, CN, $NH_2$, NH—$C_{1-6}$-alkyl, NH—$C_{1-6}$-alkyl-OH, N($C_{1-6}$-alkyl)$_2$, N($C_{1-6}$-alkyl-OH)$_2$, $NO_2$, SH, —S—$C_{1-6}$-alkyl, OH, O—$C_{1-6}$-alkyl, O—$C_{1-6}$-alkyl-OH, C(=O)—$C_{1-6}$-alkyl, $CO_2H$, $CO_2$—$C_{1-6}$-alkyl, $CF_3$, $C_{1-6}$ alkyl; on one or optionally different atoms (wherein a substituent may optionally itself in turn be substituted). Polysubstitution here proceeds with identical or different substituents. For "aryl" and "heteroaryl", preferred substituents are here —F, —Cl, —$CF_3$, —O—$CH_3$, methyl, O—$CF_3$, and tert.-butyl.

A salt formed with a physiologically acceptable acid is taken for the purposes of the present invention to means salts of the particular active ingredient with inorganic or organic acids which are the physiologically acceptable, in particular for use in humans and/or mammals. The hydrochloride is particularly preferred. Examples of physiologically acceptable acids are: hydrochloric acid, hydrobromic acid, sulfuric acid, methanesulfonic acid, formic acid, acetic acid, oxalic acid, succinic acid, tartaric acid, mandelic acid, fumaric acid, lactic acid, citric acid, glutamic acid, 1,1-dioxo-1,2-dihydro-$1\lambda^6$-benzo[d]isothiazol-3-one (saccharinic acid), monomethylsebacic acid, 5-oxoproline, hexane-1-sulfonic acid, nicotinic acid, 2-, 3- or 4-aminobenzoic acid, 2,4,6-trimethylbenzoic acid, α-lipoic acid, acetylglycine, hippuric acid, phosphoric acid and/or aspartic acid. Hydrochloric acid is particularly preferred.

The term $(CH_2)_{3-6}$ or $(CH_2)_{4-5}$ should be taken to mean —$CH_2$—$CH_2$—$CH_2$—, —$CH_2$—$CH_2$—$CH_2$—$CH_2$—, —$CH_2$—$CH_2$—$CH_2$—$CH_2$—$CH_2$— and —$CH_2$—$CH_2$—$CH_2$—$CH_2$—$CH_2$—$CH_2$— or —$CH_2$—$CH_2$—$CH_2$—$CH_2$—, —$CH_2$—$CH_2$—$CH_2$—$CH_2$—$CH_2$—.

Oxadiazole derivatives which are preferred for the purposes of the present invention are those in which X means CH, $CH_2$, CH=CH or $CH_2CH_2$.

Substituted oxadiazole derivatives which are preferred for the purposes of the present invention are those in which $R^1$ means phenyl, naphthyl, pyrrolyl, indolyl, furyl, benzofuranyl, thienyl, benzothienyl, benzothiadiazolyl, benzothiazolyl, benzotriazolyl, benzodioxolanyl, benzodioxanyl, phthalazinyl, pyrazolyl, imidazolyl, thiazolyl, oxadiazolyl, isoxazolyl, pyridyl, pyridazinyl, pyrimidinyl, pyrazinyl, pyranyl, indazolyl, purinyl, indolizinyl, quinolinyl, isoquinolinyl, quinazolinyl, carbazolyl, phenazinyl, phenothiazinyl or oxadiazolyl, in each case unsubstituted or mono- or polysubstituted with F, Cl, Br, I, CN, $NH_2$, NH—$C_{1-6}$-alkyl, NH—$C_{1-6}$-alkyl-OH, N($C_{1-6}$alkyl)$_2$, N($C_{1-6}$-alkyl-OH)$_2$, $NO_2$, SH, S—$C_{1-6}$-alkyl, OH, O—$C_{1-6}$ -alkyl, O—$C_{1-6}$-alkyl-OH, C(=O)—$C_{1-6}$-alkyl, $CO_2H$, $CO_2$—$C_{1-6}$-alkyl, $CF_3$, $OCF_3$, $C_{1-6}$ alkyl; $C_{1-3}$ alkyl group-linked phenyl, naphthyl, pyrrolyl, indolyl, furyl, benzofuranyl, thienyl, benzothienyl, benzothiadiazolyl, benzothiazolyl, benzotriazolyl, benzodioxolanyl, benzodioxanyl, phthalazinyl, pyrazolyl, imidazolyl, thiazolyl, oxadiazolyl, isoxazolyl, pyridyl, pyridazinyl, pyrimidinyl, pyrazinyl, pyranyl, indazolyl, purinyl, indolizinyl, quinolinyl, isoquinolinyl, quinazolinyl, carbazolyl, phenazinyl, phenothiazinyl or oxadiazolyl, in each case unsubstituted or mono- or polysubstituted with F, Cl, Br, I, CN, $OCF_3$, $NH_2$, NH—$C_{1-6}$-alkyl, NH—$C_{1-6}$-alkyl-OH, N($C_{1-6}$ alkyl)$_2$, N($C_{1-6}$-alkyl-OH)$_2$, $NO_2$, SH, S—$C_{1-6}$-alkyl, OH, O—$C_{1-6}$-alkyl, O—$C_{1-6}$-alkyl-OH, C(=O)—$C_{1-6}$-alkyl, $CO_2H$, $CO_2$—$C_{1-6}$-alkyl, $CF_3$, $C_{1-6}$ alkyl;

in particular, $R^1$ means phenyl, naphthyl, thienyl, pyridyl or pyrrolyl, benzyl, methylindolyl, methylthienyl or phenethyl, unsubstituted or mono- or polysubstituted with F, Cl, Br, CN, $OCF_3$, $NH_2$, $NO_2$, SH, S—$C_{1-6}$-alkyl, OH, O—$C_{1-6}$-alkyl, $CO_2H$, $CO_2$—$C_{1-6}$-alkyl, $CF_3$ or $C_{1-6}$ alkyl.

Substituted oxadiazole derivatives which are particularly preferred are those in which $R^1$ means phenyl, thienyl, benzyl, methylindolyl, methylthienyl or pyrrolyl, unsubstituted or mono- or polysubstituted with Cl, Br, $OCH_3$, $CH_3$, F, $OCF_3$, $CF_3$ or tert.-butyl.

Substituted oxadiazole derivatives which are preferred for the purposes of the present invention are also those in which $R^2$ means phenyl, thienyl or pyridyl, in each case unsubstituted or mono- or polysubstituted with F, Cl, CN, NH—$C_{1-6}$ -alkyl, NH—$C_{1-6}$-alkyl-OH, N($C_{1-6}$alkyl)$_2$, N($C_{1-6}$-alkyl-OH)$_2$, $NO_2$, SH, S—$C_{1-6}$-alkyl, OH, O—$C_{1-6}$ -alkyl, O—$C_{1-6}$-alkyl-OH, C(=O)—$C_{1-6}$-alkyl, $CO_2H$, $CO_2$—$C_{1-6}$-alkyl, $CF_3$, $C_{1-6}$-alkyl; a $C_{1-3}$ alkyl chain-attached aryl residue, in each case unsubstituted or mono- or polysubstituted with F, Cl, CN, NH—$C_{1-6}$-alkyl, NH—$C_{1-6}$-alkyl-OH, N($C_{1-6}$alkyl)$_2$, N($C_{1-6}$-alkyl-OH)$_2$, $NO_2$, SH, S—$C_{1-6}$-alkyl, OH, O—$C_{1-6}$-alkyl, O—$C_{1-6}$-alkyl-OH, C(=O)—$C_{1-6}$-alkyl, $CO_2H$, $CO_2$—$C_{1-6}$-alkyl, $CF_3$, —$C_{1-6}$-alkyl;

preferably $R^2$ means phenyl or thienyl, in each case unsubstituted or mono- or polysubstituted with F, Cl, CN, $NO_2$, SH, S—$C_{1-6}$-alkyl, OH, O—$C_{1-6}$-alkyl, $CO_2H$, $CO_2$—$C_{1-6}$-alkyl, $CF_3$, $C_{1-6}$ alkyl; a $C_{1-3}$ alkyl chain-attached phenyl residue, in each case unsubstituted or mono- or polysubstituted with F, Cl, CN, $NO_2$, SH, S—$C_{1-6}$-alkyl, OH, O—$C_{1-6}$-alkyl, $CO_2H$, $CO_2$—$C_{1-6}$-alkyl, $CF_3$, $C_{1-6}$-alkyl;

in particular $R^2$ means phenyl, unsubstituted or mono- or polysubstituted with F, Cl, OH, $OCH_3$, $CF_3$, or $CH_3$; thienyl; or a $C_{1-3}$ alkyl chain-attached phenyl residue, unsubstituted or mono- or polysubstituted with F, Cl, CN, OH, $OCH_3$, $CF_3$ or $CH_3$.

Particularly preferred oxadiazole derivatives are those in which $R^2$ means phenyl, unsubstituted or monosubstituted with Cl or F, phenethyl or thienyl.

Oxadiazole derivatives which are preferred for the purposes of the present invention are moreover those in which $R^3$ and $R^4$ mutually independently mean H or $C_{1-6}$ alkyl, wherein $R^3$ and $R^4$ do not simultaneously mean H, or $R^3$ and $R^4$ together mean $CH_2CH_2OCH_2CH_2$, or $(CH_2)_{4-5}$. Particularly preferred oxadiazole derivatives are those in which $R^3$ and $R^4$ mean $CH_3$.

It is preferred for X to mean CH, $CH_2$, CH=CH or $CH_2CH_2$.

Very particularly preferred substituted oxadiazole derivatives are those selected from the group consisting of:

43. (4-((3-(4-chlorobenzyl)-1,2,4-oxadiazol-5-yl)methyl)cyclohexyl)-N,N-dimethyl(phenyl)methanamine
44. (4-((3-(4-methoxybenzyl)-1,2,4-oxadiazol-5-yl)methyl)cyclohexyl)-N,N-dimethyl(phenyl)methanamine
45. ((4-chlorophenyl)-{4-[3-(4-chlorophenyl)-[1,2,4]oxadiazol-5-ylmethylene]-cyclohexyl}-methyl)-dimethylamine
46. [{4-[3-(4-chlorophenyl)-[1,2,4]oxadiazol-5-ylmethylene]-cyclohexyl}-(4-fluorophenyl)-methyl]-dimethylamine (more highly polar diastereomer)
47. [{4-[3-(4-chlorophenyl)-[1,2,4]oxadiazol-5-ylmethylene]-cyclohexyl}-(4-fluorophenyl)-methyl]-dimethylamine (more highly nonpolar diastereomer)
48. ({4-[3-(2,3-dichlorophenyl)-[1,2,4]oxadiazol-5-ylmethylene]-cyclohexyl}-phenylmethyl)-dimethylamine (more highly polar diastereomer)
49. ({4-[3-(2,3-dichlorophenyl)-[1,2,4]oxadiazol-5-ylmethylene]-cyclohexyl}-phenylmethyl)-dimethylamine (more highly nonpolar diastereomer)
50. [{4-[3-(2,3-dichlorophenyl)-[1,2,4]oxadiazol-5-ylmethylene]-cyclohexyl}-(3-fluorophenyl)-methyl]-dimethylamine (more highly polar diastereomer)
51. [{4-[3-(2,3-dichlorophenyl)-[1,2,4]oxadiazol-5-ylmethylene]-cyclohexyl}-(3-fluorophenyl)-methyl]-dimethylamine (more highly nonpolar diastereomer)
52. ((4-chlorophenyl)-{4-[3-(2,3-dichlorophenyl)-[1,2,4]oxadiazol-5-ylmethylene]-cyclohexyl}-methyl)-dimethylamine (more highly polar diastereomer)
53. ((4-chlorophenyl)-{4-[3-(2,3-dichlorophenyl)-[1,2,4]oxadiazol-5-ylmethylene]-cyclohexyl}-methyl)-dimethylamine (more highly nonpolar diastereomer)
54. (1-{4-[3-(2,3-dichlorophenyl)-[1,2,4]oxadiazol-5-ylmethylene]-cyclohexyl}-3-phenylpropyl)-dimethylamine
55. [{4-[3-(2,3-dichlorophenyl)-[1,2,4]oxadiazol-5-ylmethylene]-cyclohexyl}-(4-fluorophenyl)-methyl]-dimethylamine (more highly polar diastereomer)
56. [{4-[3-(2,3-dichlorophenyl)-[1,2,4]oxadiazol-5-ylmethylene]-cyclohexyl}-(4-fluorophenyl)-methyl]-dimethylamine (more highly nonpolar diastereomer)
57. dimethyl-(phenyl-{4-[3-(4-trifluoromethoxyphenyl)-[1,2,4]oxadiazol-5-ylmethylene]-cyclohexyl}-methyl)-amine (more highly polar diastereomer)
58. dimethyl-(phenyl-{4-[3-(4-trifluoromethoxyphenyl)-[1,2,4]oxadiazol-5-ylmethylene]-cyclohexyl}-methyl)-amine (more highly nonpolar diastereomer)
59. ((3-fluorophenyl)-{4-[3-(4-trifluoromethoxyphenyl)-[1,2,4]oxadiazol-5-ylmethylene]-cyclohexyl}-methyl)-dimethylamine (more highly polar diastereomer)
60. ((3-fluorophenyl)-{4-[3-(4-trifluoromethoxyphenyl)-[1,2,4]oxadiazol-5-ylmethylene]-cyclohexyl}-methyl)-dimethylamine (more highly nonpolar diastereomer)
61. ((4-chlorophenyl)-{4-[3-(4-trifluoromethoxyphenyl)-[1,2,4]oxadiazol-5-ylmethylene]-cyclohexyl}-methyl)-dimethylamine (more highly polar diastereomer)
62. ((4-chlorophenyl)-{4-[3-(4-trifluoromethoxyphenyl)-[1,2,4]oxadiazol-5-ylmethylene]-cyclohexyl}-methyl)-dimethylamine (more highly nonpolar diastereomer)
63. dimethyl-(3-phenyl-1-{4-[3-(4-trifluoromethoxyphenyl)-[1,2,4]oxadiazol-5-ylmethylene]-cyclohexyl}-propyl)-amine (more highly polar diastereomer)
64. dimethyl-(3-phenyl-1-{4-[3-(4-trifluoromethoxyphenyl)-[1,2,4]oxadiazol-5-ylmethylene]-cyclohexyl}-propyl)-amine (more highly nonpolar diastereomer)
65. ((4-fluorophenyl)-{4-[3-(4-trifluoromethoxyphenyl)-[1,2,4]oxadiazol-5-ylmethylene]-cyclohexyl}-methyl)-dimethylamine (more highly polar diastereomer)
66. ((4-fluorophenyl)-{4-[3-(4-trifluoromethoxyphenyl)-[1,2,4]oxadiazol-5-ylmethylene]-cyclohexyl}-methyl)-dimethylamine (more highly nonpolar diastereomer)
67. dimethyl-(thiophen-2-yl-{4-[3-(4-trifluoromethoxyphenyl)-[1,2,4]oxadiazol-5-ylmethylene]-cyclohexyl}-methyl)-amine (more highly polar diastereomer)
68. dimethyl-(thiophen-2-yl-{4-[3-(4-trifluoromethoxyphenyl)-[1,2,4]oxadiazol-5-ylmethylene]-cyclohexyl}-methyl)-amine (more highly nonpolar diastereomer)
69. dimethyl-{phenyl-[4-(3-phenyl-[1,2,4]oxadiazol-5-ylmethylene)-cyclohexyl]-methyl}-amine (more highly polar diastereomer)
70. dimethyl-{phenyl-[4-(3-phenyl-[1,2,4]oxadiazol-5-ylmethylene)-cyclohexyl]-methyl}-amine (more highly nonpolar diastereomer)
71. {(3-fluorophenyl)-[4-(3-phenyl-[1,2,4]oxadiazol-5-ylmethylene)-cyclohexyl]-methyl}-dimethylamine (more highly polar diastereomer)
72. {(3-fluorophenyl)-[4-(3-phenyl-[1,2,4]oxadiazol-5-ylmethylene)-cyclohexyl]-methyl}-dimethylamine (more highly nonpolar diastereomer)
73. dimethyl-{3-phenyl-1-[4-(3-phenyl-[1,2,4]oxadiazol-5-ylmethylene)-cyclohexyl]-propyl}-amine (more highly polar diastereomer)
74. dimethyl-{3-phenyl-1-[4-(3-phenyl-[1,2,4]oxadiazol-5-ylmethylene)-cyclohexyl]-propyl}-amine (more highly nonpolar diastereomer)
75. {(4-fluorophenyl)-[4-(3-phenyl-[1,2,4]oxadiazol-5-ylmethylene)-cyclohexyl]-methyl}-dimethylamine (more highly polar diastereomer)
76. {(4-fluorophenyl)-[4-(3-phenyl-[1,2,4]oxadiazol-5-ylmethylene)-cyclohexyl]-methyl}-dimethylamine (more highly nonpolar diastereomer)
77. [{4-[3-(2,4-difluorophenyl)-[1,2,4]oxadiazol-5-ylmethylene]-cyclohexyl}-(3-fluorophenyl)-methyl]-dimethylamine (more highly polar diastereomer)
78. [{4-[3-(2,4-difluorophenyl)-[1,2,4]oxadiazol-5-ylmethylene]-cyclohexyl}-(3-fluorophenyl)-methyl]-dimethylamine (more highly nonpolar diastereomer)
79. ({4-[3-(4-methoxybenzyl)-[1,2,4]oxadiazol-5-ylmethylene]-cyclohexyl}-phenylmethyl)-dimethylamine (more highly polar diastereomer)
80. ({4-[3-(4-methoxybenzyl)-[1,2,4]oxadiazol-5-ylmethylene]-cyclohexyl}-phenylmethyl)-dimethylamine (more highly nonpolar diastereomer)
81. ((3-fluorophenyl)-{4-[3-(4-methoxybenzyl)-[1,2,4]oxadiazol-5-ylmethylene]-cyclohexyl}-methyl)-dimethylamine (more highly polar diastereomer)
82. ((3-fluorophenyl)-{4-[3-(4-methoxybenzyl)-[1,2,4]oxadiazol-5-ylmethylene]-cyclohexyl}-methyl)-dimethylamine (more highly nonpolar diastereomer)
83. ((4-chlorophenyl)-{4-[3-(4-methoxybenzyl)-[1,2,4]oxadiazol-5-ylmethylene]-cyclohexyl}-methyl)-dimethylamine (more highly polar diastereomer)
84. ((4-chlorophenyl)-{4-[3-(4-methoxybenzyl)-[1,2,4]oxadiazol-5-ylmethylene]-cyclohexyl}-methyl)-dimethylamine (more highly nonpolar diastereomer)
85. (1-{4-[3-(4-methoxybenzyl)-[1,2,4]oxadiazol-5-ylmethylene]-cyclohexyl}-3-phenylpropyl)-dimethylamine (more highly polar diastereomer)
86. (1-{4-[3-(4-methoxybenzyl)-[1,2,4]oxadiazol-5-ylmethylene]-cyclohexyl}-3-phenylpropyl)-dimethylamine (more highly nonpolar diastereomer)
87. ((4-fluorophenyl)-{4-[3-(4-methoxybenzyl)-[1,2,4]oxadiazol-5-ylmethylene]-cyclohexyl}-methyl)-dimethylamine (more highly polar diastereomer)

88. ((4-fluorophenyl)-{4-[3-(4-methoxybenzyl)-[1,2,4]oxadiazol-5-ylmethylene]-cyclohexyl}-methyl)-dimethylamine (more highly nonpolar diastereomer)
89. ({4-[3-(4-chlorobenzyl)-[1,2,4]oxadiazol-5-ylmethylene]-cyclohexyl}-phenylmethyl)-dimethylamine (more highly polar diastereomer)
90. ({4-[3-(4-chlorobenzyl)-[1,2,4]oxadiazol-5-ylmethylene]-cyclohexyl}-phenylmethyl) dimethylamine (more highly nonpolar diastereomer)
91. [{4-[3-(4-chlorobenzyl)-[1,2,4]oxadiazol-5-ylmethylene]-oyclohexyl}-(3-fluorophenyl)-methyl]-dimethylamine (more highly polar diastereomer)
92. [{4-[3-(4-chlorobenzyl)-[1,2,4]oxadiazol-5-ylmethylene]-oyclohexyl}-(3-fluorophenyl)methyl]-dimethylamine (more highly nonpolar diastereomer)
93. [{4-[3-(4-chlorobenzyl)-[1,2,4]oxadiazol-5-ylmethylene]-cyclohexyl}-(4-chlorophenyl)-methyl]-dimethylamine (more highly polar diastereomer)
94. [{4-[3-(4-chlorobenzyl)-[1,2,4]oxadiazol-5-ylmethylene]-cyclohexyl}-(4-chlorophenyl)-methyl]-dimethylamine (more highly nonpolar diastereomer)
95. (1-{4-[3-(4-chlorobenzyl)-[1,2,4]oxadiazol-5-ylmethylene]-oyclohexyl}-3-phenylpropyl)-dimethylamine (more highly polar diastereomer)
96. (1-{4-[3-(4-chlorobenzyl)-[1,2,4]oxadiazol-5-ylmethylene]-oyclohexyl}-3-phenylpropyl)-dimethylamine (more highly nonpolar diastereomer)
97. [{4-[3-(4-chlorobenzyl)-[1,2,4]oxadiazol-5-ylmethylene]-cyclohexyl}-(4-fluorophenyl)-methyl]-dimethylamine (more highly polar diastereomer)
98. [{4-[3-(4-chlorobenzyl)-[1,2,4]oxadiazol-5-ylmethylene]-cyclohexyl}-(4-fluorophenyl)-methyl]-dimethylamine (more highly nonpolar diastereomer)
99. {(3-fluorophenyl)-[4-(3-p-tolyl-[1,2,4]oxadiazol-5-ylmethylene)-cyclohexyl]-methyl}-dimethylamine
100. {(4-chlorophenyl)-[4-(3-p-tolyl-[1,2,4]oxadiazol-5-ylmethylene)-cyclohexyl]-methyl}-dimethylamine
101. {(4-fluorophenyl)-[4-(3-p-tolyl-[1,2,4]oxadiazol-5-ylmethylene)-cyclohexyl]-methyl}-dimethylamine (more highly polar diastereomer)
102. {(4-fluorophenyl)-[4-(3-p-tolyl-[1,2,4]oxadiazol-5-ylmethylene)-cyclohexyl]-methyl}-dimethylamine (more highly nonpolar diastereomer)
103. ({4-[3-(3,4-dimethoxyphenyl)-[1,2,4]oxadiazol-5-ylmethylene]-cyclohexyl}-phenylmethyl)-dimethylamine (more highly polar diastereomer)
104. ({4-[3-(3,4-dimethoxyphenyl)-[1,2,4]oxadiazol-5-ylmethylene]-cyclohexyl}-phenylmethyl)-dimethylamine (more highly nonpolar diastereomer)
105. [{4-[3-(3,4-dimethoxyphenyl)-[1,2,4]oxadiazol-5-ylmethylene]-cyclohexyl}-(3-fluorophenyl)-methyl]-dimethylamine (more highly polar diastereomer)
106. [{4-[3-(3,4-dimethoxyphenyl)-[1,2,4]oxadiazol-5-ylmethylene]-cyclohexyl}-(3-fluorophenyl)-methyl]-dimethylamine (more highly nonpolar diastereomer)
107. ((4-chlorophenyl)-{4-[3-(3,4-dimethoxyphenyl)-[1,2,4]oxadiazol-5-ylmethylene]-cyclohexyl}-methyl)-dimethylamine (more highly polar diastereomer)
108. ((4-chlorophenyl)-{4-[3-(3,4-dimethoxyphenyl)-[1,2,4]oxadiazol-5-ylmethylene]-cyclohexyl}-methyl)-dimethylamine (more highly nonpolar diastereomer)
109. (1-{4-[3-(3,4-dimethoxyphenyl)-[1,2,4]oxadiazol-5-ylmethylene]-cyclohexyl}-3-phenylpropyl)-dimethylamine (more highly polar diastereomer)
110. (1-{4-[3-(3,4-dimethoxyphenyl)-[1,2,4]oxadiazol-5-ylmethylene]-cyclohexyl}-3-phenylpropyl)-dimethylamine (more highly nonpolar diastereomer)
111. [{4-[3-(3,4-dimethoxyphenyl)-[1,2,4]oxadiazol-5-ylmethylene]-cyclohexyl}-(4-fluorophenyl)-methyl]-dimethylamine (more highly polar diastereomer)
112. [{4-[3-(3,4-dimethoxyphenyl)-[1,2,4]oxadiazol-5-ylmethylene]-cyclohexyl}-(4-fluorophenyl)-methyl]-dimethylamine (more highly nonpolar diastereomer)
113. ({4-[3-(3-chlorophenyl)-[1,2,4]oxadiazol-5-ylmethylene]-cyclohexyl}-phenylmethyl)-dimethylamine (more highly polar diastereomer)
114. ({4-[3-(3-chlorophenyl)-[1,2,4]oxadiazol-5-ylmethylene]-cyclohexyl}-phenylmethyl)-dimethylamine (more highly nonpolar diastereomer)
115. [{4-[3-(3-chlorophenyl)-[1,2,4]oxadiazol-5-ylmethylene]-cyclohexyl}-(3-fluorophenyl)-methyl]-dimethylamine (more highly polar diastereomer)
116. [{4-[3-(3-chlorophenyl)-[1,2,4]oxadiazol-5-ylmethylene]-cyclohexyl}-(3-fluorophenyl)-methyl]-dimethylamine (more highly nonpolar diastereomer)
117. ((4-chlorophenyl)-{4-[3-(3-chlorophenyl)-[1,2,4]oxadiazol-5-ylmethylene]-cyclohexyl}-methyl)-dimethylamine (more highly polar diastereomer)
118. ((4-chlorophenyl)-{4-[3-(3-chlorophenyl)-[1,2,4]oxadiazol-5-ylmethylene]-cyclohexyl}-methyl)-dimethylamine (more highly nonpolar diastereomer)
119. (1-{4-[3-(3-chlorophenyl)-[1,2,4]oxadiazol-5-ylmethylene]-cyclohexyl}-3-phenylpropyl)-dimethylamine (more highly polar diastereomer)
120. (1-{4-[3-(3-chlorophenyl)-[1,2,4]oxadiazol-5-ylmethylene]-cyclohexyl}-3-phenylpropyl)-dimethylamine (more highly nonpolar diastereomer)
121. [{4-[3-(3-chlorophenyl)-[1,2,4]oxadiazol-5-ylmethylene]-cyclohexyl}-(4-fluorophenyl)-methyl]-dimethylamine
122. ({4-[3-(4-tert.-butylphenyl)-[1,2,4]oxadiazol-5-ylmethylene]-cyclohexyl}-phenylmethyl)-dimethylamine (more highly polar diastereomer)
123. ({4-[3-(4-tert.-butylphenyl)-[1,2,4]oxadiazol-5-ylmethylene]-cyclohexyl}-phenylmethyl)-dimethylamine (more highly nonpolar diastereomer)
124. [{4-[3-(4-tert.-butylphenyl)-[1,2,4]oxadiazol-5-ylmethylene]-cyclohexyl}-(3-fluorophenyl)-methyl]-dimethylamine (more highly polar diastereomer)
125. [{4-[3-(4-tert.-butylphenyl)-[1,2,4]oxadiazol-5-ylmethylene]-cyclohexyl}-(3-fluorophenyl)-methyl]-dimethylamine (more highly nonpolar diastereomer)
126. [{4-[3-(4-tert.-butylphenyl)-[1,2,4]oxadiazol-5-ylmethylene]-cyclohexyl}-(4-chlorophenyl)-methyl]-dimethylamine (more highly polar diastereomer)
127. [{4-[3-(4-tert.-butylphenyl)-[1,2,4]oxadiazol-5-ylmethylene]-cyclohexyl}-(4-chlorophenyl)-methyl]-dimethylamine (more highly nonpolar diastereomer)
128. (1-{4-[3-(4-tert.-butylphenyl)-[1,2,4]oxadiazol-5-ylmethylene]-cyclohexyl}-3-phenylpropyl)-dimethylamine (more highly polar diastereomer)
129. (1-{4-[3-(4-tert.-butylphenyl)-[1,2,4]oxadiazol-5-ylmethylene]-cyclohexyl}-3-phenylpropyl)-dimethylamine (more highly nonpolar diastereomer)
130. [{4-[3-(4-tert.-butylphenyl)-[1,2,4]oxadiazol-5-ylmethylene]-cyclohexyl}-(4-fluorophenyl)-methyl]-dimethylamine (more highly polar diastereomer)
131. [{4-[3-(4-tert.-butylphenyl)-[1,2,4]oxadiazol-5-ylmethylene]-cyclohexyl}-(4-fluorophenyl)-methyl]-dimethylamine (more highly nonpolar diastereomer)
132. ({4-[3-(4-tert.-butylphenyl)-[1,2,4]oxadiazol-5-ylmethylene]-cyclohexyl}-thiophen-2-yl-methyl)-dimethylamine (more highly polar diastereomer)

133. ({4-[3-(4-tert.-butylphenyl)-[1,2,4]oxadiazol-5-ylmethylene]-cyclohexyl}-thiophen-2-yl-methyl)-dimethylamine (more highly nonpolar diastereomer)
134. dimethyl-{phenyl-[4-(3-m-tolyl-[1,2,4]oxadiazol-5-ylmethylene)-cyclohexyl]-methyl}-amine (more highly polar diastereomer)
135. dimethyl-{phenyl-[4-(3-m-tolyl-[1,2,4]oxadiazol-5-ylmethylene)-cyclohexyl]-methyl}-amine (more highly nonpolar diastereomer)
136. {(3-fluorophenyl)-[4-(3-m-tolyl-[1,2,4]oxadiazol-5-ylmethylene)-cyclohexyl]-methyl}-dimethylamine (more highly polar diastereomer)
137. {(3-fluorophenyl)-[4-(3-m-tolyl-[1,2,4]oxadiazol-5-ylmethylene)-cyclohexyl]-methyl}-dimethylamine (more highly nonpolar diastereomer)
138. {(4-chlorophenyl)-[4-(3-m-tolyl-[1,2,4]oxadiazol-5-ylmethylene)-cyclohexyl]-methyl}-dimethylamine (more highly polar diastereomer)
139. {(4-chlorophenyl)-[4-(3-m-tolyl-[1,2,4]oxadiazol-5-ylmethylene)-cyclohexyl]-methyl}-dimethylamine (more highly nonpolar diastereomer)
140. ((4-fluorophenyl)-{4-[2-(3-phenyl-[1,2,4]oxadiazol-5-yl)-vinyl]-cyclohexyl}-methyl)-dimethylamine
141. [(4-{2-[3-(2,4-difluorophenyl)-[1,2,4]oxadiazol-5-yl]-vinyl}-cyclohexyl)-(4-fluorophenyl)-methyl]-dimethylamine
142. [(4-fluorophenyl)-(4-{2-[3-(4-methoxybenzyl)-[1,2,4]oxadiazol-5-yl]-vinyl}-cyclohexyl)-methyl]-dimethylamine
143. [(4-{2-[3-(4-chlorobenzyl)-[1,2,4]oxadiazol-5-yl]-vinyl}-cyclohexyl)-(4-fluorophenyl)-methyl]-dimethylamine
144. dimethyl-(3-phenyl-1-{4-[2-(3-phenyl-[1,2,4]oxadiazol-5-yl)-vinyl]-cyclohexyl}-propyl)-amine
145. [1-(4-{2-[3-(2,4-difluorophenyl)-[1,2,4]oxadiazol-5-yl]-vinyl}-cyclohexyl)-3-phenylpropyl]-dimethylamine
146. [1-(4-{2-[3-(4-methoxybenzyl)-[1,2,4]oxadiazol-5-yl]-vinyl}-cyclohexyl)-3-phenylpropyl]-dimethylamine
147. [1-(4-{2-[3-(4-chlorobenzyl)-[1,2,4]oxadiazol-5-yl]-vinyl}-cyclohexyl)-3-phenylpropyl]-dimethylamine
148. dimethyl-(phenyl-{4-[2-(3-phenyl-[1,2,4]oxadiazol-5-yl)-vinyl]-cyclohexyl}-methyl)-amine
149. [(4-{2-[3-(4-chlorobenzyl)-[1,2,4]oxadiazol-5-yl]-vinyl}-cyclohexyl)-phenylmethyl]-dimethylamine (more highly polar diastereomer)
150. [(4-{2-[3-(4-chlorobenzyl)-[1,2,4]oxadiazol-5-yl]-vinyl}-cyclohexyl)-phenylmethyl]-dimethylamine (more highly nonpolar diastereomer)
151. [(4-chlorophenyl)-(4-{2-[3-(2,4-difluorophenyl)-[1,2,4]oxadiazol-5-yl]-vinyl}-cyclohexyl)-methyl]-dimethylamine
152. [(4-chlorophenyl)-(4-{2-[3-(4-methoxybenzyl)-[1,2,4]oxadiazol-5-yl]-vinyl}-cyclohexyl)-methyl]-dimethylamine
153. [(4-{2-[3-(4-chlorobenzyl)-[1,2,4]oxadiazol-5-yl]-vinyl}-cyclohexyl)-(4-chlorophenyl)-methyl]-dimethylamine
154. [(4-{2-[3-(4-methoxybenzyl)-[1,2,4]oxadiazol-5-yl]-vinyl}-cyclohexyl)-thiophen-2-yl-methyl]-dimethylamine
155. [(4-{2-[3-(4-chlorobenzyl)-[1,2,4]oxadiazol-5-yl]-vinyl}-cyclohexyl)-thiophen-2-yl-methyl]-dimethylamine
156. ((3-fluorophenyl)-{4-[2-(3-phenyl-[1,2,4]oxadiazol-5-yl)-vinyl]-cyclohexyl}-methyl)-dimethylamine
157. [(3-fluorophenyl)-(4-{2-[3-(4-methoxybenzyl)-[1,2,4]oxadiazol-5-yl]-vinyl}-cyclohexyl)-methyl]-dimethylamine
158. ((4-fluorophenyl)-{4-[2-(3-p-tolyl-[1,2,4]oxadiazol-5-yl)-vinyl]-cyclohexyl}-methyl)-dimethylamine
159. [(4-{2-[3-(3,4-dimethoxyphenyl)-[1,2,4]oxadiazol-5-yl]-vinyl}-cyclohexyl)-(4-fluorophenyl)-methyl]-dimethylamine
160. dimethyl-(3-phenyl-1-{4-[2-(3-p-tolyl-[1,2,4]oxadiazol-5-yl)-vinyl]-cyclohexyl}-propyl)-amine
161. [1-(4-{2-[3-(3,4-dimethoxyphenyl)-[1,2,4]oxadiazol-5-yl]-vinyl}-cyclohexyl)-3-phenylpropyl]-dimethylamine
162. dimethyl-(phenyl-{4-[2-(3-p-tolyl-[1,2,4]oxadiazol-5-yl)-vinyl]-cyclohexyl}-methyl)-amine
163. [(4-{2-[3-(3,4-dimethoxyphenyl)-[1,2,4]oxadiazol-5-yl]-vinyl}-cyclohexyl)-phenylmethyl]-dimethylamine
164. ((4-chlorophenyl)-{4-[2-(3-p-tolyl-[1,2,4]oxadiazol-5-yl)-vinyl]-cyclohexyl}-methyl)-dimethylamine
165. [(4-chlorophenyl)-(4-{2-[3-(3,4-dimethoxyphenyl)-[1,2,4]oxadiazol-5-yl]-vinyl}-cyclohexyl)-methyl]-dimethylamine
166. dimethyl-(thiophen-2-yl-{4-[2-(3-p-tolyl-[1,2,4]oxadiazol-5-yl)-vinyl]-cyclohexyl}-methyl)-amine
167. [(4-{2-[3-(3,4-dimethoxyphenyl)-[1,2,4]oxadiazol-5-yl]-vinyl}-cyclohexyl)-thiophen-2-yl-methyl]-dimethylamine
168. ((3-fluorophenyl)-{4-[2-(3-p-tolyl-[1,2,4]oxadiazol-5-yl)-vinyl]-cyclohexyl}-methyl)-dimethylamine
169. [(4-{2-[3-(3,4-dimethoxyphenyl)-[1,2,4]oxadiazol-5-yl]-vinyl}-cyclohexyl)-(3-fluorophenyl)-methyl]-dimethylamine
170. [(4-{2-[3-(3-chlorophenyl)-[1,2,4]oxadiazol-5-yl]-vinyl}-cyclohexyl)-(4-fluorophenyl)-methyl]-dimethylamine
171. [(4-{2-[3-(4-tert.-butylphenyl)-[1,2,4]oxadiazol-5-yl]-vinyl}-cyclohexyl)-(4-fluorophenyl)-methyl]-dimethylamine
172. [(4-{2-[3-(4-tert.-butylphenyl)-[1,2,4]oxadiazol-5-yl]-vinyl}-cyclohexyl)-(4-fluorophenyl)-methyl]-dimethylamine
173. ((4-fluorophenyl)-{4-[2-(3-m-tolyl-[1,2,4]oxadiazol-5-yl)-vinyl]-cyclohexyl}-methyl)-dimethylamine
174. [1-(4-{2-[3-(3-chlorophenyl)-[1,2,4]oxadiazol-5-yl]-vinyl}-cyclohexyl)-3-phenylpropyl]-dimethylamine
175. [1-(4-{2-[3-(4-tert.-butylphenyl)-[1,2,4]oxadiazol-5-yl]-vinyl}-cyclohexyl)-3-phenylpropyl]-dimethylamine (more highly polar isomer)
176. [1-(4-{2-[3-(4-tert.-butylphenyl)-[1,2,4]oxadiazol-5-yl]-vinyl}-cyclohexyl)-3-phenylpropyl]-dimethylamine (more highly nonpolar diastereomer)
177. dimethyl-(3-phenyl-1-{4-[2-(3-m-tolyl-[1,2,4]oxadiazol-5-yl)-vinyl]-cyclohexyl}-propyl)-amine (more highly polar diastereomer)
178. dimethyl-(3-phenyl-1-{4-[2-(3-m-tolyl-[1,2,4]oxadiazol-5-yl)-vinyl]-cyclohexyl}-propyl)-amine (more highly nonpolar diastereomer)
179. [(4-{2-[3-(3-chlorophenyl)-[1,2,4]oxadiazol-5-yl]-vinyl}-cyclohexyl)-phenylmethyl]-dimethylamine
180. [(4-{2-[3-(4-tert.-butylphenyl)-[1,2,4]oxadiazol-5-yl]-vinyl}-cyclohexyl)-phenylmethyl]-dimethylamine (more highly polar diastereomer)
181. [(4-{2-[3-(4-tert.-butylphenyl)-[1,2,4]oxadiazol-5-yl]-vinyl}-cyclohexyl)-phenylmethyl]-dimethylamine (more highly nonpolar diastereomer)
182. dimethyl-(phenyl-{4-[2-(3-m-tolyl-[1,2,4]oxadiazol-5-yl)-vinyl]-cyclohexyl}-methyl)-amine (more highly polar diastereomer)

183. dimethyl-(phenyl-{4-[2-(3-m-tolyl-[1,2,4]oxadiazol-5-yl)-vinyl]-cyclohexyl}-methyl)-amine (more highly nonpolar diastereomer)
184. [(4-{2-[3-(4-chlorophenyl)-[1,2,4]oxadiazol-5-yl]-vinyl}-cyclohexyl)-phenylmethyl]-dimethylamine (more highly polar diastereomer)
185. [(4-{2-[3-(4-chlorophenyl)-[1,2,4]oxadiazol-5-yl]-vinyl}-cyclohexyl)-phenylmethyl]-dimethylamine (more highly nonpolar diastereomer)
186. [(4-chlorophenyl)-(4-{2-[3-(3-chlorophenyl)-[1,2,4]oxadiazol-5-yl]-vinyl}-cyclohexyl)-methyl]-dimethylamine
187. [(4-{2-[3-(4-tert.-butylphenyl)-[1,2,4]oxadiazol-5-yl]-vinyl}-cyclohexyl)-(4-chlorophenyl)-methyl]-dimethylamine (more highly polar diastereomer)
188. [(4-{2-[3-(4-tert.-butylphenyl)-[1,2,4]oxadiazol-5-yl]-vinyl}-cyclohexyl)-(4-chlorophenyl)-methyl]-dimethylamine (more highly nonpolar diastereomer)
189. ((4-chlorophenyl)-{4-[2-(3-m-tolyl-[1,2,4]oxadiazol-5-yl)-vinyl]-cyclohexyl}-methyl)-dimethylamine (more highly polar diastereomer)
190. ((4-chlorophenyl)-{4-[2-(3-m-tolyl-[1,2,4]oxadiazol-5-yl)-vinyl]-cyclohexyl}-methyl)-dimethylamine (more highly nonpolar diastereomer)
191. [(4-chlorophenyl)-(4-{2-[3-(4-chlorophenyl)-[1,2,4]oxadiazol-5-yl]-vinyl}-cyclohexyl)-methyl]-dimethylamine
192. [(4-{2-[3-(3-chlorophenyl)-[1,2,4]oxadiazol-5-yl]-vinyl}-cyclohexyl)-thiophen-2-yl-methyl]-dimethylamine
193. [(4-{2-[3-(4-tert.-butylphenyl)-[1,2,4]oxadiazol-5-yl]-vinyl}-cyclohexyl)-thiophen-2-yl-methyl]-dimethylamine (more highly polar diastereomer)
194. [(4-{2-[3-(4-tert.-butylphenyl)-[1,2,4]oxadiazol-5-yl]-vinyl}-cyclohexyl)-thiophen-2-yl-methyl]-dimethylamine (more highly nonpolar diastereomer)
195. dimethyl-(thiophen-2-yl-{4-[2-(3-m-tolyl-[1,2,4]oxadiazol-5-yl)-vinyl]-cyclohexyl}-methyl)-amine
196. [(4-{2-[3-(4-chlorophenyl)-[1,2,4]oxadiazol-5-yl]-vinyl}-cyclohexyl)-thiophen-2-yl-methyl]-dimethylamine
197. [(4-{2-[3-(3-chlorophenyl)-[1,2,4]oxadiazol-5-yl]-vinyl}-cyclohexyl)-(3-fluorophenyl)-methyl]-dimethylamine
198. [(4-{2-[3-(4-tert.-butylphenyl)-[1,2,4]oxadiazol-5-yl]-vinyl}-cyclohexyl)-(3-fluorophenyl)-methyl]-dimethylamine (more highly polar diastereomer)
199. [(4-{2-[3-(4-tert.-butylphenyl)-[1,2,4]oxadiazol-5-yl]-vinyl}-cyclohexyl)-(3-fluorophenyl)-methyl]-dimethylamine (more highly nonpolar diastereomer)
201. ((3-fluorophenyl)-{4-[2-(3-m-tolyl-[1,2,4]oxadiazol-5-yl)-vinyl]-cyclohexyl}-methyl)-dimethylamine
202. [(4-{2-[3-(4-chlorophenyl)-[1,2,4]oxadiazol-5-yl]-vinyl}-cyclohexyl)-(3-fluorophenyl)-methyl]-dimethylamine
203. [(4-{2-[3-(2,3-dichlorophenyl)-[1,2,4]oxadiazol-5-yl]-vinyl}-cyclohexyl)-(4-fluorophenyl)-methyl]-dimethylamine
204. [(4-fluorophenyl)-(4-{2-[3-(4-trifluoromethoxyphenyl)-[1,2,4]oxadiazol-5-yl]-vinyl}-cyclohexyl)-methyl]-dimethylamine
205. [(4-{2-[3-(3,4-dimethoxybenzyl)-[1,2,4]oxadiazol-5-yl]-vinyl}-cyclohexyl)-(4-fluorophenyl)-methyl]-dimethylamine
206. [(4-{2-[3-(1,5-dimethyl-1H-pyrrol-2-yl)-[1,2,4]oxadiazol-5-yl]-vinyl}-cyclohexyl)-(4-fluorophenyl)-methyl]-dimethylamine
207. [1-(4-{2-[3-(2,3-dichlorophenyl)-[1,2,4]oxadiazol-5-yl]-vinyl}-cyclohexyl)-3-phenylpropyl]-dimethylamine
208. dimethyl-[3-phenyl-1-(4-{2-[3-(4-trifluoromethoxyphenyl)-[1,2,4]oxadiazol-5-yl]-vinyl}-cyclohexyl)-propyl]-amine (more highly polar diastereomer)
209. dimethyl-[3-phenyl-1-(4-{2-[3-(4-trifluoromethoxyphenyl)-[1,2,4]oxadiazol-5-yl]-vinyl}-cyclohexyl)-propyl]-amine (more highly nonpolar diastereomer)
210. [1-(4-{2-[3-(3,4-dimethoxybenzyl)-[1,2,4]oxadiazol-5-yl]-vinyl}-cyclohexyl)-3-phenylpropyl]-dimethylamine (more highly polar diastereomer)
211. [1-(4-{2-[3-(3,4-dimethoxybenzyl)-[1,2,4]oxadiazol-5-yl]-vinyl}-cyclohexyl)-3-phenylpropyl]-dimethylamine (more highly nonpolar diastereomer)
212. [1-(4-{2-[3-(1,5-dimethyl-1H-pyrrol-2-yl)-[1,2,4]oxadiazol-5-yl]-vinyl}-cyclohexyl)-3-phenylpropyl]-dimethylamine
213. [(4-{2-[3-(2,3-dichlorophenyl)-[1,2,4]oxadiazol-5-yl]-vinyl}-cyclohexyl)-phenylmethyl]-dimethylamine
214. [(4-{2-[3-(3,4-dimethoxybenzyl)-[1,2,4]oxadiazol-5-yl]-vinyl}-cyclohexyl)-phenylmethyl]-dimethylamine (more highly polar diastereomer)
215. [(4-{2-[3-(3,4-dimethoxybenzyl)-[1,2,4]oxadiazol-5-yl]-vinyl}-cyclohexyl)-phenylmethyl]-dimethylamine (more highly nonpolar diastereomer)
217. [(4-{2-[3-(1,5-dimethyl-1H-pyrrol-2-yl)-[1,2,4]oxadiazol-5-yl]-vinyl}-cyclohexyl)-phenylmethyl]-dimethylamine
218. [(4-chlorophenyl)-(4-{2-[3-(2,3-dichlorophenyl)-[1,2,4]oxadiazol-5-yl]-vinyl}-cyclohexyl)-methyl]-dimethylamine
219. [(4-chlorophenyl)-(4-{2-[3-(4-trifluoromethoxyphenyl)-[1,2,4]oxadiazol-5-yl]-vinyl}-cyclohexyl)-methyl]-dimethylamine
220. [(4-chlorophenyl)-(4-{2-[3-(3,4-dimethoxybenzyl)-[1,2,4]oxadiazol-5-yl]-vinyl}-cyclohexyl)-methyl]-dimethylamine
221. [(4-chlorophenyl)-(4-{2-[3-(1,5-dimethyl-1H-pyrrol-2-yl)-[1,2,4]oxadiazol-5-yl]-vinyl}-cyclohexyl)-methyl]-dimethylamine
222. [(4-{2-[3-(2,3-dichlorophenyl)-[1,2,4]oxadiazol-5-yl]-vinyl}-cyclohexyl)-thiophen-2-yl-methyl]-dimethylamine
223. dimethyl-[thiophen-2-yl-(4-{2-[3-(4-trifluoromethoxyphenyl)-[1,2,4]oxadiazol-5-yl]-vinyl}-cyclohexyl)-methyl]-amine
224. [(4-{2-[3-(1,5-dimethyl-1H-pyrrol-2-yl)-[1,2,4]oxadiazol-5-yl]-vinyl}-cyclohexyl)-thiophen-2-yl-methyl]-dimethylamine
225. [(4-{2-[3-(2,3-dichlorophenyl)-[1,2,4]oxadiazol-5-yl]-vinyl}-cyclohexyl)-(3-fluorophenyl)-methyl]-dimethylamine
226. [(3-fluorophenyl)-(4-{2-[3-(4-trifluoromethoxyphenyl)-[1,2,4]oxadiazol-5-yl]-vinyl}-cyclohexyl)-methyl]-dimethylamine (more highly polar diastereomer)
227. [(3-fluorophenyl)-(4-{2-[3-(4-trifluoromethoxyphenyl)-[1,2,4]oxadiazol-5-yl]-vinyl}-cyclohexyl)-methyl]-dimethylamine (more highly nonpolar diastereomer)
228. [(4-{2-[3-(3,4-dimethoxybenzyl)-[1,2,4]oxadiazol-5-yl]-vinyl}-cyclohexyl)-(3-fluorophenyl)-methyl]-dimethylamine (more highly polar diastereomer)
229. [(4-{2-[3-(3,4-dimethoxybenzyl)-[1,2,4]oxadiazol-5-yl]-vinyl}-cyclohexyl)-(3-fluorophenyl)-methyl]-dimethylamine (more highly nonpolar diastereomer)
231. [(4-{2-[3-(1,5-dimethyl-1H-pyrrol-2-yl)-[1,2,4]oxadiazol-5-yl]-vinyl}-cyclohexyl)-(3-fluorophenyl)-methyl]-dimethylamine
232. {(3-fluorophenyl)-[4-(3-phenyl-[1,2,4]oxadiazol-5-yl-methyl)-cyclohexyl]-methyl}-dimethylamine 233. {(4-fluorophenyl)-[4-(3-phenyl-[1,2,4]oxadiazol-5-yl-methyl)-cyclohexyl]-methyl}-dimethylamine
234. dimethyl-{phenyl-[4-(3-phenyl-[1,2,4]oxadiazol-5-yl-methyl)-cyclohexyl]-methyl}-amine
235. [{4-[3-(2,4-difluorophenyl)-[1,2,4]oxadiazol-5-ylmethyl]-cyclohexyl}-(3-fluorophenyl)-methyl]-dimethylamine
236. [{4-[3-(2,4-difluorophenyl)-[1,2,4]oxadiazol-5-ylmethyl]-cyclohexyl}-(4-fluorophenyl)-methyl]-dimethylamine
237. ((3-fluorophenyl)-{4-[3-(4-methoxybenzyl)-[1,2,4]oxadiazol-5-ylmethyl]-cyclohexyl}-methyl)-dimethylamine
238. ((4-fluorophenyl)-{4-[3-(4-methoxybenzyl)-[1,2,4]oxadiazol-5-ylmethyl]-cyclohexyl}-methyl)-dimethylamine
239. ({4-[3-(4-methoxybenzyl)-[1,2,4]oxadiazol-5-ylmethyl]-cyclohexyl}-phenylmethyl)-dimethylamine
240. [{4-[3-(4-chlorobenzyl)-[1,2,4]oxadiazol-5-ylmethyl]-cyclohexyl}-(3-fluorophenyl)-methyl]-dimethylamine
241. [{4-[3-(4-chlorobenzyl)-[1,2,4]oxadiazol-5-ylmethyl]-cyclohexyl}-(4-fluorophenyl)-methyl]-dimethylamine
242. [{4-[3-(3-chlorophenyl)-[1,2,4]oxadiazol-5-ylmethyl]-cyclohexyl}-(4-fluorophenyl)-methyl]-dimethylamine
243. ({4-[3-(3-chlorophenyl)-[1,2,4]oxadiazol-5-ylmethyl]-cyclohexyl}-phenylmethyl)-dimethylamine
244. [{4-[3-(2,3-dichlorophenyl)-[1,2,4]oxadiazol-5-ylmethyl]-cyclohexyl}-(3-fluorophenyl)-methyl]-dimethylamine
245. [{4-[3-(2,3-dichlorophenyl)-[1,2,4]oxadiazol-5-ylmethyl]-cyclohexyl}-(4-fluorophenyl)-methyl]-dimethylamine
246. ({4-[3-(2,3-dichlorophenyl)-[1,2,4]oxadiazol-5-ylmethyl]-cyclohexyl}-phenylmethyl)-dimethylamine
247. {(3-fluorophenyl)-[4-(3-p-tolyl-[1,2,4]oxadiazol-5-yl-methyl)-cyclohexyl]-methyl}-dimethylamine
248. {(4-fluorophenyl)-[4-(3-p-tolyl-[1,2,4]oxadiazol-5-yl-methyl)-cyclohexyl]-methyl}-dimethylamine
249. dimethyl-{phenyl-[4-(3-p-tolyl-[1,2,4]oxadiazol-5-yl-methyl)-cyclohexyl]-methyl}-amine
250. [{4-[3-(3,4-dimethoxyphenyl)-[1,2,4]oxadiazol-5-ylmethyl]-cyclohexyl}-(3-fluorophenyl)-methyl]-dimethylamine
251. [{4-[3-(3,4-dimethoxyphenyl)-[1,2,4]oxadiazol-5-ylmethyl]-cyclohexyl}-(4-fluorophenyl)-methyl]-dimethylamine
252. ({4-[3-(3,4-dimethoxyphenyl)-[1,2,4]oxadiazol-5-ylmethyl]-cyclohexyl}-phenylmethyl)-dimethylamine
253. [{4-[3-(4-tert.-butylphenyl)-[1,2,4]oxadiazol-5-ylmethyl]-cyclohexyl}-(3-fluorophenyl)-methyl]-dimethylamine
254. [{4-[3-(4-tert.-butylphenyl)-[1,2,4]oxadiazol-5-ylmethyl]-cyclohexyl}-(4-fluorophenyl)-methyl]-dimethylamine
255. ({4-[3-(4-tert.-butylphenyl)-[1,2,4]oxadiazol-5-ylmethyl]-cyclohexyl}-phenylmethyl)-dimethylamine
256. {(3-fluorophenyl)-[4-(3-m-tolyl-[1,2,4]oxadiazol-5-yl-methyl)-cyclohexyl]-methyl}-dimethylamine
257. {(4-fluorophenyl)-[4-(3-m-tolyl-[1,2,4]oxadiazol-5-yl-methyl)-cyclohexyl]-methyl}-dimethylamine
258. dimethyl-{phenyl-[4-(3-m-tolyl-[1,2,4]oxadiazol-5-yl-methyl)-cyclohexyl]-methyl}-amine
259. [{4-[3-(4-chlorophenyl)-[1,2,4]oxadiazol-5-ylmethyl]-cyclohexyl}-(3-fluorophenyl)-methyl]-dimethylamine
260. ({4-[3-(4-chlorophenyl)-[1,2,4]oxadiazol-5-ylmethyl]-cyclohexyl}-phenylmethyl)-dimethylamine
261. ((3-fluorophenyl)-{4-[3-(4-trifluoromethoxyphenyl)-[1,2,4]oxadiazol-5-ylmethyl]-cyclohexyl}-methyl)-dimethylamine
262. ((4-fluorophenyl)-{4-[3-(4-trifluoromethoxyphenyl)-[1,2,4]oxadiazol-5-ylmethyl]-cyclohexyl}-methyl)-dimethylamine
263. dimethyl-(phenyl-{4-[3-(4-trifluoromethoxyphenyl)-[1,2,4]oxadiazol-5-ylmethyl]-cyclohexyl}-methyl)-amine
264. ((4-fluorophenyl)-{4-[2-(3-phenyl-[1,2,4]oxadiazol-5-yl)-ethyl]-cyclohexyl}-methyl)-dimethylamine
265. dimethyl-(phenyl-{4-[2-(3-phenyl-[1,2,4]oxadiazol-5-yl)-ethyl]-cyclohexyl}-methyl)-amine
266. dimethyl-(3-phenyl-1-{4-[2-(3-phenyl-[1,2,4]oxadiazol-5-yl)-ethyl]-cyclohexyl}-propyl)-amine
267. ((3-fluorophenyl)-{4-[2-(3-phenyl-[1,2,4]oxadiazol-5-yl)-ethyl]-cyclohexyl}-methyl)-dimethylamine
268. [(4-fluorophenyl)-(4-{2-[3-(4-methoxybenzyl)-[1,2,4]oxadiazol-5-yl]-ethyl}-cyclohexyl)-methyl]-dimethylamine
269. [(4-{2-[3-(4-methoxybenzyl)-[1,2,4]oxadiazol-5-yl]-ethyl}-cyclohexyl)-phenylmethyl]-dimethylamine
270. [1-(4-{2-[3-(4-methoxybenzyl)-[1,2,4]oxadiazol-5-yl]-ethyl}-cyclohexyl)-3-phenylpropyl]-dimethylamine
271. [(3-fluorophenyl)-(4-{2-[3-(4-methoxybenzyl)-[1,2,4]oxadiazol-5-yl]-ethyl}-cyclohexyl)-methyl]-dimethylamine
272. [(4-{2-[3-(4-chlorobenzyl)-[1,2,4]oxadiazol-5-yl]-ethyl}-cyclohexyl)-(4-fluorophenyl)-methyl]-dimethylamine
273. [(4-{2-[3-(4-chlorobenzyl)-[1,2,4]oxadiazol-5-yl]-ethyl}-cyclohexyl)-phenylmethyl]-dimethylamine
274. [1-(4-{2-[3-(4-chlorobenzyl)-[1,2,4]oxadiazol-5-yl]-ethyl}-cyclohexyl)-3-phenylpropyl]-dimethylamine
275. [(4-{2-[3-(4-chlorobenzyl)-[1,2,4]oxadiazol-5-yl]-ethyl}-cyclohexyl)-(3-fluorophenyl)-methyl]-dimethylamine
276. [(4-{2-[3-(3-chlorophenyl)-[1,2,4]oxadiazol-5-yl]-ethyl}-cyclohexyl)-(4-fluorophenyl)-methyl]-dimethylamine
277. [(4-{2-[3-(3-chlorophenyl)-[1,2,4]oxadiazol-5-yl]-ethyl}-cyclohexyl)-phenylmethyl]-dimethylamine
278. [1-(4-{2-[3-(3-chlorophenyl)-[1,2,4]oxadiazol-5-yl]-ethyl}-cyclohexyl)-3-phenylpropyl]-dimethylamine
279. [(4-{2-[3-(3-chlorophenyl)-[1,2,4]oxadiazol-5-yl]-ethyl}-cyclohexyl)-(3-fluorophenyl)-methyl]-dimethylamine
280. [(4-{2-[3-(2,4-difluorophenyl)-[1,2,4]oxadiazol-5-yl]-ethyl}-cyclohexyl)-(4-fluorophenyl)-methyl]-dimethylamine
281. [(4-{2-[3-(2,4-difluorophenyl)-[1,2,4]oxadiazol-5-yl]-ethyl}-cyclohexyl)-phenylmethyl]-dimethylamine
282. [(4-{2-[3-(2,4-difluorophenyl)-[1,2,4]oxadiazol-5-yl]-ethyl}-cyclohexyl)-(3-fluorophenyl)-methyl]-dimethylamine
283. [(4-{2-[3-(3,4-dimethoxyphenyl)-[1,2,4]oxadiazol-5-yl]-ethyl}-cyclohexyl)-(4-fluorophenyl)-methyl]-dimethylamine
284. [(4-{2-[3-(3,4-dimethoxyphenyl)-[1,2,4]oxadiazol-5-yl]-ethyl}-cyclohexyl)-phenylmethyl]-dimethylamine
285. [1-(4-{2-[3-(3,4-dimethoxyphenyl)-[1,2,4]oxadiazol-5-yl]-ethyl}-cyclohexyl)-3-phenylpropyl]-dimethylamine
286. [(4-{2-[3-(3,4-dimethoxyphenyl)-[1,2,4]oxadiazol-5-yl]-ethyl}-cyclohexyl)-(3-fluorophenyl)-methyl]-dimethylamine
287. ((4-fluorophenyl)-{4-[2-(3-p-tolyl-[1,2,4]oxadiazol-5-yl)-ethyl]-cyclohexyl}-methyl)-dimethylamine 288. dimethyl-(phenyl-{4-[2-(3-p-tolyl-[1,2,4]oxadiazol-5-yl)-ethyl]-cyclohexyl}-methyl)-amine
289. dimethyl-(3-phenyl-1-{4-[2-(3-p-tolyl-[1,2,4]oxadiazol-5-yl)-ethyl]-cyclohexyl}-propyl)-amine
290. ((3-fluorophenyl)-{4-[2-(3-p-tolyl-[1,2,4]oxadiazol-5-yl)-ethyl]-cyclohexyl}-methyl)-dimethylamine
291. [(4-{2-[3-(4-tert.-butylphenyl)-[1,2,4]oxadiazol-5-yl]-ethyl}-cyclohexyl)-(4-fluorophenyl)-methyl]-dimethylamine
292. [(4-{2-[3-(4-tert.-butylphenyl)-[1,2,4]oxadiazol-5-yl]-ethyl}-cyclohexyl)-phenylmethyl]-dimethylamine
293. [1-(4-{2-[3-(4-tert.-butylphenyl)-[1,2,4]oxadiazol-5-yl]-ethyl}-cyclohexyl)-3-phenylpropyl]-dimethylamine
294. [(4-{2-[3-(4-tert.-butylphenyl)-[1,2,4]oxadiazol-5-yl]-ethyl}-cyclohexyl)-(3-fluorophenyl)-methyl]-dimethylamine
295. ((4-fluorophenyl)-{4-[2-(3-m-tolyl-[1,2,4]oxadiazol-5-yl)-ethyl]-cyclohexyl}-methyl)-dimethylamine
296. dimethyl-(phenyl-{4-[2-(3-m-tolyl-[1,2,4]oxadiazol-5-yl)-ethyl]-cyclohexyl}-methyl)-amine
297. dimethyl-(3-phenyl-1-{4-[2-(3-m-tolyl-[1,2,4]oxadiazol-5-yl)-ethyl]-cyclohexyl}-propyl)-amine
298. ((3-fluorophenyl)-{4-[2-(3-m-tolyl-[1,2,4]oxadiazol-5-yl)-ethyl]-cyclohexyl}-methyl)-dimethylamine
299. [(4-{2-[3-(4-chlorophenyl)-[1,2,4]oxadiazol-5-yl]-ethyl}-cyclohexyl)-(4-fluorophenyl)-methyl]-dimethylamine
300. [(4-{2-[3-(4-chlorophenyl)-[1,2,4]oxadiazol-5-yl]-ethyl}-cyclohexyl)-phenylmethyl]-dimethylamine
301. [1-(4-{2-[3-(4-chlorophenyl)-[1,2,4]oxadiazol-5-yl]-ethyl}-cyclohexyl)-3-phenylpropyl]-dimethylamine
302. [(4-{2-[3-(4-chlorophenyl)-[1,2,4]oxadiazol-5-yl]-ethyl}-cyclohexyl)-(3-fluorophenyl)-methyl]-dimethylamine
303. [(4-{2-[3-(2,3-dichlorophenyl)-[1,2,4]oxadiazol-5-yl]-ethyl}-cyclohexyl)-(4-fluorophenyl)-methyl]-dimethylamine
304. [(4-{2-[3-(2,3-dichlorophenyl)-[1,2,4]oxadiazol-5-yl]-ethyl}-cyclohexyl)-phenylmethyl]-dimethylamine
305. [1-(4-{2-[3-(2,3-dichlorophenyl)-[1,2,4]oxadiazol-5-yl]-ethyl}-cyclohexyl)-3-phenylpropyl]-dimethylamine
306. [(4-{2-[3-(2,3-dichlorophenyl)-[1,2,4]oxadiazol-5-yl]-ethyl}-cyclohexyl)-(3-fluorophenyl)-methyl]-dimethylamine
307. [(4-fluorophenyl)-(4-{2-[3-(4-trifluoromethoxyphenyl)-[1,2,4]oxadiazol-5-yl]-ethyl}-cyclohexyl)-methyl]-dimethylamine
308. dimethyl-[phenyl-(4-{2-[3-(4-trifluoromethoxyphenyl)-[1,2,4]oxadiazol-5-yl]-ethyl}-cyclohexyl)-methyl]-amine
309. dimethyl-[3-phenyl-1-(4-{2-[3-(4-trifluoromethoxyphenyl)-[1,2,4]oxadiazol-5-yl]-ethyl}-cyclohexyl)-propyl]-amine
310. [(3-fluorophenyl)-(4-{2-[3-(4-trifluoromethoxyphenyl)-[1,2,4]oxadiazol-5-yl]-ethyl}-cyclohexyl)-methyl]-dimethylamine
311. (4-((3-(4-fluorobenzyl)-1,2,4-oxadiazol-5-yl)methyl)cyclohexyl)(4-fluorophenyl)-N,N-dimethylmethanamine
312. (4-((3-(4-fluorobenzyl)-1,2,4-oxadiazol-5-yl)methyl)cyclohexyl)-N,N-dimethyl(phenyl)methanamine
313. (4-((3-(3-chlorobenzyl)-1,2,4-oxadiazol-5-yl)methyl)cyclohexyl)(3-fluorophenyl)-N,N-dimethylmethanamine
314. (4-((3-(3-chlorobenzyl)-1,2,4-oxadiazol-5-yl)methyl)cyclohexyl)(4-fluorophenyl)-N,N-dimethylmethanamine
315. (4-((3-(3-chlorobenzyl)-1,2,4-oxadiazol-5-yl)methyl)cyclohexyl)-N,N-dimethyl(phenyl)methanamine
316. (4-((3-(3-bromophenyl)-1,2,4-oxadiazol-5-yl)methyl)cyclohexyl)(3-fluorophenyl)-N,N-dimethylmethanamine
317. (4-((3-(3-bromophenyl)-1,2,4-oxadiazol-5-yl)methyl)cyclohexyl)(4-fluorophenyl)-N,N-dimethylmethanamine
318. (4-((3-(3-bromophenyl)-1,2,4-oxadiazol-5-yl)methyl)cyclohexyl)-N,N-dimethyl(phenyl)methanamine
319. (4-((3-(4-bromobenzyl)-1,2,4-oxadiazol-5-yl)methyl)cyclohexyl)(3-fluorophenyl)-N,N-dimethylmethanamine
320. (4-((3-(4-bromobenzyl)-1,2,4-oxadiazol-5-yl)methyl)cyclohexyl)(4-fluorophenyl)-N,N-dimethylmethanamine
321. (4-((3-(4-bromobenzyl)-1,2,4-oxadiazol-5-yl)methyl)cyclohexyl)-N,N-dimethyl(phenyl)methanamine
322. (3-fluorophenyl)-N,N-dimethyl(4-((3-(thiophen-2-ylmethyl)-1,2,4-oxadiazol-5-yl)methyl)cyclohexyl)methanamine
323. (4-fluorophenyl)-N,N-dimethyl(4-((3-(thiophen-2-ylmethyl)-1,2,4-oxadiazol-5-yl)methyl)cyclohexyl)methanamine
324. N,N-dimethyl(phenyl)(4-((3-(thiophen-2-ylmethyl)-1,2,4-oxadiazol-5-yl)methyl)cyclohexyl)methanamine
325. (4-((3-benzyl-1,2,4-oxadiazol-5-yl)methyl)cyclohexyl)(3-fluorophenyl)-N,N-dimethylmethanamine
326. (4-((3-benzyl-1,2,4-oxadiazol-5-yl)methyl)cyclohexyl)(4-fluorophenyl)-N,N-dimethylmethanamine
327. (4-((3-benzyl-1,2,4-oxadiazol-5-yl)methyl)cyclohexyl)-N,N-dimethyl(phenyl)methanamine
328. (3-fluorophenyl)-N,N-dimethyl(4-((3-phenethyl-1,2,4-oxadiazol-5-yl)methyl)cyclohexyl)methanamine
329. (4-fluorophenyl)-N,N-dimethyl(4-((3-phenethyl-1,2,4-oxadiazol-5-yl)methyl)cyclohexyl)methanamine
330. N,N-dimethyl(4-((3-phenethyl-1,2,4-oxadiazol-5-yl)methyl)cyclohexyl)(phenyl)methanamine
331. (4-((3-((1H-indol-3-yl)methyl)-1,2,4-oxadiazol-5-yl)methyl)cyclohexyl)(3-fluorophenyl)-N,N-dimethylmethanamine The present invention also provides a method for producing an oxadiazole derivative according to the invention. The substances according to the invention may be produced by reacting amide oximes of the general formula D in a reaction medium with addition of a base, for example NaH, with both saturated and unsaturated esters of the general formula A to yield the compounds according to the invention.

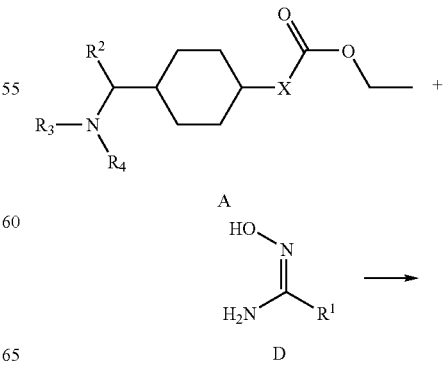

-continued

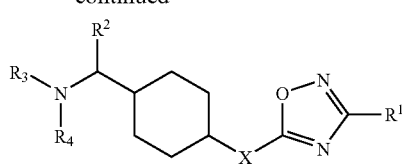

X CH, CH$_2$, CH=CH, CH$_2$CH$_2$, CH$_2$CH=CH or CH$_2$CH$_2$CH$_2$
n = 0, 1, 2

In order to produce the esters of the general formula A, the keto function of 4-oxocyclohexanecarboxylic acid esters,

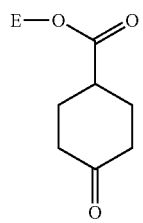

wherein E denotes a C$_{1-6}$alkyl residue, preferably ethyl, is protected using methods known to a person skilled in the art,

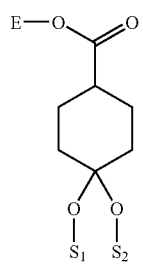
F wherein S$^1$ and S$^2$ in each case denote a protective group, preferably form a ring and together denote —CH$_2$—CH$_2$—. The ester F is reduced with a reducing agent, for example diisobutylaluminium hydride to yield the aldehyde G

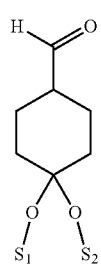
G

By adding an amine of the general formula R$^3$R$^4$NH and a cyanide, for example KCN or NaCN, the aldehyde G is reacted, with addition of an acid, for example hydrochloric acid, in an organic solvent, for example methanol or ethanol, to yield the nitrile H.

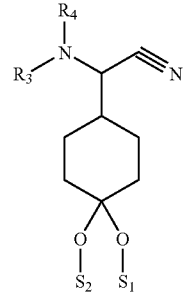
H

The nitrile H is reacted with a Grignard reagent of the general formula R$^2$MgHal, wherein Hal denotes for Br, Cl or I, or an organometallic compound of the general formula R$^2$Li in an organic solvent, for example diethyl ether, dioxane or tetrahydrofuran, to yield a compound of the general formula J.

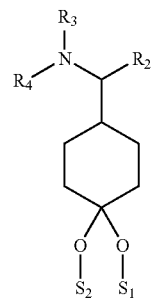
J

The protective groups are eliminated by conventional methods, so giving rise to the ketone K.

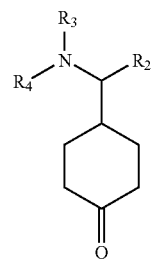
K

The aldehyde L

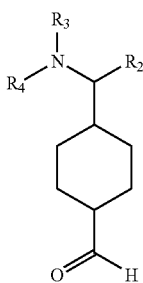

is obtained by reacting the ketone K with (methoxymethyl)triphenylphosphonium chloride and a strong base, for example potassium tert.-butylate, at a temperature of between −20° C. and +30° C. An aldehyde of the general formula M is obtained by reacting aldehyde L with (methoxymethyl)triphenylphosphonium chloride and a strong base, for example potassium tert.-butylate at a temperature of between −20° C. and +30° C. By repeating the last reaction step, aldehydes of the general formula N, in which n denotes 2, are obtained.

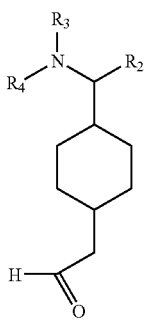

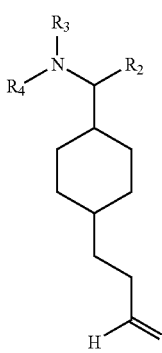

A phosphonoacetic acid ester, preferably phosphonoacetic acid trimethyl ester or phosphonoacetic acid triethyl ester, is reacted first with a strong base, preferably potassium tert.-butylate, sodium hydride or butyllithium, then with a ketone of the general formula K or an aldehyde L, M or N. This gives rise to the α,β-unsaturated esters of the general formula A.

The double bond may optionally also be reduced to yield the saturated esters of the general formula A. The double bond is here reduced using methods known from the literature, preferably by heterogeneous, catalytic hydrogenation on palladium or platinum catalysts or by homogeneously catalysed hydrogenation with rhodium catalysts, in each case at temperatures of between RT and 60° C. and under hydrogen pressures of between 1 bar and 6 bar, particularly preferably at RT under a hydrogen pressure of between 2 and 3 bar on palladium on carbon.

The diastereomers optionally arising during synthesis may be separated using methods known to a person skilled in the art for separating diastereomers, for example by normal phase or reversed phase chromatography, in particular on silica gel. RP-HPLC (mobile phase acetonitrile/water or methanol/water) is particularly suitable for separating the diastereomers.

It has been found that the substances according to the invention not only bind to the μ opioid receptor, but also inhibit serotonin and noradrenaline reuptake. Noradrenalin and serotonin reuptake inhibitors have an antidepressant and anxiolytic action, but are also suitable for treating pain (Analgesics—from Chemistry and Pharmacology to Clinical Application, Wiley 2002, pp. 265-284).

The substances according to the invention are suitable as pharmaceutical active ingredients in medicaments. The present invention therefore also provides medicaments containing at least one substituted oxadiazole derivative according to the invention, and optionally suitable additives and/or auxiliary substances and/or optionally further active ingredients.

Apart from at least one substituted oxadiazole derivative according to the invention, the medicaments according to the invention optionally contain suitable additives and/or auxiliary substances, such as excipients, fillers, solvents, diluents, dyes and/or binders and may be administered as liquid dosage forms in the form of solutions for injection, drops or juices, or as semisolid dosage forms in the form of granules, tablets, pellets, patches, capsules, dressings or aerosols. Selection of the auxiliary substances etc. and the quantities thereof which are to be used depends upon whether the medicament is to be administered orally, perorally, parenterally, intravenously, intraperitoneally, intradermally, intramuscularly, intranasally, buccally, rectally or topically, for example onto the skin, mucous membranes or into the eyes. Preparations in the form of tablets, coated tablets, capsules, granules, drops, juices and syrups are suitable for oral administration, while solutions, suspensions, easily reconstitutible dried preparations and sprays are suitable for parenteral, topical and inhalatory administration. Oxadiazole derivatives according to the invention in a depot in dissolved form or in a dressing, optionally with the addition of skin penetration promoters, are suitable percutaneous administration preparations. Orally or percutaneously administrable formulations may release the oxadiazole derivatives according to the invention in delayed manner. In principle, other additional active ingredients known to the person skilled in the art may be added to the medicaments according to the invention.

The quantity of active substance to be administered to the patient varies as a function of patient weight, mode of administration, the indication and the severity of the condition. Conventionally, 0.005 to 20 mg/kg, preferably 0.05 to 5 mg/kg of at least one oxadiazole derivative according to the invention are administered.

The medicament may contain an oxadiazole derivative according to the invention as a pure diastereomer and/or enantiomer, as a racemate or as a non-equimolar or equimolar mixture of the diastereomers and/or enantiomers.

The present invention also provides the use of an oxadiazole derivative according to the invention for producing a medicament for the treatment of pain, in particular acute, neuropathic or chronic pain.

The present invention also provides the use of an oxadiazole derivative according to the invention for producing a medicament for treating depression and/or for anxiolysis.

The substituted oxadiazole derivatives of the general formula I are also suitable for treating urinary incontinence, diarrhea, pruritus, alcohol and drug abuse, dependency on medicines and lack of drive.

The present invention accordingly also provides the use of a substituted oxadiazole derivative of the general formula I for producing a medicament for treating urinary incontinence, diarrhea, pruritus, alcohol and drug abuse, dependency on medicines and lack of drive.

EXAMPLES

Synthesis of Amide Oximes

The amide oximes are either commercially obtainable or may be produced from the corresponding nitriles as described in L. J. Street et al. J. Med. Chem. 1993, 36, 1529-1538.

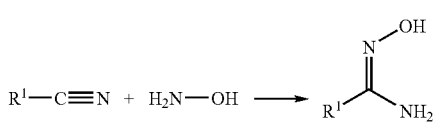

The following amide oximes were synthesised:

2,4-difluoro-N'-hydroxybenzimidamide 1 ($R^1$=2,4-difluorophenyl)

N'-hydroxybenzimidamide 2 ($R^1$=phenyl)

3,4-dimethoxy-N'-hydroxybenzimidamide 3 ($R^1$=3,4-dimethoxyphenyl)

4-methyl-N'-hydroxybenzimidamide 4 ($R^1$=4-methylphenyl)

3-chloro-N'-hydroxybenzimidamide 5 ($R^1$=3-chlorophenyl)

N'-hydroxy-4-(trifluoromethyl)benzimidamide 6 ($R^1$=4-trifluoromethylphenyl)

2-(4-chlorophenyl)-N'-hydroxyacetimidamide 7 ($R^1$=CH$_2$-4-chlorophenyl)

N'-hydroxy-2-(4-methoxyphenyl)acetimidamide 8 ($R^1$=CH$_2$-4-methoxyphenyl)

N'-hydroxyisonicotinimidamide 9 ($R^1$=4-pyridine)

N'-hydroxynicotinimidamide 10 ($R^1$=3-pyridine)

Synthesis of the ketones and aldehydes of the general formulae K, L and M, wherein $R^3$ and $R^4$ mean methyl (general formulae $K_a$, $L_a$ and $M_a$)

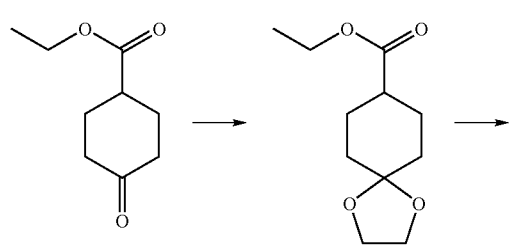

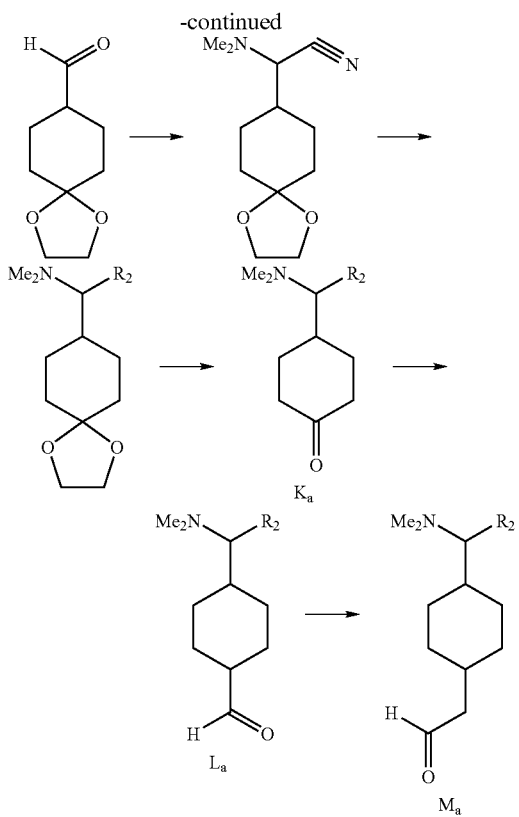

1st Stage

Synthesis of the 1,4-dioxaspiro[4.5]decane-8-carboxylic acid ethyl ester

4-Oxocyclohexanecarboxylic acid ethyl ester (52.8 g, 0.31 mol, Merck, order no. 814249), ethylene glycol (67.4 g, 1.08 mol) and p-toluenesulfonic acid (0.7 g) in toluene (160 ml) were stirred for 20 h at RT, the reaction solution poured into diethyl ether (300 ml) and washed with water, sodium hydrogencarbonate solution and sodium chloride solution. The solution was dried (Na$_2$SO$_4$), evaporated under a vacuum and the remaining colorless liquid further processed without purification.

2nd Stage

Synthesis of 1,4-dioxaspiro[4.5]decane-8-carbaldehyde

A solution of 1,4-dioxaspiro[4.5]decane-8-carboxylic acid ethyl ester (32.13 g, 150 mmol) in absol. toluene (160 ml) was combined dropwise at −70 to −65° C. under argon with diisobutylaluminium hydride (1.5 M solution in toluene, 102 ml, 153 mmol) and stirred for 30 min. The batch was then quenched at −70 to −60° C. by addition of methanol (80 ml). The reaction solution was heated to RT, combined with saturated sodium chloride solution (100 ml) and the reaction solution removed by suction filtration through diatomaceous earth. The diatomaceous earth was washed twice with ethyl acetate, the aqueous solution separated and extracted twice with ethyl acetate. The combined organic extracts were washed with saturated sodium chloride solution, dried over sodium sulfate and evaporated under a vacuum.

3rd Stage

Synthesis of dimethylamino-(1,4-dioxaspiro[4.5]dec-8-yl)-acetonitrile 40 percent strength aqueous dimethylamine solution (85 ml, 0.67 mol), 1,4-dioxaspiro-[4.5]decane-8-carbaldehyde (240 g, 0.141 mol) and potassium cyanide (22.05 g, 0.338 mol) were added with ice cooling to a mixture of 4N hydrochloric acid (37 ml) and methanol (22 ml). The mixture was stirred at room temperature for 4 d and then, after addition of water (80 ml), extracted with diethyl ether (4×100 ml). The organic phase was dried over sodium sulfate, evaporated under a vacuum and the product obtained as a white solid.

4th stage

Synthesis of [(1,4-dioxaspiro[4.5]dec-8-yl)-methyl]-dimethylamine

A 1M solution of the corresponding Grignard reagent in THF or diethyl ether (220 ml, 220 mmol) was combined dropwise under argon and with ice cooling with a solution of the aminonitrile (88 mmol) in absol. THF (160 ml) or absol. diethyl ether (160 ml), depending on the solvent used for the Grignard reagent, and stirred for 20 h at RT. The reaction mixture was worked up by adding saturated ammonium chloride solution (100 ml) and water (100 ml) with ice cooling and extracting with diethyl ether (3×100 ml). The organic phase was washed with water and saturated sodium chloride solution, dried ($Na_2SO_4$) and evaporated. The resultant product was used in the next stage without further purification.

5th Stage

Synthesis of 4-[dimethylaminomethyl]-cyclohexanone $K_a$

The crude product of the corresponding [(1,4-dioxaspiro [4.5]dec-8-yl)-methyl]-dimethylamine (88 mmol) was dissolved in water (40 ml), combined with conc. hydrochloric acid (59 ml) and stirred for 20 h at RT. The reaction mixture was extracted with diethyl ether (2×100 ml), the aqueous phase was alkalized with 5N NaOH with ice cooling, extracted with dichloromethane (3×100 ml), dried and evaporated. The products were obtained as white solids or oils.

6th Stage

Synthesis of 4-[dimethylaminomethyl]-cyclohexanecarbaldehyde $L_a$ (Methoxymethyl)triphenylphosphonium chloride (25.7 g, 75 mmol) was suspended in absol. THF (100 ml) under argon, combined dropwise at 0° C. with potassium tert.-butylate (8.42 g, 75 mmol), dissolved in absol. THF (70 ml), and then stirred for a further 15 min at 0° C. At RT, the corresponding 4-[dimethylaminomethyl]-cyclohexanone $K_a$ (50 mmol), dissolved in absol. THF (75 ml), was then added dropwise to the above solution and stirred overnight at RT. The mixture was hydrolysed by dropwise addition of water (38 ml) and 6N HCl (112 ml) with cooling with ice water. After stirring for 1 h at RT, extraction was performed with ether (10×50 ml) and the aqueous phase was adjusted to pH 11 with 5N NaOH, extracted with ethyl acetate (3×50 ml), dried over $Na_2SO_4$ and evaporated under a vacuum. The crude product was purified by flash chromatography with ethyl acetate/cyclohexane (1:1). Two diastereomers in various ratios were generally obtained.

7th Stage

Synthesis of {4-[dimethylaminomethyl]-cyclohexyl}-acetaldehyde $M_a$ (Methoxymethyl)triphenylphosphonium chloride (43.53 g, 127 mmol) was suspended in absol. THF (200 ml) under argon, combined dropwise at 0° C. with potassium tert.-butylate (14.25 g, 127 mmol), dissolved in absol. THF (130 ml), and then stirred for a further 15 min at 0° C. At RT the corresponding 4-[dimethylaminomethyl]-cyclohexanecarbaldehyde $L_a$ (85 mmol), dissolved in absol. THF (130 ml), was then added dropwise and stirred overnight at RT. The mixture was hydrolysed by dropwise addition of water (80 ml) and 6N HCl (200 ml) with cooling with ice water. After stirring for 1 h at RT, extraction was performed ten times with ether (100 ml on each occasion). The aqueous phase was adjusted to pH 11 with 5N NaOH, extracted three times with ethyl acetate (100 ml on each occasion), dried over $Na_2SO_4$ and evaporated under a vacuum. The crude product was purified by flash chromatography with ethyl acetate/cyclohexane (1:1 or 1:2) Two diastereomers in various ratios were generally obtained.

Synthesis of the Cyclohexylideneacetic Esters

The cyclohexylideneacetic esters were prepared from the corresponding ketones with phosphonoacetic triethyl ester by the Horner method.

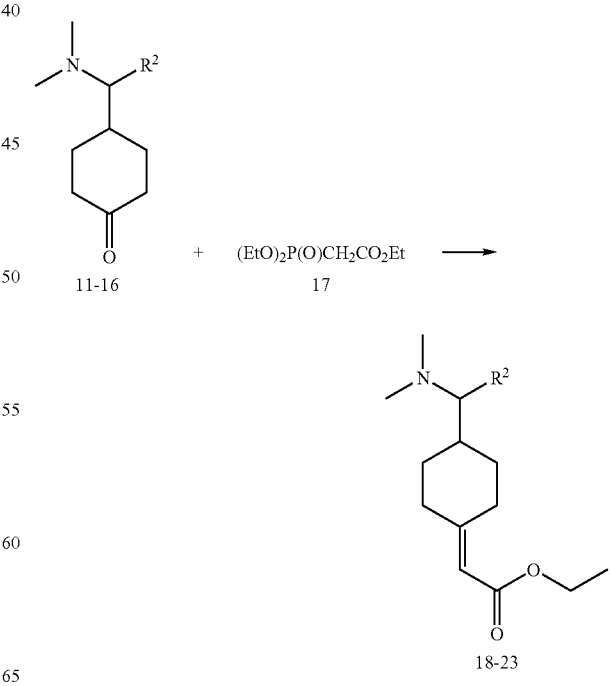

The following ketones were used:
4-(dimethylaminophenylmethyl)-cyclohexanone 11 ($R^2$=phenyl)
4-[dimethylamino-(3-fluorophenyl)-methyl]-cyclohexanone 12 ($R^2$=3-fluorophenyl)
4-[dimethylamino-(4-fluorophenyl)-methyl]-cyclohexanone 13 ($R^2$=4-fluorophenyl)
4-[(4-chlorophenyl)-dimethylaminomethyl]-cyclohexanone 14 ($R^2$=4-chlorophenyl)
4-(1-dimethylamino-3-phenylpropyl)-cyclohexanone 15 ($R^2$=phenethyl)
4-(dimethylamino-thiophen-2-yl-methyl)-cyclohexanone 16 ($R^2$=2-thiophene)

[4-(dimethylaminophenylmethyl)-cyclohexylidene]-acetic acid ethyl ester 18 ($R^2$=phenyl)

Potassium tert.-butylate (15.15 g, 0.135 mol) was added to a solution of phosphonoacetic acid triethyl ester 17 (Acros, order no. 139705000, 30.26 g, 0.135 mol) in absol. DMF (200 ml) under argon and stirred for 10 min. The ketone 11 (20.82 g, 0.09 mol), dissolved in DMF (200 ml), was then added dropwise. A solid precipitates after approx. 20 min. To enhance intermixing, the batch was diluted by addition of DMF (200 ml), stirred for 3 h at RT and thereafter poured onto ice. The reaction mixture was extracted with diethyl ether (3×100 ml) and the organic phase was washed with water and saturated sodium chloride solution, dried and evaporated under a vacuum. The crude product was purified by flash chromatography with ethyl acetate/cyclohexane (1:2). A mixture of the E/Z isomers in a ratio of approx. 1:1 is obtained.

Yield: 21.83 g (80%), oil $^{13}$C-NMR (CDCl$_3$): 25.93; 26.58; 27.09; 29.21; 29.90; 30.32; 30.73; 30.77; 35.38; 35.66; 38.73; (C$_4$); 40.06; 40.90; 41.19 (N(CH$_3$)$_2$); 48.78; 65.15; 68.22 (CH); 125.36; 127.99; 128.05; 142.69.

{4-[Dimethylamino-(3-fluorophenyl)-methyl]-cyclohexylidene}-acetic acid ethyl ester 19 ($R^2$=3-fluorophenyl)

Potassium tert.-butylate (15.15 g, 0.135 mol) was added to a solution of phosphonoacetic acid triethyl ester 17 (30.26 g, 0.135 mol) in absol. DMF (200 ml) under argon and stirred for 10 min. The ketone 12 (22.43 g, 0.09 mol), dissolved in DMF (200 ml), was then added dropwise. A solid precipitated after approx. 20 min. To enhance intermixing, the batch was diluted by addition of DMF (200 ml), stirred for 3 h at RT and thereafter poured onto ice. The reaction mixture was extracted with diethyl ether (3×100 ml) and the organic phase was washed with water and saturated NaCl solution, dried and evaporated under a vacuum. The crude product was purified by flash chromatography with ethyl acetate/cyclohexane (1:2). A mixture of the E/Z isomers in a ratio of approx. 1:1 is obtained.

Yield: 24.78 g (86%), oil $^{13}$C-NMR (CDCl$_3$): 14.36; 28.72; 28.92; 29.90; 30.39; 31.76; 30.06; 32.31; 36.96; 37.13; 38.12; 38.17; 41.91; 42.04 (N(CH$_3$)$_2$); 59.40; 74.21; 74.25; 113.15; 113.17; 113.53; 113.56; 113.74; 113.77; 115.47; 115.68; 124.78; 128.79; 128.86; 139.59; 139.66; 139.78; 139.83; 161.09; 162.18; 162.22; 163.52; 166.34; 171.55.

{4-[Dimethylamino-(4-fluorophenyl)-methyl]-cyclohexylidene}-acetic acid ethyl ester 20 ($R^2$=4-fluorophenyl)

Potassium tert.-butylate (13.46 g, 0.12 mol) was added to a solution of phosphonoacetic acid triethyl ester 17 (26.9 g, 0.12 mol) in absol. DMF (250 ml) under argon and stirred for 10 min. The ketone 13 (19.95 g, 0.08 mol), dissolved in DMF (200 ml), was then added dropwise. A solid precipitated after approx. 20 min. To enhance intermixing, the batch was diluted by addition of DMF (200 ml), stirred for 3 h at RT and thereafter poured onto ice. The reaction mixture was extracted with diethyl ether (3×100 ml) and the organic phase was washed with water and saturated NaCl solution, dried and evaporated under a vacuum. The crude product was purified by flash chromatography with ethyl acetate/cyclohexane (1:2). A mixture of the E/Z isomers in a ratio of approx. 1:1 is obtained.

Yield: 19.7 g (77%), oil $^{13}$C-NMR (CDCl$_3$): 14.18; 28.56; 28.76; 29.69; 30.17; 31.51; 32.24; 37.03; 38.07; 38.11; 41.80; 41.93; 59.34; 73.80; 73.84; 113.12; 114.24; 114.53; 130.35; 130.45; 132.48; 132.65; 160.11; 162.53; 162.59; 163.35; 166.54.

{4-[(4-Chlorophenyl)-dimethylaminomethyl]-cyclohexylidene}-acetic acid ethyl ester 21 ($R^2$=4-chlorophenyl)

Potassium tert.-butylate (11.78 g, 0.105 mol) was added to a solution of phosphonoacetic acid triethyl ester 17 (23.53 g, 0.105 mol) in absol. DMF (200 ml) under argon and stirred for 10 min. The ketone 14 (18.6 g, 0.07 mol) was then dissolved in DMF (200 ml) and added dropwise. A solid precipitated after approx. 20 min. To enhance intermixing, the batch was diluted by addition of DMF (200 ml), stirred for 3 h at RT and thereafter poured onto ice. The reaction mixture was extracted with diethyl ether (3×100 ml) and the organic phase was washed with water and saturated NaCl solution, dried and evaporated under a vacuum. The crude product was purified by flash chromatography with ethyl acetate/cyclohexane (1:2). A mixture of the E/Z isomers in a ratio of approx. 1:1 is obtained.

Yield: 18.85 g (80%), oil $^{13}$C-NMR (CDCl$_3$): 14.36; 25.58; 26.60; 28.37; 28.91; 29.74; 30.06; 30.25; 31.59; 32.32; 33.90; 34.19; 36.94; 37.12; 38.12 (C$_4$); 41.62; 41.96; 42.09 (N(CH$_3$)$_2$); 43.16; 59.40; 60.40; 73.29; 73.53; 73.98; 74.02; 113.15; 124.44; 124.92; 127.56; 127.67; 130.23; 130.42; 130.78; 131.02; 132.41; 134.88; 135.20; 135.31; 135.49; 162.13; 162.18; 166.32; 171.52.

[4-(1-Dimethylamino-3-phenylpropyl)-cyclohexylidene]-acetic acid ethyl ester 22 ($R^2$=phenethyl)

Potassium tert.-butylate (14.8 g, 0.132 mol) was added to a solution of phosphonoacetic acid triethyl ester 17 (29.6 g, 0.132 mol) in absol. DMF (150 ml) under argon and stirred for 10 min. The ketone 15 (22.8 g, 0.088 mol), dissolved in DMF (225 ml), was then added dropwise. After stirring for a further 3 h at RT, the solution was poured onto ice (approx. 1 L). The reaction mixture was extracted with diethyl ether (3×150 ml) and the organic phase was washed with water and saturated NaCl solution, dried (Na$_2$SO$_4$) and evaporated under vacuum. The crude product was purified by flash chromatography with ethyl acetate/cyclohexane (1:2).

Yield: 18.85 g (80%), oil $^{13}$C-NMR (CDCl$_3$): 14.28; 29.01; 29.13; 29.18; 31.05; 31.63; 32.15; 35.37; 37.29; 37.36; 37.63; 39.37; 39.60; 41.10; 41.25 (N(CH$_3$)$_2$); 59.45; 67.40; 67.46; 112.95; 113.00; 114.10; 125.68; 128.28; 142.71; 142.74; 162.98; 163.06; 166.79.

[4-(Dimethylamino-thiophen-2-yl-methyl)-cyclohexylidene]-acetic acid ethyl ester 23

Potassium tert.-butylate (15.15 g, 0.135 mol) was added to a solution of phosphonoacetic acid triethyl ester 17 (30.26 g, 0.135 mol) in absol. DMF (200 ml) under argon and stirred for 10 min. The ketone 16 (21.36 g, 0.09 mol), dissolved in DMF (200 ml), was then added dropwise, stirred for 3 h at RT and thereafter poured onto ice. The reaction mixture was extracted with diethyl ether (3×100 ml) and the organic phase was washed with water and saturated NaCl solution, dried and evaporated under a vacuum. The crude product was purified by flash chromatography with ethyl acetate/cyclohexane (1:2).

Yield: 23.9 g (86%), oil $^{13}$C-NMR (CDCl$_3$): 14.27; 28.57; 28.62; 30.98; 31.34; 31.47; 31.71; 32.09; 36.17; 36.84; 37.62; 40.00; 41.21; 41.33; 59.44; 69.11; 69.20; 113.20; 123.89; 126.09; 126.44; 139.52; 139.71; 162.69; 162.73; 166.69.

Synthesis of Cyclohexylacrylic Acid Esters

The cyclohexylacrylic acid esters were prepared from the corresponding aldehydes with phosphonoacetic triethyl ester by the Horner method. The following aldehydes were used:
4-[dimethylamino-(phenyl)-methyl]-cyclohexanecarbaldehyde 24 (R$^2$=phenyl)
4-[dimethylamino-(3-fluorophenyl)-methyl]-cyclohexanecarbaldehyde 25 (R$^2$=3-fluorophenyl)
4-[dimethylamino-(4-fluorophenyl)-methyl]-cyclohexanecarbaldehyde 26 (R$^2$=4-fluorophenyl)
4-[(4-chlorophenyl)-dimethylaminomethyl]-cyclohexanecarbaldehyde 27 (R$^2$=4-chlorophenyl)
4-(1-dimethylamino-3-phenylpropyl)-cyclohexanecarbaldehyde 28 (R$^2$=phenethyl)
4-(dimethylamino-thiophen-2-yl-methyl)-cyclohexanecarbaldehyde 29 (R$^2$=2-thiophene)

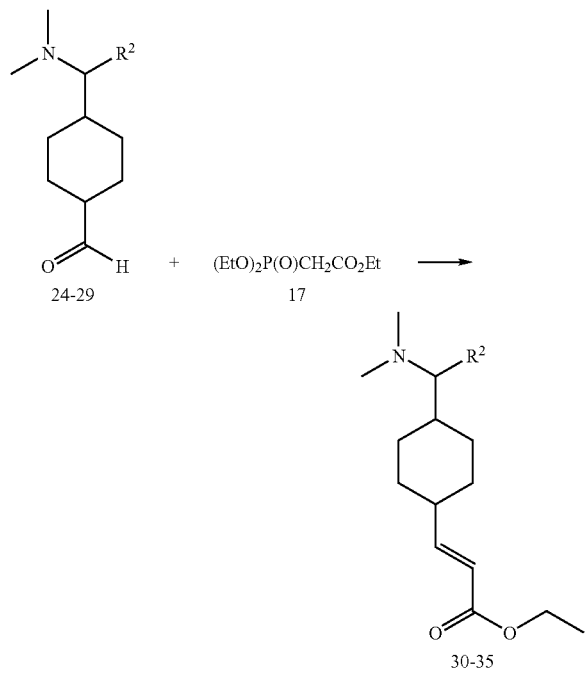

3-[4-(dimethylaminophenylmethyl)-cyclohexyl]-acrylic acid ethyl ester 30 (R$^2$=phenyl)

Potassium tert.-butylate (16.83 g, 0.15 mol) was added to a solution of phosphonoacetic acid triethyl ester 17 (33.62 g, 0.15 mol) in absol. DMF (250 ml) under argon and stirred for 10 min. The aldehyde 24 (24.27 g, 0.099 mol), dissolved in DMF (250 ml), was then added dropwise. The batch was stirred for 3 h at RT and thereafter poured onto ice. The reaction mixture was extracted with diethyl ether (3×200 ml) and the organic phase was washed with water and saturated NaCl solution, dried and evaporated under a vacuum. The crude product was purified by flash chromatography with ethyl acetate/cyclohexane (1:2). A mixture of the E/Z isomers in a ratio of approx. 6:1 is obtained.

Yield: 27.2 g (87%), oil $^{13}$C-NMR (CDCl$_3$): 14.22; 25.94; 27.92; 28.23; 28.33; 28.65; 30.18; 30.45; 30.60; 31.45; 31.63; 32.15; 33.03; 37.74; 38.10; 38.55; 40.71; 41.04; 41.30; 41.97; 59.67; 60.05; 71.34; 74.89; 75.61; 117.96; 118.97; 120.02; 126.81; 127.55; 137.20; 153.31; 153.90; 155.25; 166.28; 166.99.

3-{4-[Dimethylamino-(3-fluorophenyl)-methyl]-cyclohexyl}-acrylic acid ethyl ester 31 (R$^2$=3-fluorophenyl)

Potassium tert.-butylate (12.34 g, 0.11 mol) was added to a solution of phosphonoacetic acid triethyl ester 17 (24.66 g, 0.11 mol) in absol. DMF (200 ml) under argon and stirred for 10 min. The aldehyde 25 (19.3 g, 0.073 mol), dissolved in DMF (200 ml), was then added dropwise. The batch was stirred for 3 h at RT and thereafter poured onto ice. The reaction mixture was extracted with diethyl ether (3×200 ml) and the organic phase was washed with water and saturated NaCl solution, dried and evaporated under a vacuum. The crude product was purified by flash chromatography with ethyl acetate/cyclohexane (1:2).

Yield: 21.9 g (90%), oil $^{13}$C-NMR (CDCl$_3$): 14.26; 25.82; 28.28; 28.49; 30.09; 30.35; 31.38; 31.56; 32.07; 35.80; 37.54; 38.12; 40.68; 41.05; 41.31; 41.98; 59.75; 60.14; 75.07; 113.57; 113.84; 115.67; 115.94; 118.02; 119.04; 120.12; 125.03; 128.88; 140.13; 153.18; 153.80; 155.20; 160.92; 164.17; 167.03.

3-{4-[Dimethylamino-(4-fluorophenyl)-methyl]-cyclohexyl}-acrylic acid ethyl ester 32 (R$^2$=4-fluorophenyl)

Potassium tert.-butylate (12.56 g, 0.112 mol) was added to a solution of phosphonoacetic acid triethyl ester 17 (25.1 g, 0.112 mol) in absol. DMF (150 ml) under argon and stirred for 10 min. The aldehyde 26 (19.9 g, 0.075 mol), dissolved in DMF (225 ml), was then added dropwise. The batch was stirred for 3 h at RT and thereafter poured onto ice. The reaction mixture was extracted with diethyl ether (3×200 ml) and the organic phase was washed with water and saturated NaCl solution, dried and evaporated under a vacuum. The crude product was purified by flash chromatography with ethyl acetate/cyclohexane (1:2). A mixture of the E/Z isomers in a ratio of approx. 4:1 is obtained.

Yield: 23.7 g (95%), oil $^{13}$C-NMR (CDCl$_3$): 14.30; 25.78; 26.06; 28.15; 28.32; 28.48; 30.23; 30.48; 31.45; 31.64; 32.32; 37.57; 37.63; 38.28 (C$_4$); 41.03; 41.80; 41.96 (N(CH$_3$)$_2$); 59.62; 60.01; 74.64; 74.80; 114.12; 114.29; 117.86; 118.87; 119.94; 130.28; 132.78; 152.84; 153.46; 154.85; 160.31; 162.73; 165.91; 166.61.

3-{4-[(4-Chlorophenyl)-dimethylaminomethyl]-cyclohexyl}-acrylic acid ethyl ester 33 (R$^2$=4-chlorophenyl)

Potassium tert.-butylate (8.3 g, 0.074 mol) was added to a solution of phosphonoacetic acid triethyl ester 17 (16.59 g, 0.074 mol) in absol. DMF (120 ml) under argon and stirred for 10 min. The aldehyde 27 (13.8 g, 0.049 mol), dissolved in DMF (120 ml), was then added dropwise. The batch was stirred for 3 h at RT and thereafter poured onto ice. The reaction mixture was extracted with diethyl ether (3×100 ml) and the organic phase was washed with water and saturated NaCl solution, dried and evaporated under a vacuum. The crude product was purified by flash chromatography with ethyl acetate/cyclohexane (1:2). A mixture of the E/Z isomers in a ratio of approx. 6:1 is obtained.

Yield: 15.8 g (92%), oil $^{13}$C-NMR (CDCl$_3$): 14.22; 23.29; 25.71; 25.90; 27.99; 28.20; 28.30; 29.06; 30.07; 31.31; 31.51; 31.99; 32.20; 35.75; 37.53; 38.07; 40.61; 40.97; 41.27; 41.97; 59.69; 60.08; 70.78; 74.77; 117.98; 118.99; 120.07; 127.75; 130.46; 132.48; 134.45; 135.79; 153.10; 153.73; 155.13; 166.96.

3-[4-(1-Dimethylamino-3-phenylpropyl)-cyclohexyl]-acrylic acid ethyl ester 34 (R$^2$ phenethyl)

Potassium tert.-butylate (13.46 g, 0.120 mol) was added to a solution of phosphonoacetic acid triethyl ester 17 (26.9 g, 0.120 mol) in absol. DMF (150 ml) under argon and stirred for 10 min. The aldehyde 28 (21.34 g, 0.080 mol), dissolved in DMF (225 ml), was then added dropwise. The batch was stirred for 3 h at RT and thereafter poured onto ice. The reaction mixture was extracted with diethyl ether (3×200 ml) and the organic phase was washed with water and saturated NaCl solution, dried and evaporated under a vacuum. The crude product was purified by flash chromatography with ethyl acetate/cyclohexane (1:2).

Yield: 19.1 g (71%), oil $^{13}$C-NMR (CDCl$_3$): 14.14; 28.99; 29.53; 30.56; 31.53; 31.59; 35.26; 39.26; 40.46; 40.72; 41.09; 41.03 (N(CH$_3$)$_2$); 59.95; 68.01; 118.84; 125.54; 128.14; 128.17; 142.70; 153.83; 166.86.

3-[4-(Dimethylamino-thiophen-2-yl-methyl)-cyclohexyl]-acrylic acid ethyl ester 35 (R$^2$=2-thiophenyl)

Potassium tert.-butylate (10.3 g, 0.092 mol) was added to a solution of phosphonoacetic acid triethyl ester 17 (20.63 g, 0.092 mol) in absol. DMF (200 ml) under argon and stirred for 10 min. The aldehyde 29 (15.3, 0.061 mol), dissolved in DMF (200 ml), was then added dropwise. The batch was stirred for 3 h at RT and thereafter poured onto ice. The reaction mixture was extracted with diethyl ether (3×200 ml), the organic phase was washed with water and saturated NaCl solution, dried and evaporated under a vacuum. The crude product was purified by flash chromatography with ethyl acetate/cyclohexane (1:2).

Yield: 17.4 g (89%), oil $^{13}$C-NMR (CDCl$_3$): 14.23; 26.01; 26.39; 27.86; 28.04; 29.41; 30.23; 31.34; 31.39; 32.03; 32.08; 37.48; 37.84; 38.05; 40.11; 40.65; 40.74; 40.90; 41.28; 60.09; 70.01; 118.00; 118.99; 119.94; 123.74; 123.80; 126.02; 126.36; 139.88; 140.01; 153.30; 153.84; 155.22; 166.99.

Synthesis of the Cyclohexylacetic Esters

The cyclohexylacetic esters were synthesised from the corresponding cyclohexylideneacetic esters by hydrogenation in the presence of Pd/C.

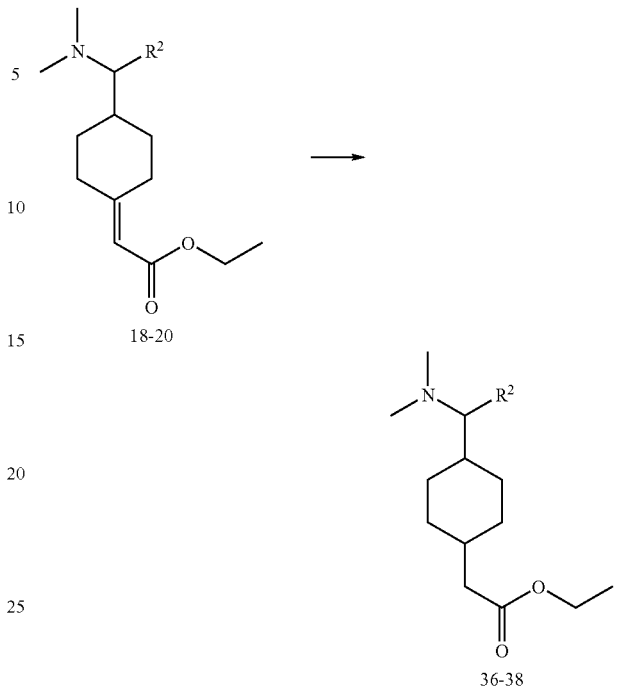

[4-(Dimethylaminophenylmethyl)-cyclohexyl]-acetic acid ethyl ester 36 (n=0; R$^2$ phenyl)

The cyclohexylideneacetic ester 18 (16.4 g, 0.0544 mol) was dissolved in methanol (200 ml), combined with 10% strength palladium/carbon (1.64 g) and hydrogenated for 24 h at 3 bar (RT). The Pd/C was removed by suction filtration through diatomaceous earth and the solvent removed under a vacuum. The residue was dissolved in 1N NaOH (100 ml) and EA (100 ml), the organic phase separated, washed with water, dried and evaporated. A mixture of the diastereomers in a ratio of approx. 3:2 is obtained.

Yield: 15.73 g (95%), colorless oil $^{13}$C-NMR (CDCl$_3$): 14.22; 25.41; 25.77; 28.71; 28.88; 30.69; 32.17; 32.84; 35.08; 35.75; 38.26; 38.94; 41.20; 41.98; 42.04 (N(CH$_3$)$_2$); 60.01; 71.53; 75.48; 126.73; 126.78; 127.49; 127.57; 129.08; 129.31; 136.23; 137.31; 172.79; 173.30.

{4-[Dimethylamino-(3-fluorophenyl)-methyl]-cyclohexyl}-acetic acid ethyl ester 37 (n=0; R$^2$=3-fluorophenyl)

The cyclohexylideneacetic ester 19 (17.5 g, 0.054 mol) was dissolved in methanol (200 ml), combined with 10% strength palladium/carbon (1.75 g) and hydrogenated for 24 h at 3 bar (RT). The Pd/C was removed by suction filtration through diatomaceous earth and the solvent removed under a vacuum. The residue was dissolved in 1N NaOH (100 ml) and EA (100 ml), the organic phase separated, washed with water, dried and evaporated. A mixture of the diastereomers in a ratio of approx. 2:1 is obtained.

Yield: 15.5 g (90%), colorless oil $^{13}$C-NMR (CDCl$_3$): 14.37; 25.39; 25.82; 28.85; 30.74; 32.23; 32.72; 32.91; 35.17; 38.45; 39.00; 41.27; 41.68; 42.04 (N(CH$_3$)$_2$); 60.04; 71.24; 75.11; 113.37; 113.42; 113.58; 113.63; 115.55; 115.76; 124.89; 128.65; 128.74; 128.82; 139.12; 139.18; 140.18; 140.24; 161.09; 163.51; 172.64; 172.93.

{4-[Dimethylamino-(4-fluorophenyl)-methyl]-cyclohexyl}-acetic acid ethyl ester 38 (n=0; R²=4-fluorophenyl)

The cyclohexylideneacetic ester 20 (14.0 g, 0.044 mol) was dissolved in methanol (200 ml), combined with 10% strength palladium/carbon (1.4 g) and hydrogenated for 24 h at 3 bar (RT). The Pd/C was removed by suction filtration through diatomaceous earth and the solvent removed under a vacuum. The residue was dissolved in 1N NaOH (100 ml) and EA (100 ml), the organic phase separated, washed with water, dried and evaporated. A mixture of the diastereomers in a ratio of approx. 3:2 is obtained.

Yield: 136 g (96%), colorless oil $^{13}$C-NMR (CDCl$_3$): 14.19; 25.17; 25.72; 28.64; 28.76; 30.65; 32.06; 32.58; 32.77; 35.02; 35.99; 38.39; 38.83; 41.14; 41.93; 59.98; 70.82; 74.70; 114.15; 114.24; 114.43; 130.44; 130.54; 132.00; 133.05; 133.09; 160.10; 163.64; 172.90; 173.19.

Synthesis of the Cyclohexylpropionic Acid Esters

The described cyclohexylpropionic acid esters were synthesised from the corresponding cyclohexylacrylic acid esters by hydrogenation in the presence of Pd/C.

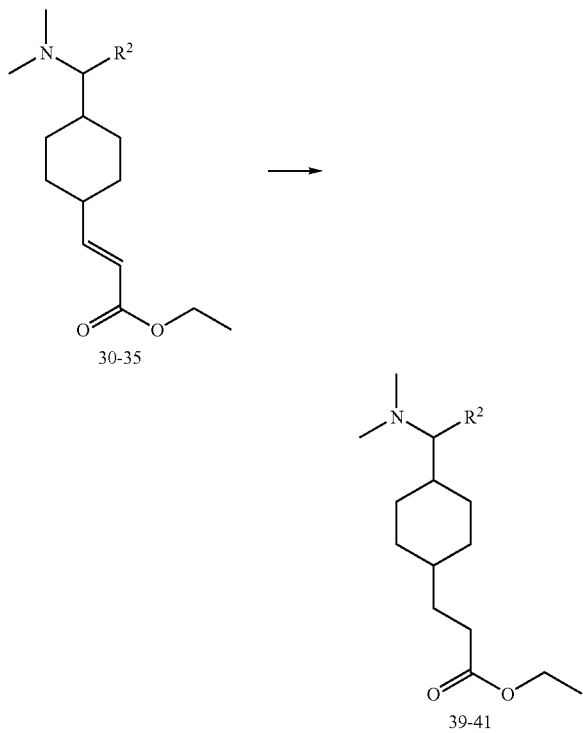

3-[4-(Dimethylaminophenylmethyl)-cyclohexyl]-propionic acid ethyl ester 39 (n=1; R²=phenyl)

The cyclohexylacrylic acid ester 30 (20.9 g, 0.066 mol) was dissolved in methanol (150 ml), combined with 10% strength palladium/carbon (2.0 g) and hydrogenated for 24 h at 3 bar (RT). The Pd/C was removed by suction filtration through diatomaceous earth and the solvent removed under a vacuum. The residue was dissolved in 1N NaOH (100 ml) and EA (100 ml), the organic phase separated, washed with water, dried and evaporated. A mixture of the diastereomers in a ratio of approx. 6:1 is obtained.

Yield: 18.6 g (89%), colorless oil $^{13}$C-NMR (CDCl$_3$): 14.15; 25.49; 25.79; 28.54; 29.00; 30.84; 31.62; 31.91; 32.15; 32.35; 32.59; 32.76; 34.62; 35.80; 37.18; 37.37; 38.57; 41.14; 41.96; 60.05; 71.33; 75.55; 126.65; 127.43; 127.50; 127.95; 129.06; 129.27; 136.25; 137.40; 173.97.

3-{4-[Dimethylamino-(3-fluorophenyl)-methyl]-cyclohexyl}-propionic acid ethyl ester 40 (n=1; R²=3-fluorophenyl)

The cyclohexylacrylic acid ester 31 (14.98 g, 0.045 mol) was dissolved in methanol (100 ml), combined with 10% strength palladium/carbon (1.5 g) and hydrogenated for 24 h at 3 bar (RT). The Pd/C was removed by suction filtration through diatomaceous earth and the solvent removed under a vacuum. The residue was dissolved in 1N NaOH (100 ml) and EA (100 ml), the organic phase separated, washed with water, dried and evaporated.

Yield: 14.3 g (95%), colorless oil $^{13}$C-NMR (CDCl$_3$): 14.18; 25.36; 25.72; 28.55; 28.86; 30.77; 31.94; 32.14; 32.38; 32.54; 32.73; 34.58; 35.94; 37.38; 38.64; 41.16; 41.98; 60.12; 71.08; 75.19; 113.41; 113.68; 115.64; 115.91; 125.03; 128.75; 128.86; 140.40; 160.86; 164.11; 174.02.

3-{4-[Dimethylamino-(4-fluorophenyl)-methyl]-cyclohexyl}-propionic acid ethyl ester 41 (n=1; R²=4-fluorophenyl)

The cyclohexylacrylic acid ester 32 (12.3 g, 0.050 mol) was dissolved in methanol (100 ml), combined with 10% strength palladium/carbon (1.63 g) and hydrogenated for 24 h at 3 bar (RT). The Pd/C was removed by suction filtration through diatomaceous earth and the solvent removed under a vacuum. The residue was dissolved in 1N NaOH (100 ml) and EA (100 ml), the organic phase separated, washed with water, dried and evaporated. A mixture of the diastereomers in a ratio of approx. 4:1 is obtained.

Yield: 16.7 g (100%), colorless oil $^{13}$C-NMR (CDCl$_3$): 14.32; 25.43; 25.93; 28.67; 28.72; 28.93; 31.00; 32.05; 32.50; 32.70; 32.88; 34.69; 36.26; 38.90 (C$_4$); 41.24; 42.08 (N(CH$_3$)$_2$); 60.11; 70.79 74.87; 114.08; 114.16; 114.27; 130.35; 130.43; 132.03; 133.17; 160.32; 162.74; 173.71.

3-[4-(1-Dimethylamino-3-phenylpropyl)-cyclohexyl]-propionic acid ethyl ester 42 (n=1; R²=phenethyl)

The cyclohexylacrylic acid ester 34 (14.04 g, 0.041 mol) was dissolved in methanol (100 ml), combined with 10% strength palladium/carbon (1.4 g) and hydrogenated for 48 h at 3 bar (RT). The Pd/C was removed by suction filtration through diatomaceous earth and the solvent removed under a vacuum. The residue was dissolved in 1N NaOH (100 ml) and EA (100 ml), the organic phase separated, washed with water, dried and evaporated.

Yield: 11.7 g (82%), colorless oil $^{13}$C-NMR (CDCl$_3$): 14.18; 25.68; 26.37; 28.36; 29.11; 30.01; 31.23; 31.65; 32.18; 32.50; 32.85; 32.90; 34.12; 35.37; 37.25; 38.73; 39.78; 40.84; 41.17; 60.07; 65.41; 68.25; 125.56; 128.24; 142.93; 174.01.

Synthesis of the Compounds According to the Invention

{{4-{[3-(4-Chlorobenzyl)-1,2,4-oxadiazol-5-yl]methyl}cyclohexyl}}-N,N-dimethyl(phenyl)methanamine 43 (n=0; $R^2$=phenyl; $R^1$=$CH_2$-(4-chlorophenyl))

The amide oxime 7 (0.18 g, 0.99 mmol) was dissolved in THF (3 ml) and combined with NaH (0.019 g, 0.79 mmol). The reaction mixture was stirred at 60° C. for 20 min. After cooling to room temperature, 36 (0.20 g, 0.66 mmol) dissolved in THF (1 ml) was added dropwise and refluxed for one hour. After cooling to RT, the reaction was quenched with water (1 ml) and 1 ml of NaOH (1 ml) and filtration performed through diatomaceous earth. The phases were then separated and the aqueous phase extracted twice with ether. The combined organic phases were dried over $MgSO_4$ and evaporated. The crude product was purified by flash chromatography with ethyl acetate.

{{4-{[3-(4-Methoxybenzyl)-1,2,4-oxadiazol-5-yl]methyl}cyclohexyl}}-N,N-dimethyl(phenyl)methanamine 44 (n=0; $R^2$=phenyl; $R^1$=$CH_2$-(4-methoxyphenyl))

Compound 8 (0.18 g, 0.99 mmol) was dissolved in THF (3 ml) and combined with NaH (0.019 g, 0.79 mmol). The reaction mixture was stirred at 60° C. for 20 min. After cooling to room temperature, 36 (0.20 g, 0.66 mmol) dissolved in THF (1 ml) was added dropwise and refluxed for one hour. After cooling to RT, the reaction was quenched with water (1 ml) and 1 ml of NaOH (1 ml) and filtration performed through diatomaceous earth. The phases were then separated and the aqueous phase extracted twice with ether. The combined organic phases were dried over $MgSO_4$ and evaporated. The crude product was purified by flash chromatography with ethyl acetate.

Automated Synthesis

Amide oxime solution (250 μmol, 1 ml, 0.25 M in THF) was initially introduced at RT into a dry threaded glass vial with septum cap and combined with NaH (200 μmol, 8 mg, 60% in mineral oil). The reaction solution was heated to 60° C. for 20 min and then combined with ester solution (100 μmol, 1 ml, 0.1 M in THF) The reaction solution was shaken with refluxing for 5 h in a Synthesis 1 Solid 24 unit from Heidolph. Once the reaction was complete, quenching was performed at RT with 1 ml of $H_2O$ and 1 ml of 5N NaOH and shaking continued for a further 15 min.

The syntheses were worked up using the Mettler-Toledo Myriad-Allex-System with the organic phase being removed and collected. The aqueous phase was combined twice with in each case 2 ml of $CH_2Cl_2$ and the phases separated. The combined organic phases were then evaporated in the GeneVac. In some cases, two or more isomers, in particular E/Z isomers, are obtained, the configuration of which was not determined. For this reason, isomers are hereinafter described as a more highly polar or more highly nonpolar diastereomer. Polarity was determined by RP-HPLC.

The following Examples were produced:

| No. | Name | Actual mass (ESI) |
|---|---|---|
| 45. | ((4-chlorophenyl)-{4-[3-(4-chlorophenyl)-[1,2,4]oxadiazol-5-ylmethylene]-cyclohexyl}-methyl)-dimethylamine | 442.1 [$M^+$ + 1]; 444.1; 446.1 |
| 46. | [{4-[3-(4-chlorophenyl)-[1,2,4]oxadiazol-5-ylmethylene]-cyclohexyl}-(4-fluorophenyl)-methyl]-dimethylamine (more highly polar diastereomer) | 426.0 [$M^+$ + 1]; 428.0 |
| 47. | [{4-[3-(4-chlorophenyl)-[1,2,4]oxadiazol-5-ylmethylene]-cyclohexyl}-(4-fluorophenyl)-methyl]-dimethylamine (more highly nonpolar diastereomer) | 426.0 [$M^+$ + 1]; 428.0 |
| 48. | ({4-[3-(2,3-dichlorophenyl)-[1,2,4]oxadiazol-5-ylmethylene]-cyclohexyl}-phenylmethyl)-dimethylamine (more highly polar diastereomer) | 442.0 [$M^+$ + 1]; 444.0 |
| 49. | ({4-[3-(2,3-dichlorophenyl)-[1,2,4]oxadiazol-5-ylmethylene]-cyclohexyl}-phenylmethyl)-dimethylamine (more highly nonpolar diastereomer) | 442.0 [$M^+$ + 1]; 444.0 |
| 50. | [{4-[3-(2,3-dichlorophenyl)-[1,2,4]oxadiazol-5-ylmethylene]-cyclohexyl}-(3-fluorophenyl)-methyl]-dimethylamine (more highly polar diastereomer) | 460.1 [$M^+$ + 1]; 462.0; 464.0 |
| 51. | [{4-[3-(2,3-dichlorophenyl)-[1,2,4]oxadiazol-5-ylmethylene]-cyclohexyl}-(3-fluorophenyl)-methyl]-dimethylamine (more highly nonpolar diastereomer) | 460.1 [$M^+$ + 1]; 462.0; 464.0 |
| 52. | ((4-chlorophenyl)-{4-[3-(2,3-dichlorophenyl)-[1,2,4]oxadiazol-5-ylmethylene]-cyclohexyl}-methyl)-dimethylamine (more highly polar diastereomer) | 476.0 [$M^+$ + 1]; 478.0; 480.0 |
| 53. | ((4-chlorophenyl)-{4-[3-(2,3-dichlorophenyl)-[1,2,4]oxadiazol-5-ylmethylene]-cyclohexyl}-methyl)-dimethylamine (more highly nonpolar diastereomer) | 476.0 [$M^+$ + 1]; 478.0; 480.0 |
| 54. | (1-{4-[3-(2,3-dichlorophenyl)-[1,2,4]oxadiazol-5-ylmethylene]-cyclohexyl}-3-phenylpropyl)-dimethylamine | 470.0 [$M^+$ + 1]; 472.0 |
| 55. | [{4-[3-(2,3-dichlorophenyl)-[1,2,4]oxadiazol-5-ylmethylene]-cyclohexyl}-(4-fluorophenyl)-methyl]-dimethylamine (more highly polar diastereomer) | 460.0 [$M^+$ + 1]; 462.0 |
| 56. | [{4-[3-(2,3-dichlorophenyl)-[1,2,4]oxadiazol-5-ylmethylene]-cyclohexyl}-(4-fluorophenyl)-methyl]-dimethylamine (more highly nonpolar diastereomer) | 460.0 [$M^+$ + 1]; 462.0 |

| No. | Name | Actual mass (ESI) |
|---|---|---|
| 57. | dimethyl-(phenyl-{4-[3-(4-trifluoromethoxyphenyl)-[1,2,4]oxadiazol-5-ylmethylene]-cyclohexyl}-methyl)-amine (more highly polar diastereomer) | 458.2 [M$^+$ + 1] |
| 58. | dimethyl-(phenyl-{4-[3-(4-trifluoromethoxyphenyl)-[1,2,4]oxadiazol-5-ylmethylene]-cyclohexyl}-methyl-amine (more highly nonpolar diastereomer) | 458.2 [M$^+$ + 1] |
| 59. | ((3-fluorophenyl)-{4-[3-(4-trifluoromethoxyphenyl)-[1,2,4]oxadiazol-5-ylmethylene]-cyclohexyl}-methyl)-dimethylamine (more highly polar diastereomer) | 476.2 [M$^+$ + 1] |
| 60. | ((3-fluorophenyl)-{4-[3-(4-trifluoromethoxyphenyl)-[1,2,4]oxadiazol-5-ylmethylene]-cyclohexyl}-methyl)-dimethylamine (more highly nonpolar diastereomer) | 476.2 [M$^+$ + 1] |
| 61. | ((4-chlorophenyl))-{4-[3-(4-trifluoromethoxyphenyl)-[1,2,4]oxadiazol-5-ylmethylene]-cyclohexyl}-methyl)-dimethylamine (more highly polar diastereomer) | 492.0 [M$^+$ + 1]; 494.0 |
| 62. | ((4-chlorophenyl))-{4-[3-(4-trifluoromethoxyphenyl)-[1,2,4]oxadiazol-5-ylmethylene]-cyclohexyl}-methyl)-dimethylamine (more highly nonpolar diastereomer) | 492.0 [M$^+$ + 1]; 494.0 |
| 63. | dimethyl-(3-phenyl-1-{4-[3-(4-trifluoromethoxyphenyl)-[1,2,4]oxadiazol-5-ylmethylene]-cyclohexyl}-propyl)-amine (more highly polar diastereomer) | 486.2 [M$^+$ + 1] |
| 64. | dimethyl-(3-phenyl-1-{4-[3-(4-trifluoromethoxyphenyl)-[1,2,4]oxadiazol-5-ylmethylene]-cyclohexyl}-propyl)-amine (more highly nonpolar diastereomer) | 486.2 [M$^+$ + 1] |
| 65. | ((4-fluorophenyl)-{4-[3-(4-trifluoromethoxyphenyl)-[1,2,4]oxadiazol-5-ylmethylene]-cyclohexyl}-methyl)-dimethylamine (more highly polar diastereomer) | 476.2 [M$^+$ + 1] |
| 66. | ((4-fluorophenyl)-{4-[3-(4-trifluoromethoxyphenyl)-[1,2,4]oxadiazol-5-ylmethylene]-cyclohexyl}-methyl)-dimethylamine (more highly nonpolar diastereomer) | 476.2 [M$^+$ + 1] |
| 67. | dimethyl-(thiophen-2-yl-{4-[3-(4-trifluoromethoxyphenyl)-[1,2,4]oxadiazol-5-ylmethylene]-cyclohexyl}-methyl)-amine (more highly polar diastereomer) | 464.2 [M$^+$ + 1] |
| 68. | dimethyl-(thiophen-2-yl-{4-[3-(4-trifluoromethoxyphenyl)-[1,2,4]oxadiazol-5-ylmethylene]-cyclohexyl}-methyl)-amine (more highly nonpolar diastereomer) | 464.2 [M$^+$ + 1] |
| 69. | dimethyl-{phenyl-[4-(3-phenyl-[1,2,4]oxadiazol-5-ylmethylene)-cyclohexyl]-methyl}-amine (more highly polar diastereomer) | 374.2 [M$^+$ + 1] |
| 70. | dimethyl-{phenyl-[4-(3-phenyl-[1,2,4]oxadiazol-5-ylmethylene)-cyclohexyl]-methyl}-amine (more highly nonpolar diastereomer) | 374.2 [M$^+$ + 1] |
| 71. | {(3-fluorophenyl)-[4-(3-phenyl-[1,2,4]oxadiazol-5-ylmethylene)-cyclohexyl]-methyl}-dimethylamine (more highly polar diastereomer) | 392.2 [M$^+$ + 1] |
| 72. | {(3-fluorophenyl)-[4-(3-phenyl-[1,2,4]oxadiazol-5-ylmethylene)-cyclohexyl]-methyl}-dimethylamine (more highly nonpolar diastereomer) | 392.2 [M$^+$ + 1] |
| 73. | dimethyl-{3-phenyl-1-[4-(3-phenyl-[1,2,4]oxadiazol-5-ylmethylene)-cyclohexyl]-propyl}-amine (more highly polar diastereomer) | 402.2 [M$^+$ + 1] |
| 74. | dimethyl-{3-phenyl-1-[4-(3-phenyl-[1,2,4]oxadiazol-5-ylmethylene)-cyclohexyl]-propyl}-amine (more highly nonpolar diastereomer) | 402.2 [M$^+$ + 1] |
| 75. | {(4-fluorophenyl)-[4-(3-phenyl-[1,2,4]oxadiazol-5-ylmethylene)-cyclohexyl]-methyl}-dimethylamine (more highly polar diastereomer) | 392.2 [M$^+$ + 1] |
| 76. | {(4-fluorophenyl)-[4-(3-phenyl-[1,2,4]oxadiazol-5-ylmethylene)-cyclohexyl]-methyl}-dimethylamine (more highly nonpolar diastereomer) | 392.2 [M$^+$ + 1] |
| 77. | [{4-[3-(2,4-difluorophenyl)-[1,2,4]oxadiazol-5-ylmethylene]-cyclohexyl}-(3-fluorophenyl)-methyl]-dimethylamine (more highly polar diastereomer) | 428.2 [M$^+$ + 1] |
| 78. | [{4-[3-(2,4-difluorophenyl)-[1,2,4]oxadiazol-5-ylmethylene]-cyclohexyl}-(3-fluorophenyl)-methyl]-dimethylamine (more highly nonpolar diastereomer) | 428.2 [M$^+$ + 1] |
| 79. | ({4-[3-(4-methoxybenzyl)-[1,2,4]oxadiazol-5-ylmethylene]-cyclohexyl}-phenylmethyl)-dimethylamine (more highly polar diastereomer) | 418.2 [M$^+$ + 1] |
| 80. | ({4-[3-(4-methoxybenzyl)-[1,2,4]oxadiazol-5-ylmethylene]-cyclohexyl}-phenylmethyl)-dimethylamine (more highly nonpolar diastereomer) | 418.2 [M$^+$ + 1] |
| 81. | ((3-fluorophenyl)-{4-[3-(4-methoxybenzyl)-[1,2,4]oxadiazol-5-ylmethylene]-cyclohexyl}-methyl)-dimethylamine (more highly polar diastereomer) | 436.2 [M$^+$ + 1] |
| 82. | ((3-fluorophenyl)-{4-[3-(4-methoxybenzyl)-[1,2,4]oxadiazol-5-ylmethylene]-cyclohexyl}-methyl)-dimethylamine (more highly nonpolar diastereomer) | 436.2 [M$^+$ + 1] |
| 83. | ((4-chlorophenyl)-{4-[3-(4-methoxybenzyl)-[1,2,4]oxadiazol-5-ylmethylene]-cyclohexyl}-methyl)-dimethylamine (more highly polar diastereomer) | 452.0 [M$^+$ + 1]; 454.0 |

| No. | Name | Actual mass (ESI) |
|---|---|---|
| 84. | ((4-chlorophenyl)-{4-[3-(4-methoxybenzyl)-[1,2,4]oxadiazol-5-ylmethylene]-cyclohexyl}-methyl)-dimethylamine (more highly nonpolar diastereomer) | 452.0 [M$^+$ + 1]; 454.0 |
| 85. | (1-{4-[3-(4-methoxybenzyl)-[1,2,4]oxadiazol-5-ylmethylene]-cyclohexyl}-3-phenylpropyl)-dimethylamine (more highly polar diastereomer) | 446.3 [M$^+$ + 1] |
| 86. | (1-{4-[3-(4-methoxybenzyl)-[1,2,4]oxadiazol-5-ylmethylene]-cyclohexyl}-3-phenylpropyl)-dimethylamine (more highly nonpolar diastereomer) | 446.3 [M$^+$ + 1] |
| 87. | ((4-fluorophenyl)-{4-[3-(4-methoxybenzyl)-[1,2,4]oxadiazol-5-ylmethylene]-cyclohexyl}-methyl)-dimethylamine (more highly polar diastereomer) | 436.2 [M$^+$ + 1] |
| 88. | ((4-fluorophenyl)-{4-[3-(4-methoxybenzyl)-[1,2,4]oxadiazol-5-ylmethylene]-cyclohexyl}-methyl)-dimethylamine (more highly nonpolar diastereomer) | 436.2 [M$^+$ + 1] |
| 89. | ({4-[3-(4-chlorobenzyl)-[1,2,4]oxadiazol-5-ylmethylene-cyclohexyl}-phenylmethyl)-dimethylamine (more highly polar diastereomer) | 422.1 [M$^+$ + 1]; 424.0 |
| 90. | ({4-[3-(4-chlorobenzyl)-[1,2,4]oxadiazol-5-ylmethylene-cyclohexyl}-phenylmethyl)-dimethylamine (more highly nonpolar diastereomer) | 422.1 [M$^+$ + 1]; 424.0 |
| 91. | [{4-[3-(4-chlorobenzyl)-[1,2,4]oxadiazol-5-ylmethylene-cyclohexyl}-(3-fluorophenyl)-methyl]-dimethylamine (more highly polar diastereomer) | 440.0 [M$^+$ + 1]; 442.0 |
| 92. | [{4-[3-(4-chlorobenzyl)-[1,2,4]oxadiazol-5-ylmethylene-cyclohexyl}-(3-fluorophenyl)-methyl]-dimethylamine (more highly nonpolar diastereomer) | 440.0 [M$^+$ + 1]; 442.0 |
| 93. | [{4-[3-(4-chlorobenzyl)-[1,2,4]oxadiazol-5-ylmethylene-cyclohexyl}-(4-chlorophenyl)-methyl]-dimethylamine (more highly polar diastereomer) | 456.0 [M$^+$ + 1]; 458.0 |
| 94. | [{4-[3-(4-chlorobenzyl)-[1,2,4]oxadiazol-5-ylmethylene-cyclohexyl}-(4-chlorophenyl)-methyl]-dimethylamine (more highly nonpolar diastereomer) | 456.0 [M$^+$ + 1]; 458.0 |
| 95. | (1-{4-[3-(4-chlorobenzyl)-[1,2,4]oxadiazol-5-ylmethylene]-cyclohexyl}-3-phenylpropyl)-dimethylamine (more highly polar diastereomer) | 450.0 [M$^+$ + 1]; 452.0 |
| 96. | (1-{4-[3-(4-chlorobenzyl)-[1,2,4]oxadiazol-5-ylmethylene]-cyclohexyl}-3-phenylpropyl)-dimethylamine (more highly nonpolar diastereomer) | 450.0 [M$^+$ + 1]; 452.0 |
| 97. | [{4-[3-(4-chlorobenzyl)-[1,2,4]oxadiazol-5-ylmethylene-cyclohexyl}-(4-fluorophenyl)-methyl]-dimethylamine (more highly polar diastereomer) | 440.0 [M$^+$ + 1]; 442.0 |
| 98. | [{4-[3-(4-chlorobenzyl)-[1,2,4]oxadiazol-5-ylmethylene-cyclohexyl}-(4-fluorophenyl)-methyl]-dimethylamine (more highly nonpolar diastereomer) | 440.0 [M$^+$ + 1]; 442.0 |
| 99. | {(3-fluorophenyl)-[4-(3-p-tolyl-[1,2,4]oxadiazol-5-ylmethylene)-cyclohexyl]-methyl}-dimethylamine | 406.2 [M$^+$ + 1] |
| 100. | {(4-chlorophenyl)-[4-(3-p-tolyl-[1,2,4]oxadiazol-5-ylmethylene)-cyclohexyl]-methyl}-dimethylamine | 422.0 [M$^+$ + 1]; 424.0 |
| 101. | {(4-fluorophenyl)-[4-(3-p-tolyl-[1,2,4]oxadiazol-5-ylmethylene)-cyclohexyl]-methyl}-dimethylamine (more highly polar diastereomer) | 406.2 [M$^+$ + 1] |
| 102. | {(4-fluorophenyl)-[4-(3-p-tolyl-[1,2,4]oxadiazol-5-ylmethylene)-cyclohexyl]-methyl}-dimethylamine (more highly nonpolar diastereomer) | 406.2 [M$^+$ + 1] |
| 103. | ({4-[3-(3,4-dimethoxyphenyl)-[1,2,4]oxadiazol-5-ylmethylene]-cyclohexyl}-phenylmethyl)-dimethylamine (more highly polar diastereomer) | 434.2 [M$^+$ + 1] |
| 104. | ({4-[3-(3,4-dimethoxyphenyl)-[1,2,4]oxadiazol-5-ylmethylene]-cyclohexyl}-phenylmethyl)-dimethylamine (more highly nonpolar diastereomer) | 434.2 [M$^+$ + 1] |
| 105. | [{4-[3-(3,4-dimethoxyphenyl)-[1,2,4]oxadiazol-5-ylmethylene]-cyclohexyl}-(3-fluorophenyl)-methyl]-dimethylamine (more highly polar diastereomer) | 452.2 [M$^+$ + 1] |
| 106. | [{4-[3-(3,4-dimethoxyphenyl)-[1,2,4]oxadiazol-5-ylmethylene]-cyclohexyl}-(3-fluorophenyl)-methyl]-dimethylamine (more highly nonpolar diastereomer) | 452.2 [M$^+$ + 1] |
| 107. | ((4-chlorophenyl)-{4-[3-(3,4-dimethoxyphenyl)-[1,2,4]oxadiazol-5-ylmethylene]-cyclohexyl}-methyl)-dimethylamine (more highly polar diastereomer) | 468.0 [M$^+$ + 1]; 470.0 |
| 108. | ((4-chlorophenyl)-{4-[3-(3,4-dimethoxyphenyl)-[1,2,4]oxadiazol-5-ylmethylene]-cyclohexyl}-methyl)-dimethylamine (more highly nonpolar diastereomer) | 468.0 [M$^+$ + 1]; 470.0 |
| 109. | (1-{4-[3-(3,4-dimethoxyphenyl)-[1,2,4]oxadiazol-5-ylmethylene]-cyclohexyl}-3-phenylpropyl)-dimethylamine (more highly polar diastereomer) | 462.3 |
| 110. | (1-{4-[3-(3,4-dimethoxyphenyl)-[1,2,4]oxadiazol-5-ylmethylene]-cyclohexyl}-3-phenylpropyl)-dimethylamine (more highly nonpolar diastereomer) | 462.3 [M$^+$ + 1] |

| No. | Name | Actual mass (ESI) |
|---|---|---|
| 111. | [{4-[3-(3,4-dimethoxyphenyl)-[1,2,4]oxadiazol-5-ylmethylene]-cyclohexyl}-(4-fluorophenyl)-methyl]-dimethylamine (more highly polar diastereomer) | 452.2 [M$^+$ + 1] |
| 112. | [{4-[3-(3,4-dimethoxyphenyl)-[1,2,4]oxadiazol-5-ylmethylene]-cyclohexyl}-(4-fluorophenyl)-methyl]-dimethylamine (more highly nonpolar diastereomer) | 452.2 [M$^+$ + 1] |
| 113. | ({4-[3-(3-chlorophenyl)-[1,2,4]oxadiazol-5-ylmethylene]-cyclohexyl}-phenylmethyl)-dimethylamine (more highly polar diastereomer) | 408.0 [M$^+$ + 1]; 410.0 |
| 114. | ({4-[3-(3-chlorophenyl)-[1,2,4]oxadiazol-5-ylmethylene]-cyclohexyl}-phenylmethyl)-dimethylamine (more highly nonpolar diastereomer) | 408.0 [M$^+$ + 1]; 410.0 |
| 115. | [{4-[3-(3-chlorophenyl)-[1,2,4]oxadiazol-5-ylmethylene]-cyclohexyl}-(3-fluorophenyl)-methyl]-dimethylamine (more highly polar diastereomer) | 426.0 [M$^+$ + 1]; 428.0 |
| 116. | [{4-[3-(3-chlorophenyl)-[1,2,4]oxadiazol-5-ylmethylene]-cyclohexyl}-(3-fluorophenyl)-methyl]-dimethylamine (more highly nonpolar diastereomer) | 426.0 [M$^+$ + 1]; 428.0 |
| 117. | ((4-chlorophenyl)-{4-[3-(3-chlorophenyl)-[1,2,4]oxadiazol-5-ylmethylene]-cyclohexyl}-methyl)-dimethylamine (more highly polar diastereomer) | 442.0 [M$^+$ + 1]; 444.0 |
| 118. | ((4-chlorophenyl)-{4-[3-(3-chlorophenyl)-[1,2,4]oxadiazol-5-ylmethylene]-cyclohexyl}-methyl)-dimethylamine (more highly nonpolar diastereomer) | 442.0 [M$^+$ + 1]; 444.0 |
| 119. | (1-{4-[3-(3-chlorophenyl)-[1,2,4]oxadiazol-5-ylmethylene]-cyclohexyl}-3-phenylpropyl)-dimethylamine (more highly polar diastereomer) | 436.0 [M$^+$ + 1]; 438.0 |
| 120. | (1-{4-[3-(3-chlorophenyl)-[1,2,4]oxadiazol-5-ylmethylene]-cyclohexyl}-3-phenylpropyl)-dimethylamine (more highly nonpolar diastereomer) | 436.0 [M$^+$ + 1]; 438.0 |
| 121. | [{4-[3-(3-chlorophenyl)-[1,2,4]oxadiazol-5-ylmethylene]-cyclohexyl}-(4-fluorophenyl)-methyl]-dimethylamine | 426.0 [M$^+$ + 1]; 428.0 |
| 122. | ({4-[3-(4-tert.-butylphenyl)-[1,2,4]oxadiazol-5-ylmethylene]-cyclohexyl}-phenylmethyl)-dimethylamine (more highly polar diastereomer) | 430.3 [M$^+$ + 1] |
| 123. | ({4-[3-(4-tert.-butylphenyl)-[1,2,4]oxadiazol-5-ylmethylene]-cyclohexyl}-phenylmethyl)-dimethylamine (more highly nonpolar diastereomer) | 430.3 [M$^+$ + 1] |
| 124. | [{4-[3-(4-tert.-butylphenyl)-[1,2,4]oxadiazol-5-ylmethylene]-cyclohexyl}-(3-fluorophenyl)-methyl]-dimethylamine (more highly polar diastereomer) | 448.3 [M$^+$ + 1] |
| 125. | [{4-[3-(4-tert.-butylphenyl)-[1,2,4]oxadiazol-5-ylmethylene]-cyclohexyl}-(3-fluorophenyl)-methyl]-dimethylamine (more highly nonpolar diastereomer) | 448.3 [M$^+$ + 1] |
| 126. | [{4-[3-(4-tert.-butylphenyl)-[1,2,4]oxadiazol-5-ylmethylene]-cyclohexyl}-(4-chlorophenyl)-methyl]-dimethylamine (more highly polar diastereomer) | 464.1 [M$^+$ + 1]; 466.1 |
| 127. | [{4-[3-(4-tert.-butylphenyl)-[1,2,4]oxadiazol-5-ylmethylene]-cyclohexyl}-(4-chlorophenyl)-methyl]-dimethylamine (more highly nonpolar diastereomer) | 464.1 [M$^+$ + 1]; 466.1 |
| 128. | [1-{4-[3-(4-tert.-butylphenyl)-[1,2,4]oxadiazol-5-ylmethylene]-cyclohexyl}-3-phenylpropyl)-dimethylamine (more highly polar diastereomer) | 458.3 [M$^+$ + 1] |
| 129. | (1-{4-[3-(4-tert.-butylphenyl)-[1,2,4]oxadiazol-5-ylmethylene]-cyclohexyl}-3-phenylpropyl)-dimethylamine (more highly nonpolar diastereomer) | 458.3 [M$^+$ + 1] |
| 130. | [{4-[3-(4-tert.-butylphenyl)-[1,2,4]oxadiazol-5-ylmethylene]-cyclohexyl}-(4-fluorophenyl)-methyl]-dimethylamine (more highly polar diastereomer) | 448.3 [M$^+$ + 1] |
| 131. | [{4-[3-(4-tert.-butylphenyl)-[1,2,4]oxadiazol-5-ylmethylene]-cyclohexyl}-(4-fluorophenyl)-methyl]-dimethylamine (more highly nonpolar diastereomer) | 448.3 [M$^+$ + 1] |
| 132. | ({4-[3-(4-tert.-butylphenyl)-[1,2,4]oxadiazol-5-ylmethylene]-cyclohexyl}-thiophen-2-yl-methyl)-dimethylamine (more highly polar diastereomer) | 436.2 [M$^+$ + 1] |
| 133. | ({4-[3-(4-tert.-butylphenyl)-[1,2,4]oxadiazol-5-ylmethylene]-cyclohexyl}-thiophen-2-yl-methyl)-dimethylamine (more highly nonpolar diastereomer) | 436.2 [M$^+$ + 1] |
| 134. | dimethyl-{phenyl-[4-(3-m-tolyl-[1,2,4]oxadiazol-5-ylmethylene)-cyclohexyl]-methyl}-amine (more highly polar diastereomer) | 388.2 [M$^+$ + 1] |
| 135. | dimethyl-{phenyl-[4-(3-m-tolyl-[1,2,4]oxadiazol-5-ylmethylene)-cyclohexyl]-methyl}-amine (more highly nonpolar diastereomer) | 388.2 [M$^+$ + 1] |
| 136. | {(3-fluorophenyl)-[4-(3-m-tolyl-[1,2,4]oxadiazol-5-ylmethylene)-cyclohexyl]-methyl}-dimethylamine (more highly polar diastereomer) | 406.2 [M$^+$ + 1] |
| 137. | {(3-fluorophenyl)-[4-(3-m-tolyl-[1,2,4]oxadiazol-5-ylmethylene)-cyclohexyl]-methyl}-dimethylamine (more highly nonpolar diastereomer) | 406.2 [M$^+$ + 1] |

-continued

| No. | Name | Actual mass (ESI) |
|---|---|---|
| 138. | {(4-chlorophenyl)-[4-(3-m-tolyl-[1,2,4]oxadiazol-5-ylmethylene)-cyclohexyl]-methyl}-dimethylamine (more highly polar diastereomer) | 422.1 [M$^+$ + 1]; 424.0 |
| 139. | {(4-chlorophenyl)-[4-(3-m-tolyl-[1,2,4]oxadiazol-5-ylmethylene)-cyclohexyl]-methyl}-dimethylamine (more highly nonpolar diastereomer) | 422.1 [M$^+$ + 1]; 424.0 |
| 140. | ((4-fluorophenyl)-{4-[2-(3-phenyl-[1,2,4]oxadiazol-5-yl)-vinyl]-cyclohexyl}-methyl)-dimethylamine | 406.2 [M$^+$ + 1] |
| 141. | [(4-{2-[3-(2,4-difluorophenyl)-[1,2,4]oxadiazol-5-yl]-vinyl}-cyclohexyl)-(4-fluorophenyl)-methyl]-dimethylamine | 442.2 [M$^+$ + 1] |
| 142. | [(4-fluorophenyl)-(4-{2-[3-(4-methoxybenzyl)-[1,2,4]oxadiazol-5-yl]-vinyl}-cyclohexyl)-methyl]-dimethylamine | 450.2 [M$^+$ + 1] |
| 143. | [(4-{2-[3-(4-chlorobenzyl)-[1,2,4]oxadiazol-5-yl]-vinyl}-cyclohexyl)-(4-fluorophenyl)-methyl]-dimethylamine | 454.1 [M$^+$ + 1]; 456.0 |
| 144. | dimethyl-(3-phenyl-1-{4-[2-(3-phenyl-[1,2,4]oxadiazol-5-yl)-vinyl]-cyclohexyl}-propyl)-amine | 416.3 [M$^+$ + 1] |
| 145. | [1-(4-{2-[3-(2,4-difluorophenyl)-[1,2,4]oxadiazol-5-yl]-vinyl}-cyclohexyl)-3-phenylpropyl]-dimethylamine | 452.2 [M$^+$ + 1] |
| 146. | [1-(4-{2-[3-(4-methoxybenzyl)-[1,2,4]oxadiazol-5-yl]-vinyl}-cyclohexyl)-3-phenylpropyl]-dimethylamine | 460.3 [M$^+$ + 1] |
| 147. | [1-(4-{2-[3-(4-chlorobenzyl)-[1,2,4]oxadiazol-5-yl]-vinyl}-cyclohexyl)-3-phenylpropyl]-dimethylamine | 464.1 [M$^+$ + 1]; 466.0 |
| 148. | dimethyl-(phenyl-{4-[2-(3-phenyl-[1,2,4]oxadiazol-5-yl)-vinyl]-cyclohexyl}-methyl)-amine | 388.2 [M$^+$ + 1] |
| 149. | [(4-{2-[3-(4-chlorobenzyl)-[1,2,4]oxadiazol-5-yl]-vinyl}-cyclohexyl)-phenylmethyl]-dimethylamine (more highly polar diastereomer) | 436.1 [M$^+$ + 1]; 438.0 |
| 150. | [(4-{2-[3-(4-chlorobenzyl)-[1,2,4]oxadiazol-5-yl]-vinyl}-cyclohexyl)-phenylmethyl]-dimethylamine (more highly nonpolar diastereomer) | 436.1 [M$^+$ + 1]; 438.0 |
| 151. | [(4-chlorophenyl)-(4-{2-[3-(2,4-difluorophenyl)-[1,2,4]oxadiazol-5-yl]-vinyl}-cyclohexyl)-methyl]-dimethylamine | 458.1 [M$^+$ + 1]; 460.0 |
| 152. | [(4-chlorophenyl)-(4-{2-[3-(4-methoxybenzyl)-[1,2,4]oxadiazol-5-yl]-vinyl}-cyclohexyl)-methyl]-dimethylamine | 466.1 [M$^+$ + 1]; 468.0 |
| 153. | [(4-{2-[3-(4-chlorobenzyl)-[1,2,4]oxadiazol-5-yl]-vinyl}-cyclohexyl)-(4-chlorophenyl)-methyl]-dimethylamine | 470.0 [M$^+$ + 1]; 472.0 |
| 154. | [(4-{2-[3-(4-methoxybenzyl)-[1,2,4]oxadiazol-5-yl]-vinyl}-cyclohexyl)-thiophen-2-yl-methyl]-dimethylamine | 438.2 [M$^+$ + 1] |
| 155. | [(4-{2-[3-(4-chlorobenzyl)-[1,2,4]oxadiazol-5-yl]-vinyl}-cyclohexyl)-thiophen-2-yl-methyl]-dimethylamine | 442.1 [M$^+$ + 1]; 444.0 |
| 156. | ((3-fluorophenyl)-{4-[2-(3-phenyl-[1,2,4]oxadiazol-5-yl)-vinyl]-cyclohexyl}-methyl)-dimethylamine | 406.2 [M$^+$ + 1] |
| 157. | [(3-fluorophenyl)-(4-{2-[3-(4-methoxybenzyl)-[1,2,4]oxadiazol-5-yl]-vinyl}-cyclohexyl)-methyl]-dimethylamine | 450.2 [M$^+$ + 1] |
| 158. | ((4-fluorophenyl)-{4-[2-(3-p-tolyl-[1,2,4]oxadiazol-5-yl)-vinyl]-cyclohexyl}-methyl)-dimethylamine | 420.2 [M$^+$ + 1] |
| 159. | [(4-{2-[3-(3,4-dimethoxyphenyl)-[1,2,4]oxadiazol-5-yl]-vinyl}-cyclohexyl)-(4-fluorophenyl)-methyl]-dimethylamine | 466.2 [M$^+$ + 1] |
| 160. | dimethyl-(3-phenyl-1-{4-[2-(3-p-tolyl-[1,2,4]oxadiazol-5-yl)-vinyl]-cyclohexyl}-propyl)-amine | 430.3 [M$^+$ + 1] |
| 161. | [1-(4-{2-[3-(3,4-dimethoxyphenyl)-[1,2,4]oxadiazol-5-yl]-vinyl}-cyclohexyl)-3-phenylpropyl]-dimethylamine | 476.3 [M$^+$ + 1] |
| 162. | dimethyl-(phenyl-{4-[2-(3-p-tolyl-[1,2,4]oxadiazol-5-yl)-vinyl]-cyclohexyl}-methyl)-amine | 402.2 [M$^+$ + 1] |
| 163. | [(4-{2-[3-(3,4-dimethoxyphenyl)-[1,2,4]oxadiazol-5-yl]-vinyl}-cyclohexyl)-phenylmethyl]-dimethylamine | 448.3 [M$^+$ + 1] |
| 164. | ((4-chlorophenyl)-{4-[2-(3-p-tolyl-[1,2,4]oxadiazol-5-yl)-vinyl]-cyclohexyl}-methyl)-dimethylamine | 436.1 [M$^+$ + 1]; 438.0 |
| 165. | [(4-chlorophenyl)-(4-{2-[3-(3,4-dimethoxyphenyl)-[1,2,4]oxadiazol-5-yl]-vinyl}-cyclohexyl)-methyl]-dimethylamine | 482.0 [M$^+$ + 1]; 484.1 |
| 166. | dimethyl-(thiophen-2-yl-{4-[2-(3-p-tolyl-[1,2,4]oxadiazol-5-yl)-vinyl]-cyclohexyl}-methyl)-amine | 408.2 [M$^+$ + 1] |
| 167. | [(4-{2-[3-(3,4-dimethoxyphenyl)-[1,2,4]oxadiazol-5-yl]-vinyl}-cyclohexyl)-thiophen-2-yl-methyl]-dimethylamine | 454.2 [M$^+$ + 1] |
| 168. | ((3-fluorophenyl)-{4-[2-(3-p-tolyl-[1,2,4]oxadiazol-5-yl)-vinyl]-cyclohexyl}-methyl)-dimethylamine | 420.2 [M$^+$ + 1] |
| 169. | [(4-{2-[3-(3,4-dimethoxyphenyl)-[1,2,4]oxadiazol-5-yl]-vinyl}-cyclohexyl)-(3-fluorophenyl)-methyl]-dimethylamine | 466.2 [M$^+$ + 1] |
| 170. | [(4-{2-[3-(3-chlorophenyl)-[1,2,4]oxadiazol-5-yl]-vinyl}-cyclohexyl)-(4-fluorophenyl)-methyl]-dimethylamine | 440.0 [M$^+$ + 1]; 442.0 |
| 171. | [(4-{2-[3-(4-tert.-butylphenyl)-[1,2,4]oxadiazol-5-yl]-vinyl}-cyclohexyl)-(4-fluorophenyl)-methyl]-dimethylamine | 462.3 [M$^+$ + 1] |
| 172. | [(4-{2-[3-(4-tert.-butylphenyl)-[1,2,4]oxadiazol-5-yl]-vinyl}-cyclohexyl)-(4-fluorophenyl)-methyl]-dimethylamine | 462.3 [M$^+$ + 1] |
| 173. | ((4-fluorophenyl)-{4-[2-(3-m-tolyl-[1,2,4]oxadiazol-5-yl)-vinyl]-cyclohexyl}-methyl)-dimethylamine | 420.2 [M$^+$ + 1] |
| 174. | [1-(4-{2-[3-(3-chlorophenyl)-[1,2,4]oxadiazol-5-yl]-vinyl}-cyclohexyl)-3-phenylpropyl]-dimethylamine | 450.1 [M$^+$ + 1]; 452.0 |

-continued

| No. | Name | Actual mass (ESI) |
|---|---|---|
| 175. | [1-(4-{2-[3-(4-tert.-butylphenyl)-[1,2,4]oxadiazol-5-yl]-vinyl}-cyclohexyl)-3-phenylpropyl]-dimethylamine (more highly polar diastereomer) | 472.3 [M$^+$ + 1] |
| 176. | [1-(4-{2-[3-(4-tert.-butylphenyl)-[1,2,4]oxadiazol-5-yl]-vinyl}-cyclohexyl)-3-phenylpropyl]-dimethylamine (more highly nonpolar diastereomer) | 472.3 [M$^+$ + 1] |
| 177. | dimethyl-(3-phenyl-1-{4-[2-(3-m-tolyl-[1,2,4]oxadiazol-5-yl)-vinyl]-cyclohexyl}-propyl)-amine (more highly polar diastereomer) | 430.3 [M$^+$ + 1] |
| 178. | dimethyl-(3-phenyl-1-{4-[2-(3-m-tolyl-[1,2,4]oxadiazol-5-yl)-vinyl]-cyclohexyl}-propyl)-amine (more highly nonpolar diastereomer) | 430.3 [M$^+$ + 1] |
| 179. | [(4-{2-[3-(3-chlorophenyl)-[1,2,4]oxadiazol-5-yl]-vinyl}-cyclohexyl)-phenylmethyl]-dimethylamine | 422.1 [M$^+$ + 1]; 424.0 |
| 180. | [(4-{2-[3-(4-tert.-butylphenyl)-[1,2,4]oxadiazol-5-yl]-vinyl}-cyclohexyl)-phenylmethyl]-dimethylamine (more highly polar diastereomer) | 444.3 [M$^+$ + 1] |
| 181. | [(4-{2-[3-(4-tert.-butylphenyl)-[1,2,4]oxadiazol-5-yl]-vinyl}-cyclohexyl)-phenylmethyl]-dimethylamine (more highly nonpolar diastereomer) | 444.3 [M$^+$ + 1] |
| 182. | dimethyl-(phenyl-{4-[2-(3-m-tolyl-[1,2,4]oxadiazol-5-yl)-vinyl]-cyclohexyl}-methyl)-amine (more highly polar diastereomer) | 402.2 [M$^+$ + 1] |
| 183. | dimethyl-(phenyl-{4-[2-(3-m-tolyl-[1,2,4]oxadiazol-5-yl)-vinyl]-cyclohexyl}-methyl)-amine (more highly nonpolar diastereomer) | 402.2 [M$^+$ + 1] |
| 184. | [(4-{2-[3-(4-chlorophenyl)-[1,2,4]oxadiazol-5-yl]-vinyl}-cyclohexyl)-phenylmethyl]-dimethylamine (more highly polar diastereomer) | 422.1 [M$^+$ + 1]; 424.0 |
| 185. | [(4-{2-[3-(4-chlorophenyl)-[1,2,4]oxadiazol-5-yl]-vinyl}-cyclohexyl)-phenylmethyl]-dimethylamine (more highly nonpolar diastereomer) | 422.1 [M$^+$ + 1]; 424.0 |
| 186. | [(4-chlorophenyl)-(4-{2-[3-(3-chlorophenyl)-[1,2,4]oxadiazol-5-yl]-vinyl}-cyclohexyl)-methyl]-dimethylamine | 456.1 [M$^+$ + 1]; 458.0 |
| 187. | [(4-{2-[3-(4-tert.-butylphenyl)-[1,2,4]oxadiazol-5-yl]-vinyl}-cyclohexyl)-(4-chlorophenyl)-methyl]-dimethylamine (more highly polar diastereomer) | 478.2 [M$^+$ + 1]; 480.0 |
| 188. | [(4-{2-[3-(4-tert.-butylphenyl)-[1,2,4]oxadiazol-5-yl]-vinyl}-cyclohexyl)-(4-chlorophenyl)-methyl]-dimethylamine (more highly nonpolar diastereomer) | 478.2 [M$^+$ + 1]; 480.0 |
| 189. | ((4-chlorophenyl)-{4-[2-(3-m-tolyl-[1,2,4]oxadiazol-5-yl)-vinyl]-cyclohexyl}-methyl)-dimethylamine (more highly polar diastereomer) | 436.0 [M$^+$ + 1]; 438.0 |
| 190. | ((4-chlorophenyl)-{4-[2-(3-m-tolyl-[1,2,4]oxadiazol-5-yl)-vinyl]-cyclohexyl}-methyl)-dimethylamine (more highly nonpolar diastereomer) | 436.0 [M$^+$ + 1]; 438.0 |
| 191. | [(4-chlorophenyl)-(4-{2-[3-(4-chlorophenyl)-[1,2,4]oxadiazol-5-yl]-vinyl}-cyclohexyl)-methyl]-dimethylamine | 456.0 [M$^+$ + 1]; 458.0 |
| 192. | (4-{2-[3-(3-chlorophenyl)-[1,2,4]oxadiazol-5-yl]-vinyl}-cyclohexyl)-thiophen-2-yl-methyl]-dimethylamine | 428.0 [M$^+$ + 1]; 430.0 |
| 193. | [(4-{2-[3-(4-tert.-butylphenyl)-[1,2,4]oxadiazol-5-yl]-vinyl}-cyclohexyl)-thiophen-2-yl-methyl]-dimethylamine (more highly polar diastereomer) | 450.3 [M$^+$ + 1] |
| 194. | [(4-{2-[3-(4-tert.-butylphenyl)-[1,2,4]oxadiazol-5-yl]-vinyl}-cyclohexyl)-thiophen-2-yl-methyl]-dimethylamine (more highly nonpolar diastereomer) | 450.3 [M$^+$ + 1] |
| 195. | dimethyl-(thiophen-2-yl-{4-[2-(3-m-tolyl-[1,2,4]oxadiazol-5-yl)-vinyl]-cyclohexyl}-methyl)-amine | 408.2 [M$^+$ + 1] |
| 196. | [(4-{2-[3-(4-chlorophenyl)-[1,2,4]oxadiazol-5-yl]-vinyl}-cyclohexyl)-thiophen-2-yl-methyl]-dimethylamine | 428.0 [M$^+$ + 1]; 430.0 |
| 197. | [(4-{2-[3-(3-chlorophenyl)-[1,2,4]oxadiazol-5-yl]-vinyl}-cyclohexyl)-(3-fluorophenyl)-methyl]-dimethylamine | 440.0 [M$^+$ + 1]; 442.0 |
| 198. | [(4-{2-[3-(4-tert.-butylphenyl)-[1,2,4]oxadiazol-5-yl]-vinyl}-cyclohexyl)-(3-fluorophenyl)-methyl]-dimethylamine (more highly polar diastereomer) | 462.3 [M$^+$ + 1] |
| 199. | [(4-{2-[3-(4-tert.-butylphenyl)-[1,2,4]oxadiazol-5-yl]-vinyl}-cyclohexyl)-(3-fluorophenyl)-methyl]-dimethylamine (more highly nonpolar diastereomer) | 462.3 [M$^+$ + 1] |
| 201. | ((3-fluorophenyl)-{4-[2-(3-m-tolyl-[1,2,4]oxadiazol-5-yl)-vinyl]-cyclohexyl}-methyl)-dimethylamine | 420.2 [M$^+$ + 1] |
| 202. | [(4-{2-[3-(4-chlorophenyl)-[1,2,4]oxadiazol-5-yl]-vinyl}-cyclohexyl)-(3-fluorophenyl)-methyl]-dimethylamine | 440.0; 442.0 [M$^+$ + 1] |
| 203. | [(4-{2-[3-(2,3-dichlorophenyl)-[1,2,4]oxadiazol-5-yl]-vinyl}-cyclohexyl)-(4-fluorophenyl)-methyl]-dimethylamine | 474.1; 476.1 [M$^+$ + 1] |
| 204. | [(4-fluorophenyl)-(4-{2-[3-(4-trifluoromethoxyphenyl)-[1,2,4]oxadiazol-5-yl]-vinyl}-cyclohexyl)-methyl]-dimethylamine | 490.2 [M$^+$ + 1] |
| 205. | [(4-{2-[3-(3,4-dimethoxybenzyl)-[1,2,4]oxadiazol-5-yl]-vinyl}-cyclohexyl)-(4-fluorophenyl)-methyl]-dimethylamine | 480.3 [M$^+$ + 1] |
| 206. | [(4-{2-[3-(1,5-dimethyl-1H-pyrrol-2-yl)-[1,2,4]oxadiazol-5-yl]-vinyl}-cyclohexyl)-(4-fluorophenyl)-methyl]-dimethylamine | 423.2 [M$^+$ + 1] |
| 207. | [1-(4-{2-[3-(2,3-dichlorophenyl)-[1,2,4]oxadiazol-5-yl]-vinyl}-cyclohexyl)-3-phenylpropyl]-dimethylamine | 484.1 [M$^+$ + 1]; 486.0 |

| No. | Name | Actual mass (ESI) |
|---|---|---|
| 208. | dimethyl-[3-phenyl-1-(4-{2-[3-(4-trifluoromethoxyphenyl)-[1,2,4]oxadiazol-5-yl]-vinyl}-cyclohexyl)-propyl]-amine (more highly polar diastereomer) | 500.2 [M$^+$ + 1] |
| 209. | dimethyl-[3-phenyl-1-(4-{2-[3-(4-trifluoromethoxyphenyl)-[1,2,4]oxadiazol-5-yl]-vinyl}-cyclohexyl)-propyl]-amine (more highly nonpolar diastereomer) | 500.2 [M$^+$ + 1] |
| 210. | [1-(4-{2-[3-(3,4-dimethoxybenzyl)-[1,2,4]oxadiazol-5-yl]-vinyl}-cyclohexyl)-3-phenylpropyl]-dimethylamine (more highly polar diastereomer) | 490.3 [M$^+$ + 1] |
| 211. | [1-(4-{2-[3-(3,4-dimethoxybenzyl)-[1,2,4]oxadiazol-5-yl]-vinyl}-cyclohexyl)-3-phenylpropyl]-dimethylamine (more highly nonpolar diastereomer) | 490.3 [M$^+$ + 1] |
| 212. | [1-(4-{2-[3-(1,5-dimethyl-1H-pyrrol-2-yl)-[1,2,4]oxadiazol-5-yl]-vinyl}-cyclohexyl)-3-phenylpropyl]-dimethylamine | 433.3 [M$^+$ + 1] |
| 213. | [(4-{2-[3-(2,3-dichlorophenyl)-[1,2,4]oxadiazol-5-yl]-vinyl}-cyclohexyl)-phenylmethyl]-dimethylamine | 456.0 [M$^+$ + 1]; 458.0 |
| 214. | [(4-{2-[3-(3,4-dimethoxybenzyl)-[1,2,4]oxadiazol-5-yl]-vinyl}-cyclohexyl)-phenylmethyl]-dimethylamine (more highly polar diastereomer) | 462.3 [M$^+$ + 1] |
| 215. | [(4-{2-[3-(3,4-dimethoxybenzyl)-[1,2,4]oxadiazol-5-yl]-vinyl}-cyclohexyl)-phenylmethyl]-dimethylamine (more highly nonpolar diastereomer) | 462.3 [M$^+$ + 1] |
| 217. | [(4-{2-[3-(1,5-dimethyl-1H-pyrrol-2-yl)-[1,2,4]oxadiazol-5-yl]-vinyl}-cyclohexyl)-phenylmethyl]-dimethylamine | 405.3 [M$^+$ + 1] |
| 218. | [(4-chlorophenyl)-(4-{2-[3-(2,3-dichlorophenyl)-[1,2,4]oxadiazol-5-yl]-vinyl}-cyclohexyl)-methyl]-dimethylamine | 490.1 [M$^+$ + 1]; 492.0; 494.0 |
| 219. | [(4-chlorophenyl)-(4-{2-[3-(4-trifluoromethoxyphenyl)-[1,2,4]oxadiazol-5-yl]-vinyl}-cyclohexyl)-methyl]-dimethylamine | 506.0 [M$^+$ + 1]; 508.0 |
| 220. | [(4-chlorophenyl)-(4-{2-[3-(3,4-dimethoxybenzyl)-[1,2,4]oxadiazol-5-yl]-vinyl}-cyclohexyl)-methyl]-dimethylamine | 496.1 [M$^+$ + 1]; 498.0 |
| 221. | [(4-chlorophenyl)-(4-{2-[3-(1,5-dimethyl-1H-pyrrol-2-yl)-[1,2,4]oxadiazol-5-yl]-vinyl}-cyclohexyl)-methyl]-dimethylamine | 439.1 [M$^+$ + 1]; 441.0 |
| 222. | (4-{2-[3-(2,3-dichlorophenyl)-[1,2,4]oxadiazol-5-yl]-vinyl}-cyclohexyl)-thiophen-2-yl-methyl]-dimethylamine | 462.0 [M$^+$ + 1]; 464.0; 466.0 |
| 223. | dimethyl-[thiophen-2-yl-(4-{2-[3-(4-trifluoromethoxyphenyl)-[1,2,4]oxadiazol-5-yl]-vinyl}-cyclohexyl)-methyl]-amine | 478.2 [M$^+$ + 1] |
| 224. | (4-{2-[3-(1,5-dimethyl-1H-pyrrol-2-yl)-[1,2,4]oxadiazol-5-yl]-vinyl}-cyclohexyl)-thiophen-2-yl-methyl]-dimethylamine | 411.2 [M$^+$ + 1] |
| 225. | [(4-{2-[3-(2,3-dichlorophenyl)-[1,2,4]oxadiazol-5-yl]-vinyl}-cyclohexyl)-(3-fluorophenyl)-methyl]-dimethylamine | 474.1 [M$^+$ + 1]; 476.0; 478.0 |
| 226. | [(3-fluorophenyl)-(4-{2-[3-(4-trifluoromethoxyphenyl)-[1,2,4]oxadiazol-5-yl]-vinyl}-cyclohexyl)-methyl]-dimethylamine (more highly polar diastereomer) | 490.2 [M$^+$ + 1] |
| 227. | [(3-fluorophenyl)-(4-{2-[3-(4-trifluoromethoxyphenyl)-[1,2,4]oxadiazol-5-yl]-vinyl}-cyclohexyl)-methyl]-dimethylamine (more highly nonpolar diastereomer) | 490.2 [M$^+$ + 1] |
| 228. | [(4-{2-[3-(3,4-dimethoxybenzyl)-[1,2,4]oxadiazol-5-yl]-vinyl}-cyclohexyl)-(3-fluorophenyl)-methyl]-dimethylamine (more highly polar diastereomer) | 480.3 [M$^+$ + 1] |
| 229. | [(4-{2-[3-(3,4-dimethoxybenzyl)-[1,2,4]oxadiazol-5-yl]-vinyl}-cyclohexyl)-(3-fluorophenyl)-methyl]-dimethylamine (more highly nonpolar diastereomer) | 480.3 [M$^+$ + 1] |
| 231. | [(4-{2-[3-(1,5-dimethyl-1H-pyrrol-2-yl)-[1,2,4]oxadiazol-5-yl]-vinyl}-cyclohexyl)-(3-fluorophenyl)-methyl]-dimethylamine | 423.2 [M$^+$ + 1] |
| 232. | {(3-fluorophenyl)-[4-(3-phenyl-[1,2,4]oxadiazol-5-ylmethyl)-cyclohexyl]-methyl}-dimethylamine | 394.2 [M$^+$ + 1] |
| 233. | {(4-fluorophenyl)-[4-(3-phenyl-[1,2,4]oxadiazol-5-ylmethyl)-cyclohexyl]-methyl}-dimethylamine | 394.2 [M$^+$ + 1] |
| 234. | dimethyl-{phenyl-[4-(3-phenyl-[1,2,4]oxadiazol-5-ylmethyl)-cyclohexyl]-methyl}-amine | 376.2 [M$^+$ + 1] |
| 235. | [{4-[3-(2,4-difluorophenyl)-[1,2,4]oxadiazol-5-ylmethyl]-cyclohexyl}-(3-fluorophenyl)-methyl]-dimethylamine | 430.2 [M$^+$ + 1] |
| 236. | [{4-[3-(2,4-difluorophenyl)-[1,2,4]oxadiazol-5-ylmethyl]-cyclohexyl}-(4-fluorophenyl)-methyl]-dimethylamine | 430.2 [M$^+$ + 1] |
| 237. | ((3-fluorophenyl)-{4-[3-(4-methoxybenzyl)-[1,2,4]oxadiazol-5-ylmethyl]-cyclohexyl}-methyl)-dimethylamine | 438.2 [M$^+$ + 1] |
| 238. | ((4-fluorophenyl)-{4-[3-(4-methoxybenzyl)-[1,2,4]oxadiazol-5-ylmethyl]-cyclohexyl}-methyl)-dimethylamine | 438.2 [M$^+$ + 1] |
| 239. | ({4-[3-(4-methoxybenzyl)-[1,2,4]oxadiazol-5-ylmethyl]-cyclohexyl}-phenylmethyl)-dimethylamine | 420.3 [M$^+$ + 1] |
| 240. | [{4-[3-(4-chlorobenzyl)-[1,2,4]oxadiazol-5-ylmethyl]-cyclohexyl}-(3-fluorophenyl)-methyl]-dimethylamine | 442.1 [M$^+$ + 1]; 444.0 |
| 241. | [{4-[3-(4-chlorobenzyl)-[1,2,4]oxadiazol-5-ylmethyl]-cyclohexyl}-(4-fluorophenyl)-methyl]-dimethylamine | 442.1 [M$^+$ + 1]; 444.0 |
| 242. | [{4-[3-(3-chlorophenyl)-[1,2,4]oxadiazol-5-ylmethyl]-cyclohexyl}-(4-fluorophenyl)-methyl]-dimethylamine | 428.0 [M$^+$ + 1]; 430.0 |

| No. | Name | Actual mass (ESI) |
|---|---|---|
| 243. | ({4-[3-(3-chlorophenyl)-[1,2,4]oxadiazol-5-ylmethyl]-cyclohexyl}-phenylmethyl)-dimethylamine | 410.1 [M⁺ + 1]; 412.0 |
| 244. | [{4-[3-(2,3-dichlorophenyl)-[1,2,4]oxadiazol-5-ylmethyl]-cyclohexyl}-(3-fluorophenyl)-methyl]-dimethylamine | 462.1 [M⁺ + 1]; 464.0 |
| 245. | [{4-[3-(2,3-dichlorophenyl)-[1,2,4]oxadiazol-5-ylmethyl]-cyclohexyl}-(4-fluorophenyl)-methyl]-dimethylamine | 462.1 [M⁺ + 1]; 464.0; 466.0 |
| 246. | ({4-[3-(2,3-dichlorophenyl)-[1,2,4]oxadiazol-5-ylmethyl]-cyclohexyl}-phenylmethyl)-dimethylamine | 444.0 [M⁺ + 1]; 446.0; 448.0 |
| 247. | {(3-fluorophenyl)-[4-(3-p-tolyl-[1,2,4]oxadiazol-5-ylmethyl)-cyclohexyl]-methyl}-dimethylamine | 408.2 [M⁺ + 1] |
| 248. | {(4-fluorophenyl)-[4-(3-p-tolyl-[1,2,4]oxadiazol-5-ylmethyl)-cyclohexyl]-methyl}-dimethylamine | 408.2 [M⁺ + 1] |
| 249. | dimethyl-{phenyl-[4-(3-p-tolyl-[1,2,4]oxadiazol-5-ylmethyl)-cyclohexyl]-methyl}-amine | 390.2 [M⁺ + 1] |
| 250. | [{4-[3-(3,4-dimethoxyphenyl)-[1,2,4]oxadiazol-5-ylmethyl]-cyclohexyl}-(3-fluorophenyl)-methyl]-dimethylamine | 454.2 [M⁺ + 1] |
| 251. | [{4-[3-(3,4-dimethoxyphenyl)-[1,2,4]oxadiazol-5-ylmethyl]-cyclohexyl}-(4-fluorophenyl)-methyl]-dimethylamine | 454.2 [M⁺ + 1] |
| 252. | ({4-[3-(3,4-dimethoxyphenyl)-[1,2,4]oxadiazol-5-ylmethyl]-cyclohexyl}-phenylmethyl)-dimethylamine | 436.3 [M⁺ + 1] |
| 253. | [{4-[3-(4-tert.-butylphenyl)-[1,2,4]oxadiazol-5-ylmethyl]-cyclohexyl}-(3-fluorophenyl)-methyl]-dimethylamine | 450.3 [M⁺ + 1] |
| 254. | [{4-[3-(4-tert.-butylphenyl)-[1,2,4]oxadiazol-5-ylmethyl]-cyclohexyl}-(4-fluorophenyl)-methyl]-dimethylamine | 450.3 [M⁺ + 1] |
| 255. | ({4-[3-(4-tert.-butylphenyl)-[1,2,4]oxadiazol-5-ylmethyl]-cyclohexyl}-phenylmethyl)-dimethylamine | 432.3 [M⁺ + 1] |
| 256. | {(3-fluorophenyl)-[4-(3-m-tolyl-[1,2,4]oxadiazol-5-ylmethyl)-cyclohexyl]-methyl}-dimethylamine | 408.2 [M⁺ + 1] |
| 257. | {(4-fluorophenyl)-[4-(3-m-tolyl-[1,2,4]oxadiazol-5-ylmethyl)-cyclohexyl]-methyl}-dimethylamine | 408.2 [M⁺ + 1] |
| 258. | dimethyl-{phenyl-[4-(3-m-tolyl-[1,2,4]oxadiazol-5-ylmethyl)-cyclohexyl]-methyl}-amine | 390.2 [M⁺ + 1] |
| 259. | [{4-[3-(4-chlorophenyl)-[1,2,4]oxadiazol-5-ylmethyl]-cyclohexyl}-(3-fluorophenyl)-methyl]-dimethylamine | 428.1 [M⁺ + 1]; 430.0 |
| 260. | ({4-[3-(4-chlorophenyl)-[1,2,4]oxadiazol-5-ylmethyl]-cyclohexyl}-phenylmethyl)-dimethylamine | 410.1 [M⁺ + 1]; 412.0 |
| 261. | ((3-fluorophenyl)-{4-[3-(4-trifluoromethoxyphenyl)-[1,2,4]oxadiazol-5-ylmethyl]-cyclohexyl}-methyl)-dimethylamine | 478.2 [M⁺ + 1] |
| 262. | ((4-fluorophenyl)-{4-[3-(4-trifluoromethoxyphenyl)-[1,2,4]oxadiazol-5-ylmethyl]-cyclohexyl}-methyl)-dimethylamine | 478.2 [M⁺ + 1] |
| 263. | dimethyl-(phenyl-{4-[3-(4-trifluoromethoxyphenyl)-[1,2,4]oxadiazol-5-ylmethyl]-cyclohexyl}-methyl)-amine | 460.2 [M⁺ + 1] |
| 264. | ((4-fluorophenyl)-{4-[2-(3-phenyl-[1,2,4]oxadiazol-5-yl)-ethyl]-cyclohexyl}-methyl)-dimethylamine | 408.2 [M⁺ + 1] |
| 265. | dimethyl-(phenyl-{4-[2-(3-phenyl-[1,2,4]oxadiazol-5-yl)-ethyl]-cyclohexyl}-methyl)-amine | 390.2 [M⁺ + 1] |
| 266. | dimethyl-(3-phenyl-1-{4-[2-(3-phenyl-[1,2,4]oxadiazol-5-yl)-ethyl]-cyclohexyl}-propyl)-amine | 418.3 [M⁺ + 1] |
| 267. | ((3-fluorophenyl)-{4-[2-(3-phenyl-[1,2,4]oxadiazol-5-yl)-ethyl]-cyclohexyl}-methyl)-dimethylamine | 408.2 [M⁺ + 1] |
| 268. | [(4-fluorophenyl)-(4-{2-[3-(4-methoxybenzyl)-[1,2,4]oxadiazol-5-yl]-ethyl}-cyclohexyl)-methyl]-dimethylamine | 452.3 [M⁺ + 1] |
| 269. | [(4-{2-[3-(4-methoxybenzyl)-[1,2,4]oxadiazol-5-yl]-ethyl}-cyclohexyl)-phenylmethyl]-dimethylamine | 434.3 [M⁺ + 1] |
| 270. | [1-(4-{2-[3-(4-methoxybenzyl)-[1,2,4]oxadiazol-5-yl]-ethyl}-cyclohexyl)-3-phenylpropyl]-dimethylamine | 462.3 [M⁺ + 1] |
| 271. | [(3-fluorophenyl)-(4-{2-[3-(4-methoxybenzyl)-[1,2,4]oxadiazol-5-yl]-ethyl}-cyclohexyl)-methyl]-dimethylamine | 452.3 [M⁺ + 1] |
| 272. | [(4-{2-[3-(4-chlorobenzyl)-[1,2,4]oxadiazol-5-yl]-ethyl}-cyclohexyl)-(4-fluorophenyl)-methyl]-dimethylamine | 456.1 [M⁺ + 1]; 458.0 |
| 273. | [(4-{2-[3-(4-chlorobenzyl)-[1,2,4]oxadiazol-5-yl]-ethyl}-cyclohexyl)-phenylmethyl]-dimethylamine | 438.1 [M⁺ + 1]; 440.1 |
| 274. | [1-(4-{2-[3-(4-chlorobenzyl)-[1,2,4]oxadiazol-5-yl]-ethyl}-cyclohexyl)-3-phenylpropyl]-dimethylamine | 466.1 [M⁺ + 1]; 468.1 |
| 275. | [(4-{2-[3-(4-chlorobenzyl)-[1,2,4]oxadiazol-5-yl]-ethyl}-cyclohexyl)-(3-fluoropheny)-methyl]-dimethylamine | 456.1 [M⁺ + 1]; 458.1 |
| 276. | [(4-{2-[3-(3-chlorophenyl)-[1,2,4]oxadiazol-5-yl]-ethyl}-cyclohexyl)-(4-fluorophenyl)-methyl]-dimethylamine | 442.1 [M⁺ + 1]; 444.1 |
| 277. | [(4-{2-[3-(3-chlorophenyl)-[1,2,4]oxadiazol-5-yl]-ethyl}-cyclohexyl)-phenylmethyl]-dimethylamine | 424.1 [M⁺ + 1]; 426.1 |
| 278. | [1-(4-{2-[3-(3-chlorophenyl)-[1,2,4]oxadiazol-5-yl]-ethyl}-cyclohexyl)-3-phenylpropyl]-dimethylamine | 452.1 [M⁺ + 1]; 454.1 |
| 279. | [(4-{2-[3-(3-chlorophenyl)-[1,2,4]oxadiazol-5-yl]-ethyl}-cyclohexyl)-(3-fluorophenyl)-methyl]-dimethylamine | 442.1 [M⁺ + 1]; 444.0 |
| 280. | [(4-{2-[3-(2,4-difluorophenyl)-[1,2,4]oxadiazol-5-yl]-ethyl}-cyclohexyl)-(4-fluorophenyl)-methyl]-dimethylamine | 444.2 [M⁺ + 1] |

| No. | Name | Actual mass (ESI) |
|---|---|---|
| 281. | [(4-{2-[3-(2,4-difluorophenyl)-[1,2,4]oxadiazol-5-yl]-ethyl}-cyclohexyl)-phenylmethyl]-dimethylamine | 426.2 [M$^+$ + 1] |
| 282. | [(4-{2-[3-(2,4-difluorophenyl)-[1,2,4]oxadiazol-5-yl]-ethyl}-cyclohexyl)-(3-fluorophenyl)-methyl]-dimethylamine | 444.2 [M$^+$ + 1] |
| 283. | [(4-{2-[3-(3,4-dimethoxyphenyl)-[1,2,4]oxadiazol-5-yl]-ethyl}-cyclohexyl)-(4-fluorophenyl)-methyl]-dimethylamine | 468.3 [M$^+$ + 1] |
| 284. | [(4-{2-[3-(3,4-dimethoxyphenyl)-[1,2,4]oxadiazol-5-yl]-ethyl}-cyclohexyl)-phenylmethyl]-dimethylamine | 450.3 [M$^+$ + 1] |
| 285. | [1-(4-{2-[3-(3,4-dimethoxyphenyl)-[1,2,4]oxadiazol-5-yl]-ethyl}-cyclohexyl)-3-phenylpropyl]-dimethylamine | 478.3 [M$^+$ + 1] |
| 286. | [(4-{2-[3-(3,4-dimethoxyphenyl)-[1,2,4]oxadiazol-5-yl]-ethyl}-cyclohexyl)-(3-fluorophenyl)-methyl]-dimethylamine | 468.3 [M$^+$ + 1] |
| 287. | ((4-fluorophenyl)-{4-[2-(3-p-tolyl-[1,2,4]oxadiazol-5-yl)-ethyl]-cyclohexyl}-methyl)-dimethylamine | 422.3 [M$^+$ + 1] |
| 288. | dimethyl-(phenyl-{4-[2-(3-p-tolyl-[1,2,4]oxadiazol-5-yl)-ethyl]-cyclohexyl}-methyl)-amine | 404.3 [M$^+$ + 1] |
| 289. | dimethyl-(3-phenyl-1-{4-[2-(3-p-tolyl-[1,2,4]oxadiazol-5-yl)-ethyl]-cyclohexyl}-propyl)-amine | 432.3 [M$^+$ + 1] |
| 290. | ((3-fluorophenyl)-{4-[2-(3-p-tolyl-[1,2,4]oxadiazol-5-yl)-ethyl]-cyclohexyl}-methyl)-dimethylamine | 422.3 [M$^+$ + 1] |
| 291. | [(4-{2-[3-(4-tert.-butylphenyl)-[1,2,4]oxadiazol-5-yl]-ethyl}-cyclohexyl)-(4-fluorophenyl)-methyl]-dimethylamine | 464.3 [M$^+$ + 1] |
| 292. | [(4-{2-[3-(4-tert.-butylphenyl)-[1,2,4]oxadiazol-5-yl]-ethyl}-cyclohexyl)-phenylmethyl]-dimethylamine | 446.3 [M$^+$ + 1] |
| 293. | [1-(4-{2-[3-(4-tert.-butylphenyl)-[1,2,4]oxadiazol-5-yl]-ethyl}-cyclohexyl)-3-phenylpropyl]-dimethylamine | 474.3 [M$^+$ + 1] |
| 294. | [(4-{2-[3-(4-tert.-butylphenyl)-[1,2,4]oxadiazol-5-yl]-ethyl}-cyclohexyl)-(3-fluorophenyl)-methyl]-dimethylamine | 464.3 [M$^+$ + 1] |
| 295. | ((4-fluorophenyl)-{4-[2-(3-m-tolyl-[1,2,4]oxadiazol-5-yl)-ethyl]-cyclohexyl}-methyl)-dimethylamine | 422.3 [M$^+$ + 1] |
| 296. | dimethyl-(phenyl-{4-[2-(3-m-tolyl-[1,2,4]oxadiazol-5-yl)-ethyl]-cyclohexyl}-methyl)-amine | 404.3 [M$^+$ + 1] |
| 297. | dimethyl-(3-phenyl-1-{4-[2-(3-m-tolyl-[1,2,4]oxadiazol-5-yl)-ethyl]-cyclohexyl}-propyl)-amine | 432.3 [M$^+$ + 1] |
| 298. | ((3-fluorophenyl)-{4-[2-(3-m-tolyl-[1,2,4]oxadiazol-5-yl)-ethyl]-cyclohexyl}-methyl)-dimethylamine | 422.3 [M$^+$ + 1] |
| 299. | [(4-{2-[3-(4-chlorophenyl)-[1,2,4]oxadiazol-5-yl]-ethyl}-cyclohexyl)-(4-fluorophenyl)-methyl]-dimethylamine | 442.1 [M$^+$ + 1]; 444.0 |
| 300. | [(4-{2-[3-(4-chlorophenyl)-[1,2,4]oxadiazol-5-yl]-ethyl}-cyclohexyl)-phenylmethyl]-dimethylamine | 424.1 [M$^+$ + 1]; 426.0 |
| 301. | [1-(4-{2-[3-(4-chlorophenyl)-[1,2,4]oxadiazol-5-yl]-ethyl}-cyclohexyl)-3-phenylpropyl]-dimethylamine | 452.1 [M$^+$ + 1]; 454.1 |
| 302. | [(4-{2-[3-(4-chlorophenyl)-[1,2,4]oxadiazol-5-yl]-ethyl}-cyclohexyl)-(3-fluorophenyl)-methyl]-dimethylamine | 442.0 [M$^+$ + 1]; 444.0 |
| 303. | [(4-{2-[3-(2,3-dichlorophenyl)-[1,2,4]oxadiazol-5-yl]-ethyl}-cyclohexyl)-(4-fluorophenyl)-methyl]-dimethylamine | 476.0 [M$^+$ + 1]; 478.0; 480.0 |
| 304. | [(4-{2-[3-(2,3-dichlorophenyl)-[1,2,4]oxadiazol-5-yl]-ethyl}-cyclohexyl)-phenylmethyl]-dimethylamine | 458.0 [M$^+$ + 1]; 460.0; 462.0 |
| 305. | [1-(4-{2-[3-(2,3-dichlorophenyl)-[1,2,4]oxadiazol-5-yl]-ethyl}-cyclohexyl)-3-phenylpropyl]-dimethylamine | 486.0 [M$^+$ + 1]; 488.0 |
| 306. | [(4-{2-[3-(2,3-dichlorophenyl)-[1,2,4]oxadiazol-5-yl]-ethyl}-cyclohexyl)-(3-fluorophenyl)-methyl]-dimethylamine | 476.0 [M$^+$ + 1]; 478.0 |
| 307. | [(4-fluorophenyl)-(4-{2-[3-(4-trifluoromethoxyphenyl)-[1,2,4]oxadiazol-5-yl]-ethyl}-cyclohexyl)-methyl]-dimethylamine | 492.2 [M$^+$ + 1] |
| 308. | dimethyl-[phenyl-(4-{2-[3-(4-trifluoromethoxyphenyl)-[1,2,4]oxadiazol-5-yl]-ethyl}-cyclohexyl)-methyl]-amine | 474.2 [M$^+$ + 1] |
| 309. | dimethyl-3-phenyl-1-(4-{2-[3-(4-trifluoromethoxyphenyl)-[1,2,4]oxadiazol-5-yl]-ethyl}-cyclohexyl-propyl]-amine | 502.3 [M$^+$ + 1] |
| 310. | [(3-fluorophenyl)-(4-{2-[3-(4-trifluoromethoxyphenyl)-[1,2,4]oxadiazol-5-yl]-ethyl}-cyclohexyl)-methyl]-dimethylamine | 492.2 [M$^+$ + 1] |
| 311. | (4-((3-(4-fluorobenzyl)-1,2,4-oxadiazol-5-yl)methyl)cyclohexyl)(4-fluorophenyl)-N,N-dimethylmethanamine | 426.2 [M$^+$ + 1] |
| 312. | (4-((3-(4-fluorobenzyl)-1,2,4-oxadiazol-5-yl)methyl)cyclohexyl)-N,N-dimethyl(phenyl)methanamine | 408.2 [M$^+$ + 1] |
| 313. | (4-((3-(3-chlorobenzyl)-1,2,4-oxadiazol-5-yl)methyl)cyclohexyl)(3-fluorophenyl)-N,N-dimethylmethanamine | 442.1 [M$^+$ + 1]; 444.2 |
| 314. | (4-((3-(3-chlorobenzyl)-1,2,4-oxadiazol-5-yl)methyl)cyclohexyl)(4-fluorophenyl)-N,N-dimethylmethanamine | 442.1 [M$^+$ + 1]; 444.2 |
| 315. | (4-((3-(3-chlorobenzyl)-1,2,4-oxadiazol-5-yl)methyl)cyclohexyl)-N,N-dimethyl(phenyl)methanamine | 424.1 [M$^+$ + 1]; 426.2 |
| 316. | (4-((3-(3-bromophenyl)-1,2,4-oxadiazol-5-yl)methyl)cyclohexyl)(3-fluorophenyl)-N,N-dimethylmethanamine | 472.1 [M$^+$ + 1]; 474.1 |
| 317. | (4-((3-(3-bromophenyl)-1,2,4-oxadiazol-5-yl)methyl)cyclohexyl)(4-fluorophenyl)-N,N-dimethylmethanamine | 472.1 [M$^+$ + 1]; 474.1 |
| 318. | (4-((3-(3-bromophenyl)-1,2,4-oxadiazol-5-yl)methyl)cyclohexyl)-N,N-dimethyl(phenyl)methanamine | 454.1 [M$^+$ + 1]; 456.1 |

| No. | Name | Actual mass (ESI) |
| --- | --- | --- |
| 319. | (4-((3-(4-bromobenzyl)-1,2,4-oxadiazol-5-yl)methyl)cyclohexyl)(3-fluorophenyl)-N,N-dimethylmethanamine | 486.1 [M⁺ + 1]; 488.1 |
| 320. | (4-((3-(4-bromobenzyl)-1,2,4-oxadiazol-5-yl)methyl)cyclohexyl)(4-fluorophenyl)-N,N-dimethylmethanamine | 486.1 [M⁺ + 1]; 488.1 |
| 321. | (4-((3-(4-bromobenzyl)-1,2,4-oxadiazol-5-yl)methyl)cyclohexyl)-N,N-dimethyl(phenyl)methanamine | 468.1 [M⁺ + 1]; 470.1 |
| 322. | (3-fluorophenyl)-N,N-dimethyl(4-((3-(thiophen-2-ylmethyl)-1,2,4-oxadiazol-5-yl)methyl)cyclohexyl)methanamine | 414.2 [M⁺ + 1] |
| 323. | (4-fluorophenyl)-N,N-dimethyl(4-((3-(thiophen-2-ylmethyl)-1,2,4-oxadiazol-5-yl)methyl)cyclohexyl)methanamine | 414.2 [M⁺ + 1] |
| 324. | N,N-dimethyl(phenyl)(4-((3-(thiophen-2-ylmethyl)-1,2,4-oxadiazol-5-yl)methyl)cyclohexyl)methanamine | 396.2 [M⁺ + 1] |
| 325. | (4-((3-benzyl-1,2,4-oxadiazol-5-yl)methyl)cyclohexyl)(3-fluorophenyl)-N,N-dimethylmethanamine | 408.2 [M⁺ + 1] |
| 326. | (4-((3-benzyl-1,2,4-oxadiazol-5-yl)methyl)cyclohexyl)(4-fluorophenyl)-N,N-dimethylmethanamine | 408.2 [M⁺ + 1] |
| 327. | (4-((3-benzyl-1,2,4-oxadiazol-5-yl)methyl)cyclohexyl)-N,N-dimethyl(phenyl)methanamine | 390.2 [M⁺ + 1] |
| 328. | (3-fluorophenyl)-N,N-dimethyl(4-((3-phenethyl-1,2,4-oxadiazol-5-yl)methyl)cyclohexyl)methanamine | 422.3 [M⁺ + 1] |
| 329. | (4-fluorophenyl)-N,N-dimethyl(4-((3-phenethyl-1,2,4-oxadiazol-5-yl)methyl)cyclohexyl)methanamine | 422.3 [M⁺ + 1] |
| 330. | N,N-dimethyl(4-((3-phenethyl-1,2,4-oxadiazol-5-yl)methyl)cyclohexyl)(phenyl)methanamine | 404.3 [M⁺ + 1] |
| 331. | (4-((3-((1H-indol-3-yl)methyl)-1,2,4-oxadiazol-5-yl)methyl)cyclohexyl)(3-fluorophenyl)-N,N-dimethylmethanamine | 447.2 [M⁺ + 1] |

Separation of the Diastereomers

Diastereomers were obtained from the syntheses, these in particular comprising E/Z isomers. In those cases in which diastereomers were separated, separation was performed by the following method:

The crude product was introduced into a VP 100/21 Nucleodur C18 (5 μm), 100 mm, 21 mm internal diameter HPLC column from Macherey-Nagel with the assistance of a Waters 600 HPLC pump, mobile phase water/methanol, using an initial eluent of 20-50% water at 25° C. and a flow rate of 20 ml/min. Within 8-12 min, the methanol content of the eluent was continuously raised to 100%. Detection was performed with a Waters 2487 UV detector at 220 and 254 nm and ES-MS. The separated fractions were collected, evaporated and analysed by ES mass spectroscopy. In the present invention, the example compounds which were eluted in the first fraction are described as the "more highly polar diastereomer" and those in the second fraction as the "more highly nonpolar diastereomer.

The Example Compounds have the following substitution pattern ($R^3$, $R^4$=CH$_3$):

| No. | X | $R^2$ | $R^1$ |
| --- | --- | --- | --- |
| 45 | CH | 4-Cl-phenyl | 4-Cl-phenyl |
| 46 | CH | 4-F-phenyl | 4-Cl-phenyl |
| 47 | CH | 4-F-phenyl | 4-Cl-phenyl |
| 48 | CH | phenyl | 2,3-dichlorophenyl |

-continued

| No. | X | R² | R¹ |
|---|---|---|---|
| 49 | CH | phenyl | 2,3-dichlorophenyl |
| 50 | CH | 3-fluorophenyl | 2,3-dichlorophenyl |
| 51 | CH | 3-fluorophenyl | 2,3-dichlorophenyl |
| 52 | CH | 4-chlorophenyl | 2,3-dichlorophenyl |
| 53 | CH | 4-chlorophenyl | 2,3-dichlorophenyl |
| 54 | CH | 2-phenylethyl | 2,3-dichlorophenyl |
| 55 | CH | 4-fluorophenyl | 2,3-dichlorophenyl |
| 56 | CH | 4-fluorophenyl | 2,3-dichlorophenyl |
| 57 | CH | phenyl | 4-(trifluoromethoxy)phenyl |
| 58 | CH | phenyl | 4-(trifluoromethoxy)phenyl |

-continued
| No. | X | R² | R¹ |
|---|---|---|---|
| 59 | CH | 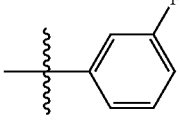 | 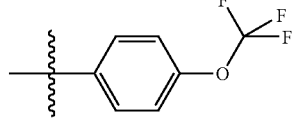 |
| 60 | CH | 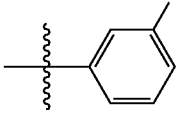 | 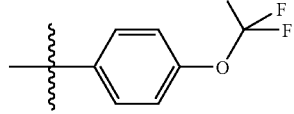 |
| 61 | CH | 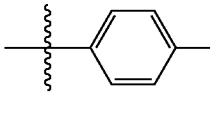 | 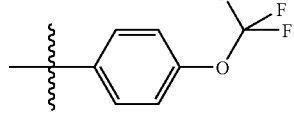 |
| 62 | CH | 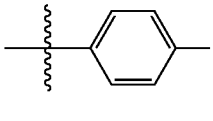 | 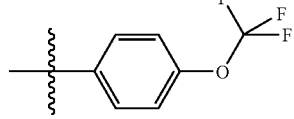 |
| 63 | CH | 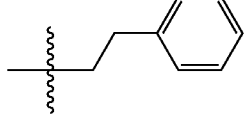 | 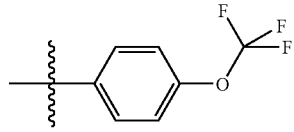 |
| 64 | CH | 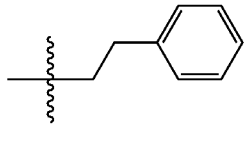 | 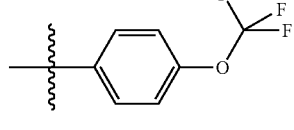 |
| 65 | CH | 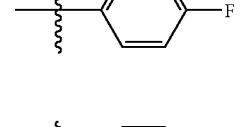 | 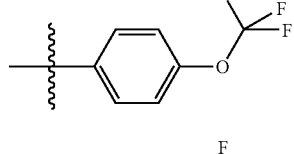 |
| 66 | CH | 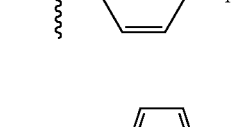 | 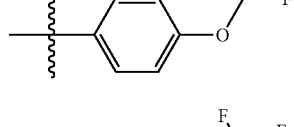 |
| 67 | CH | 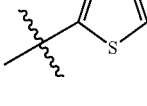 | 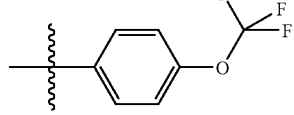 |
| 68 | CH | 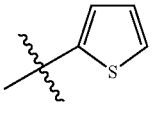 | 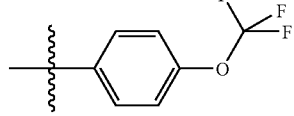 |
| 69 | CH | 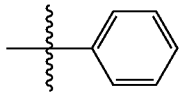 | 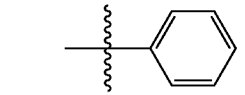 |

-continued
| No. | X | R² | R¹ |
|---|---|---|---|
| 70 | CH | 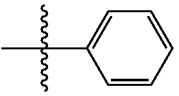 | 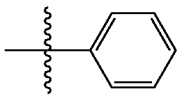 |
| 71 | CH | 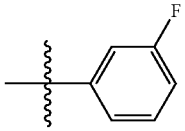 | 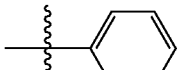 |
| 72 | CH | 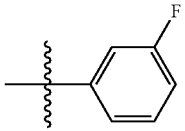 | 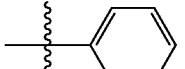 |
| 73 | CH | 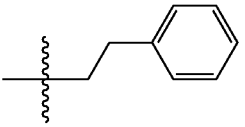 | 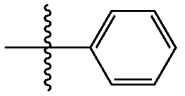 |
| 74 | CH | 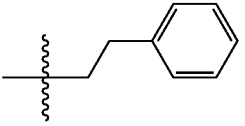 | 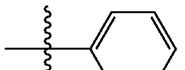 |
| 75 | CH | 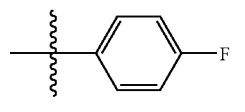 | 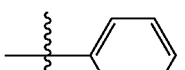 |
| 76 | CH | 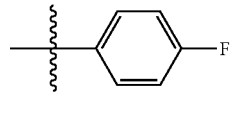 | 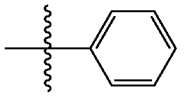 |
| 77 | CH | 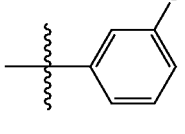 | 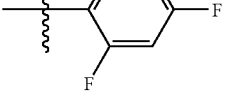 |
| 78 | CH | 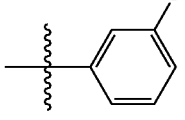 | 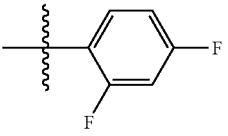 |
| 79 | CH | 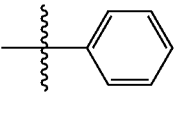 | 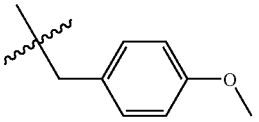 |
| 80 | CH | 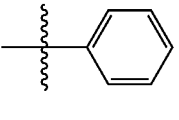 | 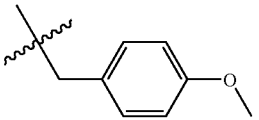 |

-continued
| No. | X | R² | R¹ |
|---|---|---|---|
| 81 | CH | 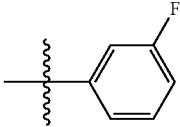 3-F-phenyl | 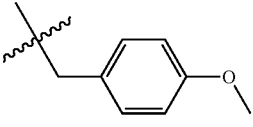 4-methoxybenzyl |
| 82 | CH | 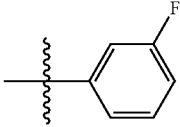 3-F-phenyl | 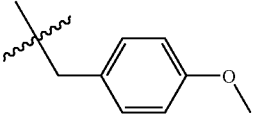 4-methoxybenzyl |
| 83 | CH | 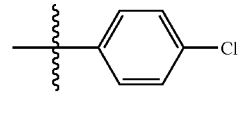 4-Cl-phenyl | 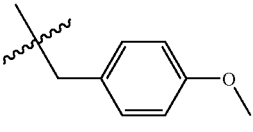 4-methoxybenzyl |
| 84 | CH | 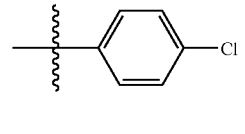 4-Cl-phenyl | 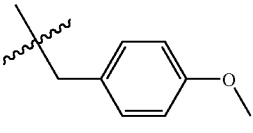 4-methoxybenzyl |
| 85 | CH | 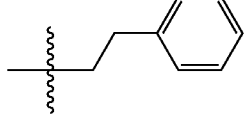 phenethyl | 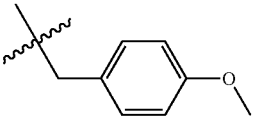 4-methoxybenzyl |
| 86 | CH | 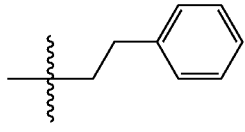 phenethyl | 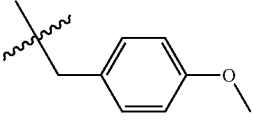 4-methoxybenzyl |
| 87 | CH | 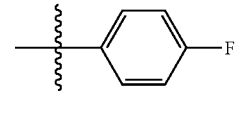 4-F-phenyl | 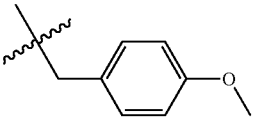 4-methoxybenzyl |
| 88 | CH | 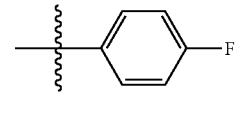 4-F-phenyl | 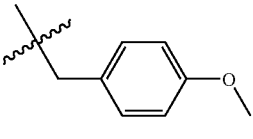 4-methoxybenzyl |
| 89 | CH | 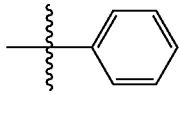 phenyl | 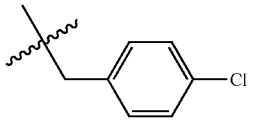 4-chlorobenzyl |
| 90 | CH | 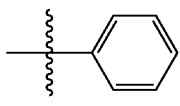 phenyl | 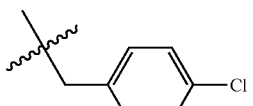 4-chlorobenzyl |
| 91 | CH | 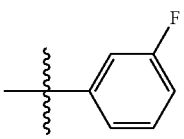 3-F-phenyl | 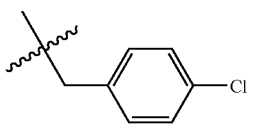 4-chlorobenzyl |

-continued
| No. | X | R² | R¹ |
|---|---|---|---|
| 92 | CH | 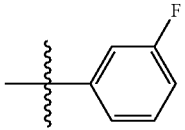 | 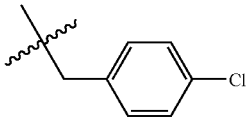 |
| 93 | CH | 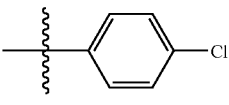 | 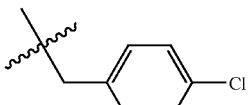 |
| 94 | CH | 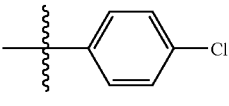 | 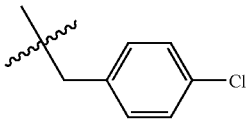 |
| 95 | CH | 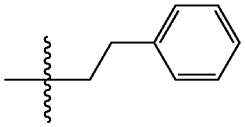 | 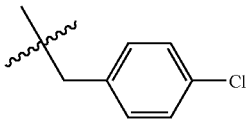 |
| 96 | CH | 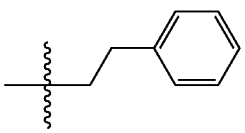 | 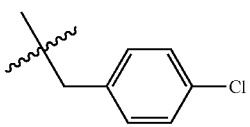 |
| 97 | CH | 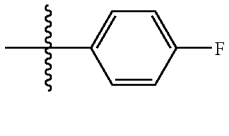 | 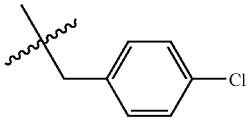 |
| 98 | CH | 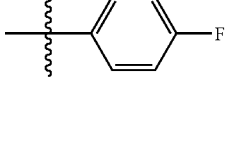 | 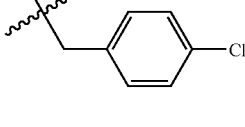 |
| 99 | CH | 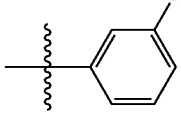 | 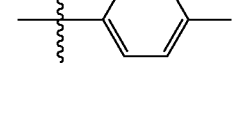 |
| 100 | CH | 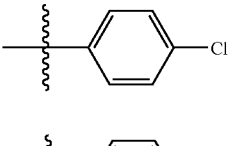 | 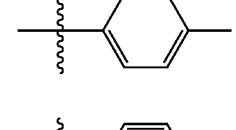 |
| 101 | CH | 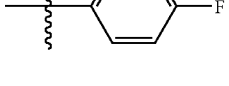 | 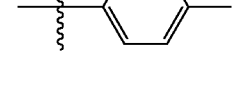 |
| 102 | CH | 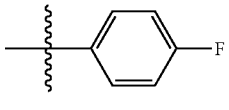 | 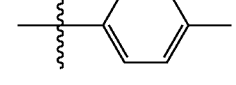 |

-continued

| No. | X | R² | R¹ |
|---|---|---|---|
| 103 | CH | phenyl | 3,4-dimethoxyphenyl |
| 104 | CH | phenyl | 3,4-dimethoxyphenyl |
| 105 | CH | 3-fluorophenyl | 3,4-dimethoxyphenyl |
| 106 | CH | 3-fluorophenyl | 3,4-dimethoxyphenyl |
| 107 | CH | 4-chlorophenyl | 3,4-dimethoxyphenyl |
| 108 | CH | 4-chlorophenyl | 3,4-dimethoxyphenyl |
| 109 | CH | 2-phenylethyl | 3,4-dimethoxyphenyl |
| 110 | CH | 2-phenylethyl | 3,4-dimethoxyphenyl |
| 111 | CH | 4-fluorophenyl | 3,4-dimethoxyphenyl |
| 112 | CH | 4-fluorophenyl | 3,4-dimethoxyphenyl |

-continued
| No. | X | R² | R¹ |
|---|---|---|---|
| 113 | CH | 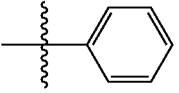 | 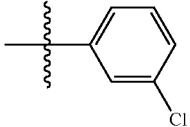 |
| 114 | CH | 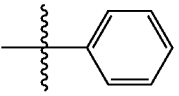 | 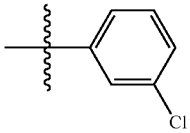 |
| 115 | CH | 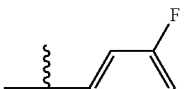 | 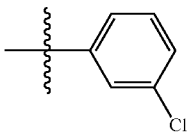 |
| 116 | CH | 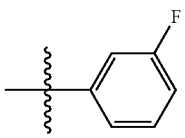 | 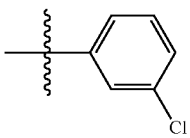 |
| 117 | CH | 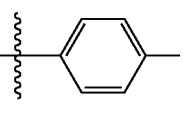 | 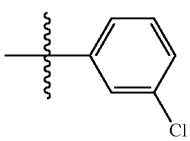 |
| 118 | CH | 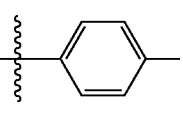 | 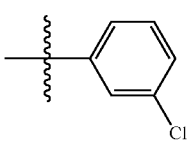 |
| 119 | CH | 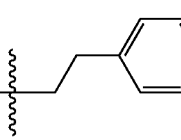 | 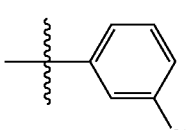 |
| 120 | CH | 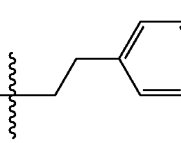 | 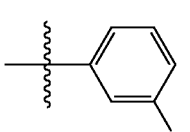 |
| 121 | CH | 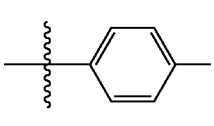 | 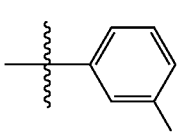 |
| 122 | CH | 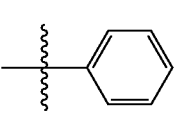 | 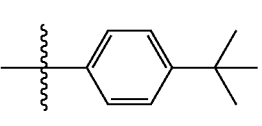 |
| 123 | CH | 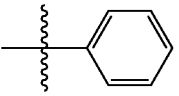 | 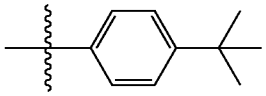 |

-continued

| No. | X | R² | R¹ |
|---|---|---|---|
| 124 | CH | 3-F-phenyl | 4-tert-butylphenyl |
| 125 | CH | 3-F-phenyl | 4-tert-butylphenyl |
| 126 | CH | 4-Cl-phenyl | 4-tert-butylphenyl |
| 127 | CH | 4-Cl-phenyl | 4-tert-butylphenyl |
| 128 | CH | 2-phenylethyl | 4-tert-butylphenyl |
| 129 | CH | 2-phenylethyl | 4-tert-butylphenyl |
| 130 | CH | 4-F-phenyl | 4-tert-butylphenyl |
| 131 | CH | 4-F-phenyl | 4-tert-butylphenyl |
| 132 | CH | 5-methylthiophen-2-yl | 4-tert-butylphenyl |
| 133 | CH | 5-methylthiophen-2-yl | 4-tert-butylphenyl |
| 134 | CH | phenyl | 3-methylphenyl |
| 135 | CH | phenyl | 3-methylphenyl |

| No. | X | R² | R¹ |
|---|---|---|---|
| 136 | CH | 3-F-phenyl | 3-methylphenyl |
| 137 | CH | 3-F-phenyl | 3-methylphenyl |
| 138 | CH | 4-Cl-phenyl | 3-methylphenyl |
| 139 | CH | 4-Cl-phenyl | 3-methylphenyl |
| 140 | CH=CH | 4-F-phenyl | phenyl |
| 141 | CH=CH | 4-F-phenyl | 2,4-diF-phenyl |
| 142 | CH=CH | 4-F-phenyl | 4-methoxybenzyl |
| 143 | CH=CH | 4-F-phenyl | 4-Cl-benzyl |
| 144 | CH=CH | 2-phenylethyl | phenyl |
| 145 | CH=CH | 2-phenylethyl | 2,4-diF-phenyl |
| 146 | CH=CH | 2-phenylethyl | 4-methoxybenzyl |

-continued
| No. | X | R² | R¹ |
|---|---|---|---|
| 147 | CH=CH | 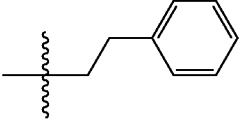 | 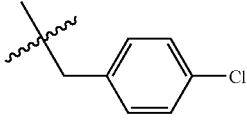 |
| 148 | CH=CH | 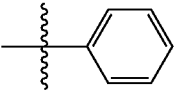 | 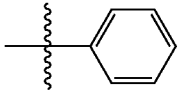 |
| 149 | CH=CH | 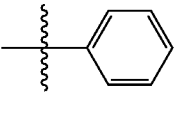 | 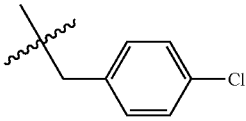 |
| 150 | CH=CH | 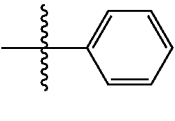 | 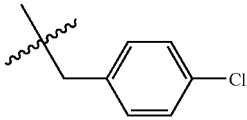 |
| 151 | CH=CH | 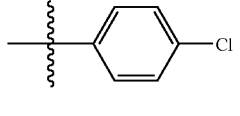 | 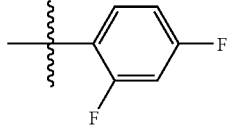 |
| 152 | CH=CH | 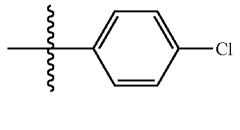 | 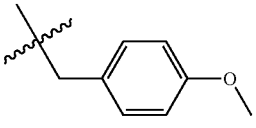 |
| 153 | CH=CH | 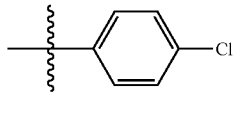 | 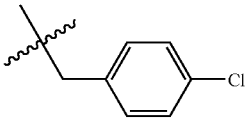 |
| 154 | CH=CH | 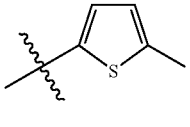 | 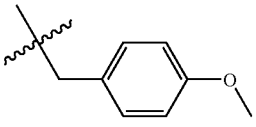 |
| 155 | CH=CH | 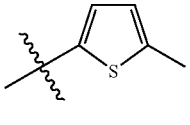 | 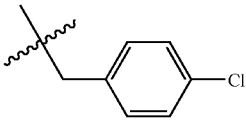 |
| 156 | CH=CH | 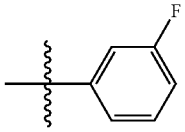 | 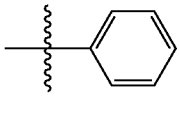 |
| 157 | CH=CH | 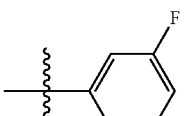 | 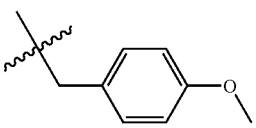 |

-continued
| No. | X | R² | R¹ |
|---|---|---|---|
| 158 | CH=CH | 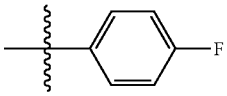 4-F-phenyl | 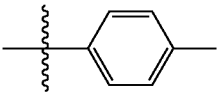 4-methylphenyl |
| 159 | CH=CH | 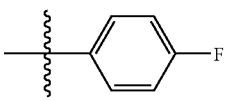 4-F-phenyl | 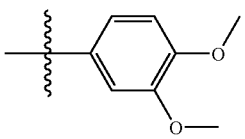 3,4-dimethoxyphenyl |
| 160 | CH=CH | 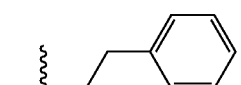 phenethyl | 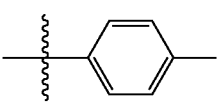 4-methylphenyl |
| 161 | CH=CH | 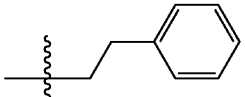 phenethyl | 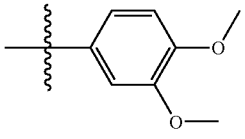 3,4-dimethoxyphenyl |
| 162 | CH=CH | 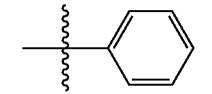 phenyl | 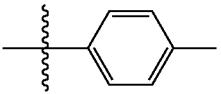 4-methylphenyl |
| 163 | CH=CH | 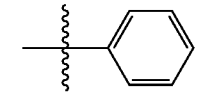 phenyl | 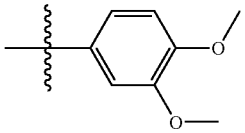 3,4-dimethoxyphenyl |
| 164 | CH=CH | 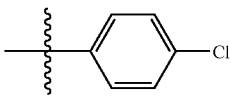 4-Cl-phenyl | 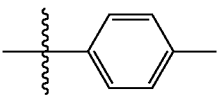 4-methylphenyl |
| 165 | CH=CH | 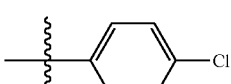 4-Cl-phenyl | 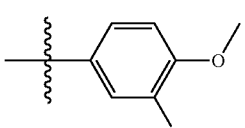 3,4-dimethoxyphenyl |
| 166 | CH=CH | 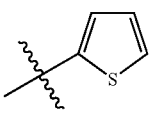 2-thienyl | 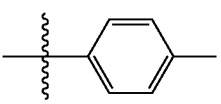 4-methylphenyl |
| 167 | CH=CH | 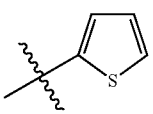 2-thienyl | 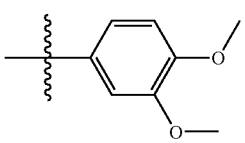 3,4-dimethoxyphenyl |
| 168 | CH=CH | 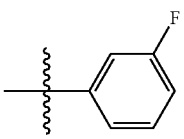 3-F-phenyl | 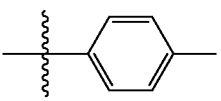 4-methylphenyl |

-continued

| No. | X | R² | R¹ |
|---|---|---|---|
| 169 | CH=CH | 3-F-phenyl | 3,4-dimethoxyphenyl |
| 170 | CH=CH | 4-F-phenyl | 3-Cl-phenyl |
| 171 | CH=CH | 4-F-phenyl | 4-tert-butyl-phenyl |
| 172 | CH=CH | 4-F-phenyl | 4-tert-butyl-phenyl |
| 173 | CH=CH | 4-F-phenyl | 3-methyl-phenyl |
| 174 | CH=CH | -CH₂-phenyl | 3-Cl-phenyl |
| 175 | CH=CH | -CH₂-phenyl | 4-tert-butyl-phenyl |
| 176 | CH=CH | -CH₂-phenyl | 4-tert-butyl-phenyl |
| 177 | CH=CH | -CH₂-phenyl | 3-methyl-phenyl |
| 178 | CH=CH | -CH₂-phenyl | 3-methyl-phenyl |
| 179 | CH=CH | phenyl | 3-Cl-phenyl |

-continued
| No. | X | R² | R¹ |
|---|---|---|---|
| 180 | CH=CH | 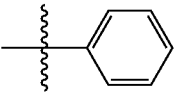 | 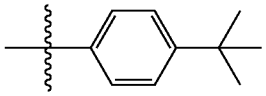 |
| 181 | CH=CH | 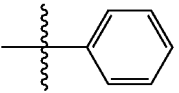 |  |
| 182 | CH=CH | 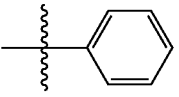 | 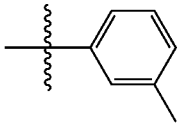 |
| 183 | CH=CH | 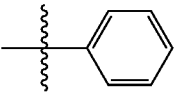 | 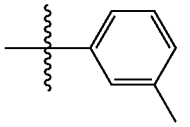 |
| 184 | CH=CH | 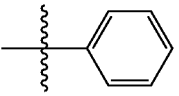 | 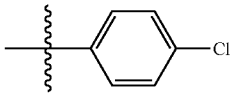 |
| 185 | CH=CH | 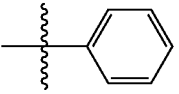 | 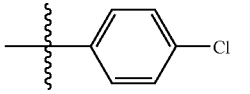 |
| 186 | CH=CH | 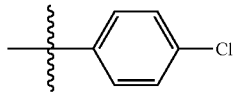 | 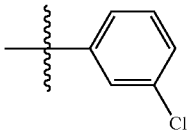 |
| 187 | CH=CH | 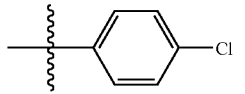 | 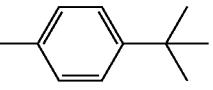 |
| 188 | CH=CH | 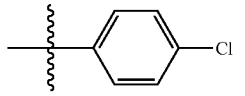 | 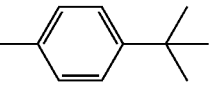 |
| 189 | CH=CH | 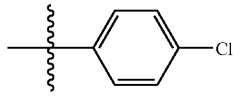 | 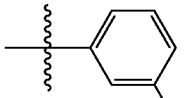 |
| 190 | CH=CH | 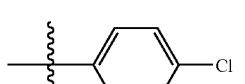 | 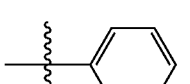 |
| 191 | CH=CH | 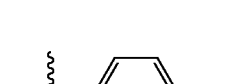 | 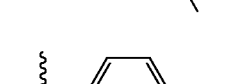 |

-continued
| No. | X | R² | R¹ |
|---|---|---|---|
| 192 | CH=CH | 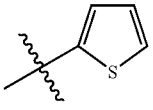 | 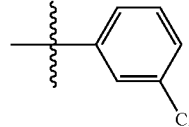 |
| 193 | CH=CH | 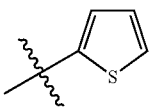 | 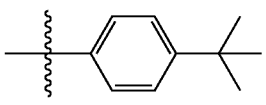 |
| 194 | CH=CH | 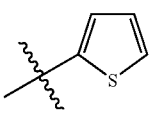 | 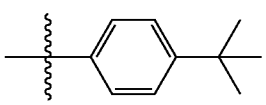 |
| 195 | CH=CH | 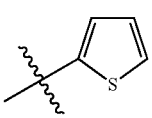 | 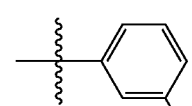 |
| 196 | CH=CH | 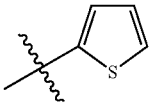 | 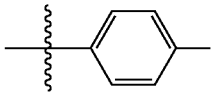 |
| 197 | CH=CH | 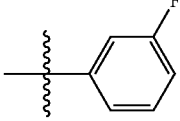 | 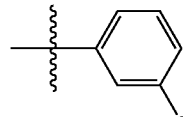 |
| 198 | CH=CH | 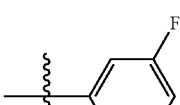 | 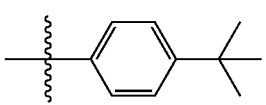 |
| 199 | CH=CH | 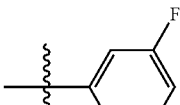 | 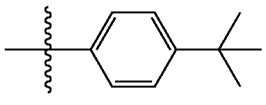 |
| 201 | CH=CH | 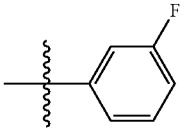 | 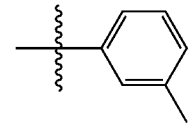 |
| 202 | CH=CH | 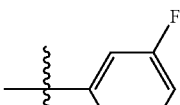 | 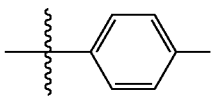 |
| 203 | CH=CH | 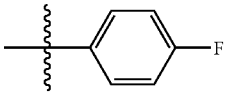 | 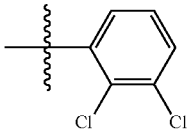 |

-continued
| No. | X | R² | R¹ |
|---|---|---|---|
| 204 | CH=CH | 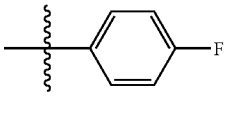 | 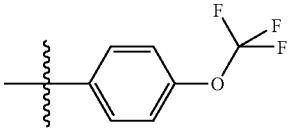 |
| 205 | CH=CH | 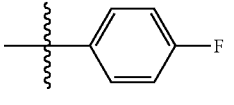 | 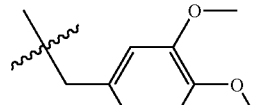 |
| 206 | CH=CH | 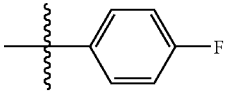 | 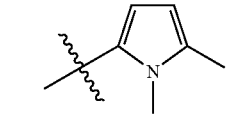 |
| 207 | CH=CH | 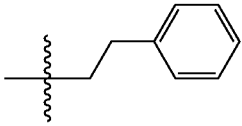 | 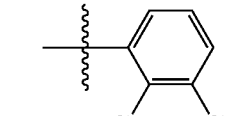 |
| 208 | CH=CH | 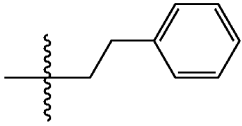 | 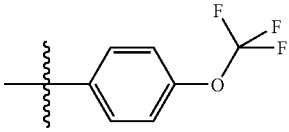 |
| 209 | CH=CH | 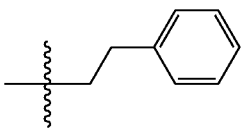 | 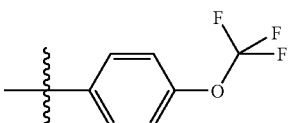 |
| 210 | CH=CH | 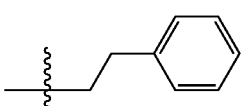 | 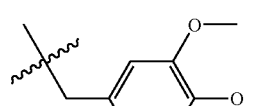 |
| 211 | CH=CH | 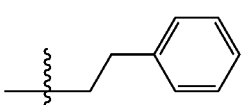 | 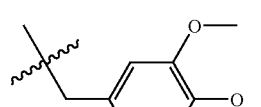 |
| 212 | CH=CH | 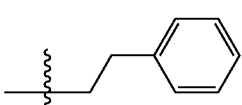 | 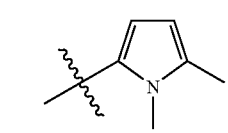 |
| 213 | CH=CH | 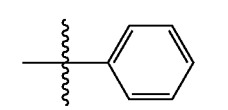 | 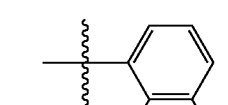 |
| 214 | CH=CH | 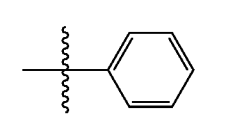 | 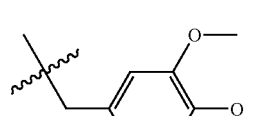 |

-continued
| No. | X | R² | R¹ |
|---|---|---|---|
| 215 | CH=CH | 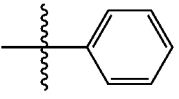 | 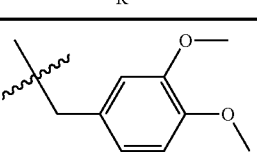 |
| 217 | CH=CH | 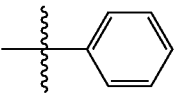 | 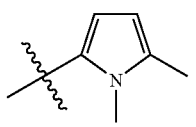 |
| 218 | CH=CH | 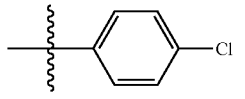 | 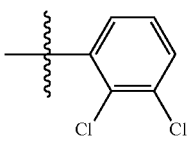 |
| 219 | CH=CH | 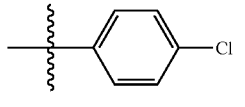 | 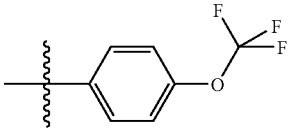 |
| 220 | CH=CH | 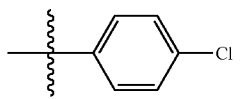 | 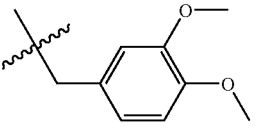 |
| 221 | CH=CH | 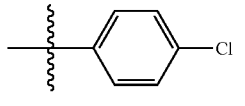 | 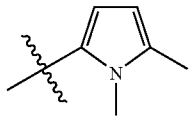 |
| 222 | CH=CH | 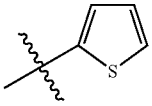 | 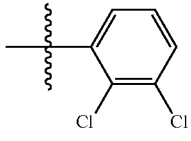 |
| 223 | CH=CH | 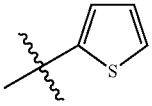 | 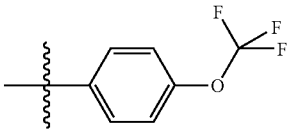 |
| 224 | CH=CH | 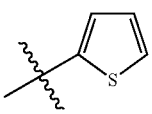 | 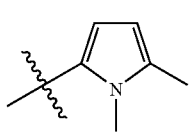 |
| 225 | CH=CH | 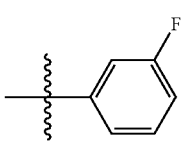 | 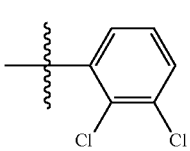 |
| 226 | CH=CH | 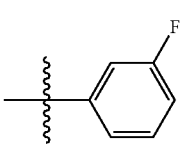 | 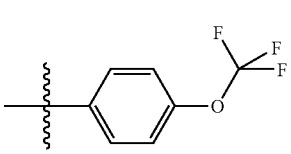 |

-continued

| No. | X | R² | R¹ |
|---|---|---|---|
| 227 | CH=CH | 3-F-phenyl | 4-(OCF₃)-phenyl |
| 228 | CH=CH | 3-F-phenyl | 3,4-dimethoxybenzyl |
| 229 | CH=CH | 3-F-phenyl | 3,4-dimethoxybenzyl |
| 231 | CH=CH | 3-F-phenyl | 1,5-dimethyl-1H-pyrrol-2-yl |
| 232 | CH₂ | 3-F-phenyl | phenyl |
| 233 | CH₂ | 4-F-phenyl | phenyl |
| 234 | CH₂ | phenyl | phenyl |
| 235 | CH₂ | 3-F-phenyl | 2,4-difluorophenyl |
| 236 | CH₂ | 4-F-phenyl | 2,4-difluorophenyl |
| 237 | CH₂ | 3-F-phenyl | 4-methoxybenzyl |
| 238 | CH₂ | 4-F-phenyl | 4-methoxybenzyl |

| No. | X | R² | R¹ |
|---|---|---|---|
| 239 | CH₂ | 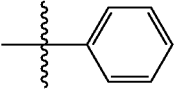 | 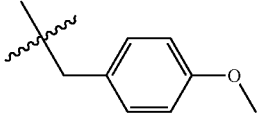 |
| 240 | CH₂ | 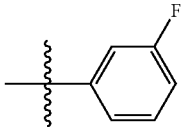 | 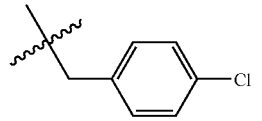 |
| 241 | CH₂ | 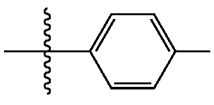 | 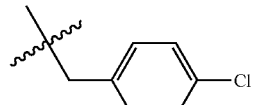 |
| 242 | CH₂ | 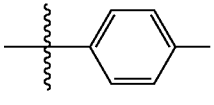 | 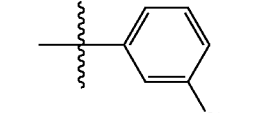 |
| 243 | CH₂ | 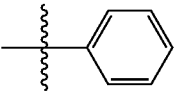 | 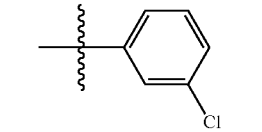 |
| 244 | CH₂ | 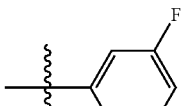 | 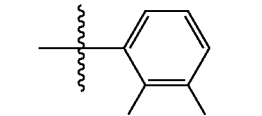 |
| 245 | CH₂ | 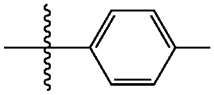 | 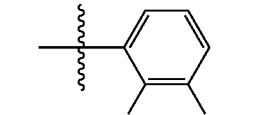 |
| 246 | CH₂ | 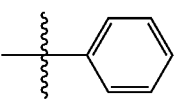 | 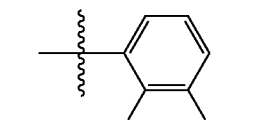 |
| 247 | CH₂ | 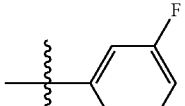 | 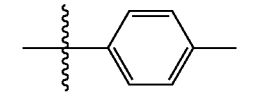 |
| 248 | CH₂ | 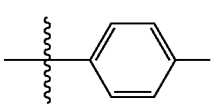 | 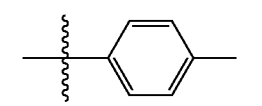 |
| 249 | CH₂ | 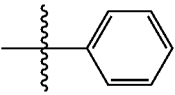 | 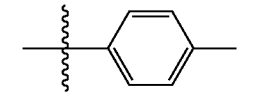 |

-continued

| No. | X | R² | R¹ |
|---|---|---|---|
| 250 | CH₂ | 3-F-phenyl | 3,4-dimethoxyphenyl |
| 251 | CH₂ | 4-F-phenyl | 3,4-dimethoxyphenyl |
| 252 | CH₂ | phenyl | 3,4-dimethoxyphenyl |
| 253 | CH₂ | 3-F-phenyl | 4-tert-butylphenyl |
| 254 | CH₂ | 4-F-phenyl | 4-tert-butylphenyl |
| 255 | CH₂ | phenyl | 4-tert-butylphenyl |
| 256 | CH₂ | 3-F-phenyl | 3-methylphenyl |
| 257 | CH₂ | 4-F-phenyl | 3-methylphenyl |
| 258 | CH₂ | phenyl | 3-methylphenyl |
| 259 | CH₂ | 3-F-phenyl | 4-Cl-phenyl |
| 260 | CH₂ | phenyl | 4-Cl-phenyl |

-continued
| No. | X | R² | R¹ |
|---|---|---|---|
| 261 | CH₂ | 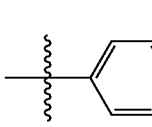 | 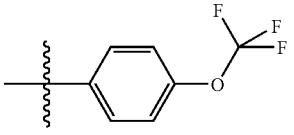 |
| 262 | CH₂ | 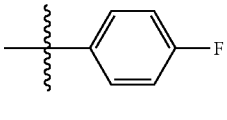 | 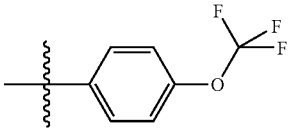 |
| 263 | CH₂ | 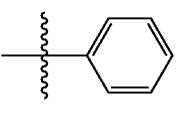 | 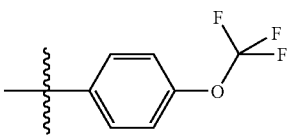 |
| 264 | CH₂CH₂ | 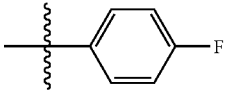 | 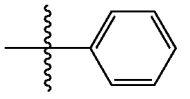 |
| 265 | CH₂CH₂ | 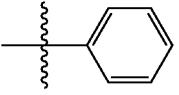 | 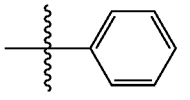 |
| 266 | CH₂CH₂ | 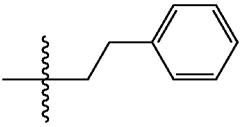 | 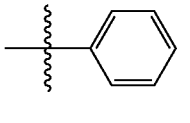 |
| 267 | CH₂CH₂ | 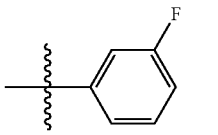 | 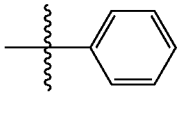 |
| 268 | CH₂CH₂ | 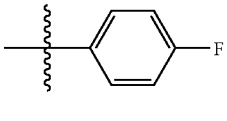 | 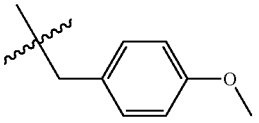 |
| 269 | CH₂CH₂ | 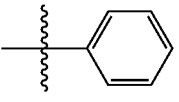 | 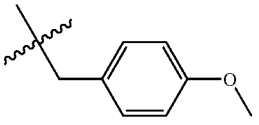 |
| 270 | CH₂CH₂ | 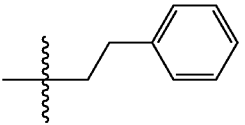 | 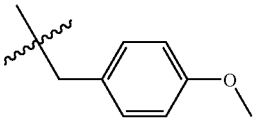 |
| 271 | CH₂CH₂ | 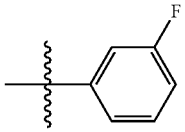 | 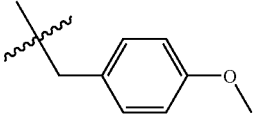 |

-continued

| No. | X | R² | R¹ |
|---|---|---|---|
| 272 | CH₂CH₂ | 4-F-phenyl | 4-Cl-benzyl |
| 273 | CH₂CH₂ | phenyl | 4-Cl-benzyl |
| 274 | CH₂CH₂ | 2-phenylethyl | 4-Cl-benzyl |
| 275 | CH₂CH₂ | 3-F-phenyl | 4-Cl-benzyl |
| 276 | CH₂CH₂ | 4-F-phenyl | 3-Cl-phenyl |
| 277 | CH₂CH₂ | phenyl | 3-Cl-phenyl |
| 278 | CH₂CH₂ | 2-phenylethyl | 3-Cl-phenyl |
| 279 | CH₂CH₂ | 3-F-phenyl | 3-Cl-phenyl |
| 280 | CH₂CH₂ | 4-F-phenyl | 2,4-di-F-phenyl |
| 281 | CH₂CH₂ | phenyl | 2,4-di-F-phenyl |
| 282 | CH₂CH₂ | 3-F-phenyl | 2,4-di-F-phenyl |

-continued

| No. | X | R² | R¹ |
|---|---|---|---|
| 283 | CH₂CH₂ | 4-F-phenyl | 3,4-dimethoxyphenyl |
| 284 | CH₂CH₂ | phenyl | 3,4-dimethoxyphenyl |
| 285 | CH₂CH₂ | 2-phenylethyl | 3,4-dimethoxyphenyl |
| 286 | CH₂CH₂ | 3-F-phenyl | 3,4-dimethoxyphenyl |
| 287 | CH₂CH₂ | 4-F-phenyl | 4-methylphenyl |
| 288 | CH₂CH₂ | phenyl | 4-methylphenyl |
| 289 | CH₂CH₂ | 2-phenylethyl | 4-methylphenyl |
| 290 | CH₂CH₂ | 3-F-phenyl | 4-methylphenyl |
| 291 | CH₂CH₂ | 4-F-phenyl | 4-tert-butylphenyl |
| 292 | CH₂CH₂ | phenyl | 4-tert-butylphenyl |
| 293 | CH₂CH₂ | 2-phenylethyl | 4-tert-butylphenyl |

-continued

| No. | X | R² | R¹ |
|---|---|---|---|
| 294 | CH₂CH₂ | 3-F-phenyl | 4-tert-butyl-phenyl |
| 295 | CH₂CH₂ | 4-F-phenyl | 3-methyl-phenyl |
| 296 | CH₂CH₂ | phenyl | 3-methyl-phenyl |
| 297 | CH₂CH₂ | 2-phenylethyl | 3-methyl-phenyl |
| 298 | CH₂CH₂ | 3-F-phenyl | 3-methyl-phenyl |
| 299 | CH₂CH₂ | 4-F-phenyl | 4-Cl-phenyl |
| 300 | CH₂CH₂ | phenyl | 4-Cl-phenyl |
| 301 | CH₂CH₂ | 2-phenylethyl | 4-Cl-phenyl |
| 302 | CH₂CH₂ | 3-F-phenyl | 4-Cl-phenyl |
| 303 | CH₂CH₂ | 4-F-phenyl | 2,3-diCl-phenyl |
| 304 | CH₂CH₂ | phenyl | 2,3-diCl-phenyl |

-continued

| No. | X | R² | R¹ |
|---|---|---|---|
| 305 | CH₂CH₂ | -CH₂CH₂-C₆H₅ | 2,3-dichlorophenyl |
| 306 | CH₂CH₂ | 3-fluorophenyl | 2,3-dichlorophenyl |
| 307 | CH₂CH₂ | 4-fluorophenyl | 4-(trifluoromethoxy)phenyl |
| 308 | CH₂CH₂ | phenyl | 4-(trifluoromethoxy)phenyl |
| 309 | CH₂CH₂ | -CH₂CH₂-C₆H₅ | 4-(trifluoromethoxy)phenyl |
| 310 | CH₂CH₂ | 3-fluorophenyl | 4-(trifluoromethoxy)phenyl |
| 311 | CH₂ | 4-fluorophenyl | -CH₂-(4-fluorophenyl) |
| 312 | CH₂ | phenyl | -CH₂-(4-fluorophenyl) |
| 313 | CH₂ | 3-fluorophenyl | -CH₂-(3-chlorophenyl) |
| 314 | CH₂ | 4-fluorophenyl | -CH₂-(3-chlorophenyl) |

-continued
| No. | X | R² | R¹ |
|---|---|---|---|
| 315 | CH₂ | 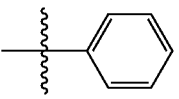 | 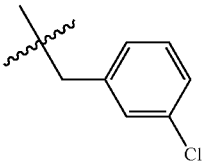 |
| 316 | CH₂ | 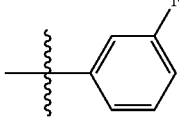 | 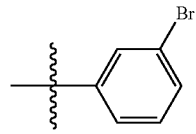 |
| 317 | CH₂ | 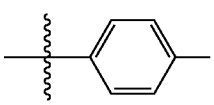 | 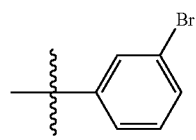 |
| 318 | CH₂ | 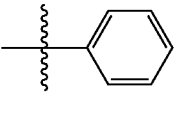 | 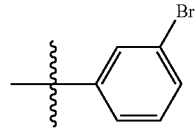 |
| 319 | CH₂ | 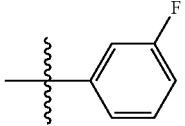 | 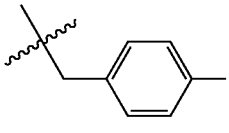 |
| 320 | CH₂ | 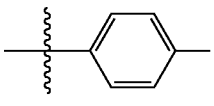 | 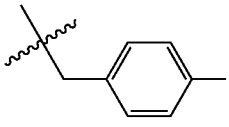 |
| 321 | CH₂ | 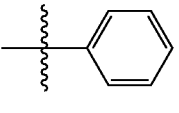 | 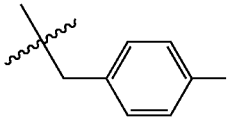 |
| 322 | CH₂ | 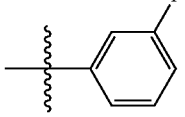 | 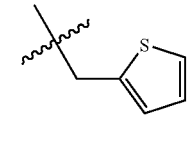 |
| 323 | CH₂ | 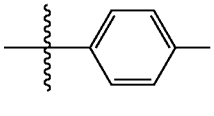 | 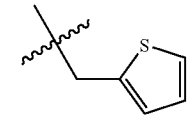 |
| 324 | CH₂ | 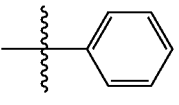 | 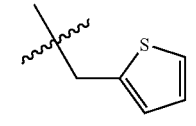 |
| 325 | CH₂ | 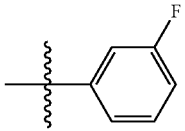 | 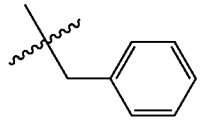 |

-continued

| No. | X | R² | R¹ |
|---|---|---|---|
| 326 | CH₂ | 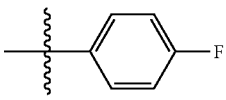 | 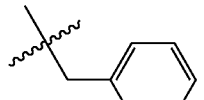 |
| 327 | CH₂ | 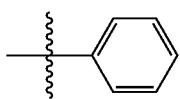 | 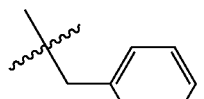 |
| 328 | CH₂ | 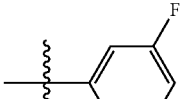 | 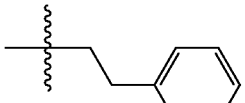 |
| 329 | CH₂ | 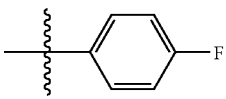 | 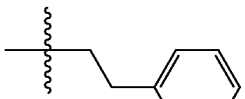 |
| 330 | CH₂ | 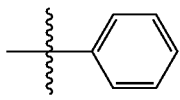 | 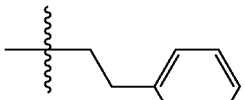 |
| 331 | CH₂ | 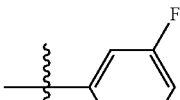 | 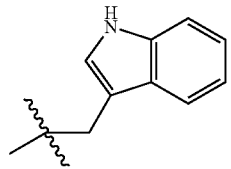 |

Investigations into the Efficacy of the Compounds According to the Invention

Method for Determining Affinity for Human μ Opiate Receptor

Receptor affinity for the human μ opiate receptor is determined in a homogeneous batch in microtitre plates. To this end, dilution series of the substances to be tested are incubated in a total volume of 250 μl for 90 minutes at room temperature with a receptor membrane preparation (15-40 μg protein/250 μl incubation batch) of CHO-K1 cells which express the human μ-opiate receptor (RB-HOM receptor membrane preparation from PerkinElmer Life Sciences, Zaventem, Belgium) in the presence of 1 nmol/l of the radioactive ligand [³H]-naloxone (NET719, from PerkinElmer Life Sciences, Zaventem, Belgium) and 1 mg of WGA-SPA beads (wheat germ agglutinin SPA beads from Amersham/Pharmacia, Freiburg, Germany). 50 mmol/l of tris HCl supplemented with 0.06% bovine serum albumin is used as the incubation buffer. Nonspecific binding is determined by additionally adding 100 μmol/l of naloxone. Once the ninety minute incubation time has elapsed, the microtitre plates are centrifuged off for 20 minutes at 1000 g and the radioactivity measured in a β counter (Microbeta-Trilux, from Perki-nElmer Wallac, Freiburg, Germany). The percentage displacement of the radioactive ligand from its binding to the human μ opiate receptor is determined at a concentration of the test substances of 1 μmol/l and stated as percentage inhibition of specific binding. On the basis of the percentage displacement brought about by different concentrations of the test substances, $IC_{50}$ inhibition concentrations which result in a 50% displacement of the radioactive ligand are calculated. $K_i$ values for the test substances are obtained by conversion using the Cheng-Prusoff equation.

Noradrenalin (NA) and Serotonin (5HT) Reuptake Inhibition

In order to be able to carry out these in vitro studies, synaptosomes are freshly isolated from rat brain regions. A "$P_2$" fraction is used, which is prepared according to the instructions given by Gray and Whittaker (E. G. Gray and V. P. Whittaker (1962) J. Anat. 76, 79-88). For NA uptake, these vesicular particles are isolated from the hypothalamus of male rat brains.

A detailed description of the method may be found in the literature (M. Ch. Frink, H.-H. Hennies, W. Engiberger, M. Haurand and B. Wilffert (1996) Arzneim.-Forsch./Drug Res. 46 (III), 11, 1029-1036).

TABLE 1

μ affinity of oxadiazoles

| No. | μ opioid receptor, % inhibition [1 μM] | μ opioid receptor, $K_i$ [μM] |
|---|---|---|
| 44 | 75 | 0.072 |
| 43 | 83 | 0.044 |
| 55 | 53 | |
| 69 | 40 | |
| 79 | 43 | |
| 135 | 44 | |
| 149 | 42 | |
| 150 | 56 | |
| 155 | 52 | |
| 183 | 40 | |
| 195 | 48 | |
| 224 | 54 | |
| 232 | 41 | |
| 234 | 64 | |
| 239 | 66 | |
| 243 | 55 | 0.32 |
| 246 | 56 | |
| 258 | 53 | |
| 269 | 43 | |
| 273 | 68 | |
| 281 | 69 | |
| 296 | 45 | |
| 304 | 51 | |

TABLE 2

Monoamine reuptake inhibition of selected oxadiazoles

| No. | Serotonin reuptake, % inhibition [10 μM] | Noradrenalin reuptake, % inhibition [10 μM] |
|---|---|---|
| 43 | 95 | 95 |
| 44 | 99 | 100 |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A substituted oxadiazole compound corresponding to formula I:

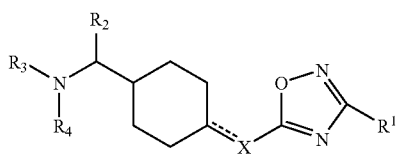

I wherein
X denotes CH, $CH_2$, CH=CH, $CH_2CH_2$, $CH_2$CH=CH or $CH_2CH_2CH_2$;
$R^1$ denotes unsubstituted or mono- or polysubstituted aryl or heteroaryl; or an unsubstituted or mono- or polysubstituted aryl or heteroaryl group linked via a $C_{1-3}$ alkylene group;
$R^2$ denotes unsubstituted or mono- or polysubstituted aryl or heteroaryl; or an unsubstituted or mono- or polysubstituted aryl group linked via a $C_{1-3}$ alkylene chain; and
$R^3$ and $R^4$ independently denote H; or saturated or unsaturated, branched or unbranched $C_{1-6}$ alkyl; with the proviso that $R^3$ and $R^4$ are not simultaneously H; or
$R^3$ and $R^4$ together denote —$CH_2CH_2OCH_2CH_2$— or —$(CH_2)_{3-6}$—,
or a salt thereof with a physiologically acceptable acid.

2. A compound as claimed in claim 1, wherein said compound is in the form of an isolated stereoisomer.

3. A compound as claimed in claim 1, wherein said compound is in the form of a mixture of stereoisomers.

4. A compound as claimed in claim 3, wherein said compound is in the form of a racemic mixture.

5. A compound as claimed in claim 1, wherein $R^1$ denotes phenyl, naphthyl, thienyl, pyridyl, pyrrolyl, benzyl, methylindolyl, methylthienyl or phenethyl, optionally mono- or polysubstituted with F, Cl, Br, CN, $OCF_3$, $NH_2$, $NO_2$, SH, S—$C_{1-6}$-alkyl, OH, O—$C_{1-6}$-alkyl, $CO_2H$, $CO_2$—$C_{1-6}$-alkyl, $CF_3$ or $C_{1-6}$ alkyl.

6. A compound as claimed in claim 5, wherein $R^1$ denotes phenyl, thienyl, benzyl, methylindolyl, methylthienyl or pyrrolyl, optionally mono- or polysubstituted with Cl, Br, $OCH_3$, $CH_3$, F, $OCF_3$, $CF_3$ or tert.-butyl.

7. A compound as claimed in claim 1, wherein $R^2$ denotes phenyl or thienyl, optionally mono- or polysubstituted with F, Cl, CN, $NO_2$, SH, S—$C_{1-6}$-alkyl, OH, O—$C_{1-6}$-alkyl, $CO_2H$, $CO_2$—$C_{1-6}$-alkyl, $CF_3$, or $C_{1-6}$ alkyl; or denotes a phenyl group linked via a $C_{1-3}$ alkylene group, wherein said linked phenyl group optionally may be mono- or polysubstituted with F, Cl, CN, $NO_2$, SH, S—$C_{1-6}$-alkyl, OH, O—$C_{1-6}$-alkyl, $CO_2H$, $CO_2$—$C_{1-6}$-alkyl, $CF_3$, or $C_{1-6}$ alkyl.

8. A compound as claimed in claim 7, wherein $R^2$ denotes phenyl, phenethyl or thienyl, wherein said phenyl optionally may be monosubstituted with Cl or F.

9. A compound as claimed in claim 1, wherein
$R^3$ and $R^4$ independently denote H or $C_{1-6}$ alkyl, with the proviso that $R^3$ and $R^4$ are not simultaneously H, or
$R^3$ and $R^4$ together denote —$CH_2CH_2OCH_2CH_2$—, or —$(CH_2)_{4-5}$—.

10. A compound as claimed in claim 9, wherein $R^3$ and $R^4$ each denote $CH_3$.

11. A compound as claimed in claim 1, selected from the group consisting of:
43. (4-((3-(4-chlorobenzyl)-1,2,4-oxadiazol-5-yl)methyl)cyclohexyl)-N,N-dimethyl(phenyl)methanamine
44. (4-((3-(4-methoxybenzyl)-1,2,4-oxadiazol-5-yl)methyl)cyclohexyl)-N,N-dimethyl(phenyl)methanamine
45. ((4-chlorophenyl)-{4-[3-(4-chlorophenyl)-[1,2,4]oxadiazol-5-ylmethylene]-cyclohexyl}-methyl)-dimethylamine
46. [{4-[3-(4-chlorophenyl)-[1,2,4]oxadiazol-5-ylmethylene]-cyclohexyl}-(4-fluorophenyl)-methyl]-dimethylamine (more highly polar diastereomer)
47. [{4-[3-(4-chlorophenyl)-[1,2,4]oxadiazol-5-ylmethylene]-cyclohexyl}-(4-fluorophenyl)-methyl]-dimethylamine (more highly nonpolar diastereomer)
48. ({4-[3-(2,3-dichlorophenyl)-[1,2,4]oxadiazol-5-ylmethylene]-cyclohexyl}-phenylmethyl)-dimethylamine (more highly polar diastereomer)
49. ({4-[3-(2,3-dichlorophenyl)-[1,2,4]oxadiazol-5-ylmethylene]-cyclohexyl}-phenylmethyl)-dimethylamine (more highly nonpolar diastereomer)
50. [{4-[3-(2,3-dichlorophenyl)-[1,2,4]oxadiazol-5-ylmethylene]-cyclohexyl}-(3-fluorophenyl)-methyl]-dimethylamine (more highly polar diastereomer)

51. [{4-[3-(2,3-dichlorophenyl)-[1,2,4]oxadiazol-5-ylmethylene]-cyclohexyl}-(3-fluorophenyl)-methyl]-dimethylamine (more highly nonpolar diastereomer)
52. ((4-chlorophenyl)-{4-[3-(2,3-dichlorophenyl)-[1,2,4]oxadiazol-5-ylmethylene]-cyclohexyl}-methyl)-dimethylamine (more highly polar diastereomer)
53. ((4-chlorophenyl)-{4-[3-(2,3-dichlorophenyl)-[1,2,4]oxadiazol-5-ylmethylene]-cyclohexyl}-methyl)-dimethylamine (more highly nonpolar diastereomer)
54. (1-{4-[3-(2,3-dichlorophenyl)-[1,2,4]oxadiazol-5-ylmethylene]-cyclohexyl}-3-phenylpropyl)-dimethylamine
55. [{4-[3-(2,3-dichlorophenyl)-[1,2,4]oxadiazol-5-ylmethylene]-cyclohexyl}-(4-fluorophenyl)-methyl]-dimethylamine (more highly polar diastereomer)
56. [{4-[3-(2,3-dichlorophenyl)-[1,2,4]oxadiazol-5-ylmethylene]-cyclohexyl}-(4-fluorophenyl)-methyl]-dimethylamine (more highly nonpolar diastereomer)
57. dimethyl-(phenyl-{4-[3-(4-trifluoromethoxyphenyl)-[1,2,4]oxadiazol-5-ylmethylene]-cyclohexyl}-methyl)-amine (more highly polar diastereomer)
58. dimethyl-(phenyl-{4-[3-(4-trifluoromethoxyphenyl)-[1,2,4]oxadiazol-5-ylmethylene]-cyclohexyl}-methyl)-amine (more highly nonpolar diastereomer)
59. ((3-fluorophenyl)-{4-[3-(4-trifluoromethoxyphenyl)-[1,2,4]oxadiazol-5-ylmethylene]-cyclohexyl}-methyl)-dimethylamine (more highly polar diastereomer)
60. ((3-fluorophenyl)-{4-[3-(4-trifluoromethoxyphenyl)-[1,2,4]oxadiazol-5-ylmethylene]-cyclohexyl}-methyl)-dimethylamine (more highly nonpolar diastereomer)
61. ((4-chlorophenyl)-{4-[3-(4-trifluoromethoxyphenyl)-[1,2,4]oxadiazol-5-ylmethylene]-cyclohexyl}-methyl)-dimethylamine (more highly polar diastereomer)
62. ((4-chlorophenyl)-{4-[3-(4-trifluoromethoxyphenyl)-[1,2,4]oxadiazol-5-ylmethylene]-cyclohexyl}-methyl)-dimethylamine (more highly nonpolar diastereomer)
63. dimethyl-(3-phenyl-1-{4-[3-(4-trifluoromethoxyphenyl)-[1,2,4]oxadiazol-5-ylmethylene]-cyclohexyl}-propyl)-amine (more highly polar diastereomer)
64. dimethyl-(3-phenyl-1-{4-[3-(4-trifluoromethoxyphenyl)-[1,2,4]oxadiazol-5-ylmethylene]-cyclohexyl}-propyl)-amine (more highly nonpolar diastereomer)
65. ((4-fluorophenyl)-{4-[3-(4-trifluoromethoxyphenyl)-[1,2,4]oxadiazol-5-ylmethylene]-cyclohexyl}-methyl)-dimethylamine (more highly polar diastereomer)
66. ((4-fluorophenyl)-{4-[3-(4-trifluoromethoxyphenyl)-[1,2,4]oxadiazol-5-ylmethylene]-cyclohexyl}-methyl)-dimethylamine (more highly nonpolar diastereomer)
67. dimethyl-(thiophen-2-yl-{4-[3-(4-trifluoromethoxyphenyl)-[1,2,4]oxadiazol-5-ylmethylene]-cyclohexyl}-methyl)-amine (more highly polar diastereomer)
68. dimethyl-(thiophen-2-yl-{4-[3-(4-trifluoromethoxyphenyl)-[1,2,4]oxadiazol-5-ylmethylene]-cyclohexyl}-methyl)-amine (more highly nonpolar diastereomer)
69. dimethyl-{phenyl-[4-(3-phenyl-[1,2,4]oxadiazol-5-ylmethylene)-cyclohexyl]-methyl}-amine (more highly polar diastereomer)
70. dimethyl-{phenyl-[4-(3-phenyl-[1,2,4]oxadiazol-5-ylmethylene)-cyclohexyl]-methyl}-amine (more highly nonpolar diastereomer)
71. {(3-fluorophenyl)-[4-(3-phenyl-[1,2,4]oxadiazol-5-ylmethylene)-cyclohexyl]-methyl}-dimethylamine (more highly polar diastereomer)
72. {(3-fluorophenyl)-[4-(3-phenyl-[1,2,4]oxadiazol-5-ylmethylene)-cyclohexyl]-methyl}-dimethylamine (more highly nonpolar diastereomer)
73. dimethyl-{3-phenyl-1-[4-(3-phenyl-[1,2,4]oxadiazol-5-ylmethylene)-cyclohexyl]-propyl}-amine (more highly polar diastereomer)
74. dimethyl-{3-phenyl-1-[4-(3-phenyl-[1,2,4]oxadiazol-5-ylmethylene)-cyclohexyl]-propyl}-amine (more highly nonpolar diastereomer)
75. {(4-fluorophenyl)-[4-(3-phenyl-[1,2,4]oxadiazol-5-ylmethylene)-cyclohexyl]-methyl}-dimethylamine (more highly polar diastereomer)
76. {(4-fluorophenyl)-[4-(3-phenyl-[1,2,4]oxadiazol-5-ylmethylene)-cyclohexyl]-methyl}-dimethylamine (more highly nonpolar diastereomer)
77. [{4-[3-(2,4-difluorophenyl)-[1,2,4]oxadiazol-5-ylmethylene]-cyclohexyl}-(3-fluorophenyl)-methyl]-dimethylamine (more highly polar diastereomer)
78. [{4-[3-(2,4-difluorophenyl)-[1,2,4]oxadiazol-5-ylmethylene]-cyclohexyl}-(3-fluorophenyl)-methyl]-dimethylamine (more highly nonpolar diastereomer)
79. ({4-[3-(4-methoxybenzyl)-[1,2,4]oxadiazol-5-ylmethylene]-cyclohexyl}-phenylmethyl)-dimethylamine (more highly polar diastereomer)
80. ({4-[3-(4-methoxybenzyl)-[1,2,4]oxadiazol-5-ylmethylene]-cyclohexyl}-phenylmethyl)-dimethylamine (more highly nonpolar diastereomer)
81. ((3-fluorophenyl)-{4-[3-(4-methoxybenzyl)-[1,2,4]oxadiazol-5-ylmethylene]-cyclohexyl}-methyl)-dimethylamine (more highly polar diastereomer)
82. ((3-fluorophenyl)-{4-[3-(4-methoxybenzyl)-[1,2,4]oxadiazol-5-ylmethylene]-cyclohexyl}-methyl)-dimethylamine (more highly nonpolar diastereomer)
83. ((4-chlorophenyl)-{4-[3-(4-methoxybenzyl)-[1,2,4]oxadiazol-5-ylmethylene]-cyclohexyl}-methyl)-dimethylamine (more highly polar diastereomer)
84. ((4-chlorophenyl)-{4-[3-(4-methoxybenzyl)-[1,2,4]oxadiazol-5-ylmethylene]-cyclohexyl}-methyl)-dimethylamine (more highly nonpolar diastereomer)
85. (1-{4-[3-(4-methoxybenzyl)-[1,2,4]oxadiazol-5-ylmethylene]-cyclohexyl}-3-phenylpropyl)-dimethylamine (more highly polar diastereomer)
86. (1-{4-[3-(4-methoxybenzyl)-[1,2,4]oxadiazol-5-ylmethylene]-cyclohexyl}-3-phenylpropyl)-dimethylamine (more highly nonpolar diastereomer)
87. ((4-fluorophenyl)-{4-[3-(4-methoxybenzyl)-[1,2,4]oxadiazol-5-ylmethylene]-cyclohexyl}-methyl)-dimethylamine (more highly polar diastereomer)
88. ((4-fluorophenyl)-{4-[3-(4-methoxybenzyl)-[1,2,4]oxadiazol-5-ylmethylene]-cyclohexyl}-methyl)-dimethylamine (more highly nonpolar diastereomer)
89. ({4-[3-(4-chlorobenzyl)-[1,2,4]oxadiazol-5-ylmethylene]-cyclohexyl}-phenylmethyl)-dimethylamine (more highly polar diastereomer)
90. ({4-[3-(4-chlorobenzyl)-[1,2,4]oxadiazol-5-ylmethylene]-cyclohexyl}-phenylmethyl)-dimethylamine (more highly nonpolar diastereomer)
91. [{4-[3-(4-chlorobenzyl)-[1,2,4]oxadiazol-5-ylmethylene]-cyclohexyl}-(3-fluorophenyl)-methyl]-dimethylamine (more highly polar diastereomer)
92. [{4-[3-(4-chlorobenzyl)-[1,2,4]oxadiazol-5-ylmethylene]-cyclohexyl}-(3-fluorophenyl)-methyl]-dimethylamine (more highly nonpolar diastereomer)
93. [{4-[3-(4-chlorobenzyl)-[1,2,4]oxadiazol-5-ylmethylene]-cyclohexyl}-(4-chlorophenyl)-methyl]-dimethylamine (more highly polar diastereomer)
94. [{4-[3-(4-chlorobenzyl)-[1,2,4]oxadiazol-5-ylmethylene]-cyclohexyl}-(4-chlorophenyl)-methyl]-dimethylamine (more highly nonpolar diastereomer)

95. (1-{4-[3-(4-chlorobenzyl)-[1,2,4]oxadiazol-5-ylmethylene]-cyclohexyl}-3-phenylpropyl)-dimethylamine (more highly polar diastereomer)
96. (1-{4-[3-(4-chlorobenzyl)-[1,2,4]oxadiazol-5-ylmethylene]-cyclohexyl}-3-phenylpropyl)-dimethylamine (more highly nonpolar diastereomer)
97. [{4-[3-(4-chlorobenzyl)-[1,2,4]oxadiazol-5-ylmethylene]-cyclohexyl}-(4-fluorophenyl)-methyl]-dimethylamine (more highly polar diastereomer)
98. [{4-[3-(4-chlorobenzyl)-[1,2,4]oxadiazol-5-ylmethylene]-cyclohexyl}-(4-fluorophenyl)-methyl]-dimethylamine (more highly nonpolar diastereomer)
99. {(3-fluorophenyl)-[4-(3-p-tolyl-[1,2,4]oxadiazol-5-ylmethylene)-cyclohexyl]-methyl}-dimethylamine
100. {(4-chlorophenyl)-[4-(3-p-tolyl-[1,2,4]oxadiazol-5-ylmethylene)-cyclohexyl]-methyl}-dimethylamine
101. {(4-fluorophenyl)-[4-(3-p-tolyl-[1,2,4]oxadiazol-5-ylmethylene)-cyclohexyl]-methyl}-dimethylamine (more highly polar diastereomer)
102. {(4-fluorophenyl)-[4-(3-p-tolyl-[1,2,4]oxadiazol-5-ylmethylene)-cyclohexyl]-methyl}-dimethylamine (more highly nonpolar diastereomer)
103. ({4-[3-(3,4-dimethoxyphenyl)-[1,2,4]oxadiazol-5-ylmethylene]-cyclohexyl}-phenylmethyl)-dimethylamine (more highly polar diastereomer)
104. ({4-[3-(3,4-dimethoxyphenyl)-[1,2,4]oxadiazol-5-ylmethylene]-cyclohexyl}-phenylmethyl)-dimethylamine (more highly nonpolar diastereomer)
105. [{4-[3-(3,4-dimethoxyphenyl)-[1,2,4]oxadiazol-5-ylmethylene]-cyclohexyl}-(3-fluorophenyl)-methyl]-dimethylamine (more highly polar diastereomer)
106. [{4-[3-(3,4-dimethoxyphenyl)-[1,2,4]oxadiazol-5-ylmethylene]-cyclohexyl}-(3-fluorophenyl)-methyl]-dimethylamine (more highly nonpolar diastereomer)
107. ((4-chlorophenyl)-{4-[3-(3,4-dimethoxyphenyl)-[1,2,4]oxadiazol-5-ylmethylene]-cyclohexyl}-methyl)-dimethylamine (more highly polar diastereomer)
108. ((4-chlorophenyl)-{4-[3-(3,4-dimethoxyphenyl)-[1,2,4]oxadiazol-5-ylmethylene]-cyclohexyl}-methyl)-dimethylamine (more highly nonpolar diastereomer)
109. (1-{4-[3-(3,4-dimethoxyphenyl)-[1,2,4]oxadiazol-5-ylmethylene]-cyclohexyl}-3-phenylpropyl)-dimethylamine (more highly polar diastereomer)
110. (1-{4-[3-(3,4-dimethoxyphenyl)-[1,2,4]oxadiazol-5-ylmethylene]-cyclohexyl}-3-phenylpropyl)-dimethylamine (more highly nonpolar diastereomer)
111. [{4-[3-(3,4-dimethoxyphenyl)-[1,2,4]oxadiazol-5-ylmethylene]-cyclohexyl}-(4-fluorophenyl)-methyl]-dimethylamine (more highly polar diastereomer)
112. [{4-[3-(3,4-dimethoxyphenyl)-[1,2,4]oxadiazol-5-ylmethylene]-cyclohexyl}-(4-fluorophenyl)-methyl]-dimethylamine (more highly nonpolar diastereomer)
113. ({4-[3-(3-chlorophenyl)-[1,2,4]oxadiazol-5-ylmethylene]-cyclohexyl}-phenylmethyl)-dimethylamine (more highly polar diastereomer)
114. ({4-[3-(3-chlorophenyl)-[1,2,4]oxadiazol-5-ylmethylene]-cyclohexyl}-phenylmethyl)-dimethylamine (more highly nonpolar diastereomer)
115. [{4-[3-(3-chlorophenyl)-[1,2,4]oxadiazol-5-ylmethylene]-cyclohexyl}-(3-fluorophenyl)-methyl]-dimethylamine (more highly polar diastereomer)
116. [{4-[3-(3-chlorophenyl)-[1,2,4]oxadiazol-5-ylmethylene]-cyclohexyl}-(3-fluorophenyl)-methyl]-dimethylamine (more highly nonpolar diastereomer)
117. ((4-chlorophenyl)-{4-[3-(3-chlorophenyl)-[1,2,4]oxadiazol-5-ylmethylene]-cyclohexyl}-methyl)-dimethylamine (more highly polar diastereomer)
118. ((4-chlorophenyl)-{4-[3-(3-chlorophenyl)-[1,2,4]oxadiazol-5-ylmethylene]-cyclohexyl}-methyl)-dimethylamine (more highly nonpolar diastereomer)
119. (1-{4-[3-(3-chlorophenyl)-[1,2,4]oxadiazol-5-ylmethylene]-cyclohexyl}-3-phenylpropyl)-dimethylamine (more highly polar diastereomer)
120. (1-{4-[3-(3-chlorophenyl)-[1,2,4]oxadiazol-5-ylmethylene]-cyclohexyl}-3-phenylpropyl)-dimethylamine (more highly nonpolar diastereomer)
121. [{4-[3-(3-chlorophenyl)-[1,2,4]oxadiazol-5-ylmethylene]-cyclohexyl}-(4-fluorophenyl)-methyl]-dimethylamine
122. ({4-[3-(4-tert.-butylphenyl)-[1,2,4]oxadiazol-5-ylmethylene]-cyclohexyl}-phenylmethyl)-dimethylamine (more highly polar diastereomer)
123. ({4-[3-(4-tert.-butylphenyl)-[1,2,4]oxadiazol-5-ylmethylene]-cyclohexyl}-phenylmethyl)-dimethylamine (more highly nonpolar diastereomer)
124. [{4-[3-(4-tert.-butylphenyl)-[1,2,4]oxadiazol-5-ylmethylene]-cyclohexyl}-(3-fluorophenyl)-methyl]-dimethylamine (more highly polar diastereomer)
125. [{4-[3-(4-tert.-butylphenyl)-[1,2,4]oxadiazol-5-ylmethylene]-cyclohexyl}-(3-fluorophenyl)-methyl]-dimethylamine (more highly nonpolar diastereomer)
126. [{4-[3-(4-tert.-butylphenyl)-[1,2,4]oxadiazol-5-ylmethylene]-cyclohexyl}-(4-chlorophenyl)-methyl]-dimethylamine (more highly polar diastereomer)
127. [{4-[3-(4-tert.-butylphenyl)-[1,2,4]oxadiazol-5-ylmethylene]-cyclohexyl}-(4-chlorophenyl)-methyl]-dimethylamine (more highly nonpolar diastereomer)
128. (1-{4-[3-(4-tert.-butylphenyl)-[1,2,4]oxadiazol-5-ylmethylene]-cyclohexyl}-3-phenylpropyl)-dimethylamine (more highly polar diastereomer)
129. (1-{4-[3-(4-tert.-butylphenyl)-[1,2,4]oxadiazol-5-ylmethylene]-cyclohexyl}-3-phenylpropyl)-dimethylamine (more highly nonpolar diastereomer)
130. [{4-[3-(4-tert.-butylphenyl)-[1,2,4]oxadiazol-5-ylmethylene]-cyclohexyl}-(4-fluorophenyl)-methyl]-dimethylamine (more highly polar diastereomer)
131. [{4-[3-(4-tert.-butylphenyl)-[1,2,4]oxadiazol-5-ylmethylene]-cyclohexyl}-(4-fluorophenyl)-methyl]-dimethylamine (more highly nonpolar diastereomer)
132. ({4-[3-(4-tert.-butylphenyl)-[1,2,4]oxadiazol-5-ylmethylene]-cyclohexyl}-thiophen-2-yl-methyl)-dimethylamine (more highly polar diastereomer)
133. ({4-[3-(4-tert.-butylphenyl)-[1,2,4]oxadiazol-5-ylmethylene]-cyclohexyl}-thiophen-2-yl-methyl)-dimethylamine (more highly nonpolar diastereomer)
134. dimethyl-{phenyl-[4-(3-m-tolyl-[1,2,4]oxadiazol-5-ylmethylene)-cyclohexyl]-methyl}-amine (more highly polar diastereomer)
135. dimethyl-{phenyl-[4-(3-m-tolyl-[1,2,4]oxadiazol-5-ylmethylene)-cyclohexyl]-methyl}-amine (more highly nonpolar diastereomer)
136. {(3-fluorophenyl)-[4-(3-m-tolyl-[1,2,4]oxadiazol-5-ylmethylene)-cyclohexyl]-methyl}-dimethylamine (more highly polar diastereomer)
137. {(3-fluorophenyl)-[4-(3-m-tolyl-[1,2,4]oxadiazol-5-ylmethylene)-cyclohexyl]-methyl}-dimethylamine (more highly nonpolar diastereomer)
138. {(4-chlorophenyl)-[4-(3-m-tolyl-[1,2,4]oxadiazol-5-ylmethylene)-cyclohexyl]-methyl}-dimethylamine (more highly polar diastereomer)
139. {(4-chlorophenyl)-[4-(3-m-tolyl-[1,2,4]oxadiazol-5-ylmethylene)-cyclohexyl]-methyl}-dimethylamine (more highly nonpolar diastereomer)

140. ((4-fluorophenyl)-{4-[2-(3-phenyl-[1,2,4]oxadiazol-5-yl)-vinyl]-cyclohexyl}-methyl)-dimethylamine
141. [(4-{2-[3-(2,4-difluorophenyl)-[1,2,4]oxadiazol-5-yl]-vinyl}-cyclohexyl)-(4-fluorophenyl)-methyl]-dimethylamine
142. [(4-fluorophenyl)-(4-{2-[3-(4-methoxybenzyl)-[1,2,4]oxadiazol-5-yl]-vinyl}-cyclohexyl)-methyl]-dimethylamine
143. [(4-{2-[3-(4-chlorobenzyl)-[1,2,4]oxadiazol-5-yl]-vinyl}-cyclohexyl)-(4-fluorophenyl)-methyl]-dimethylamine
144. dimethyl-(3-phenyl-1-{4-[2-(3-phenyl-[1,2,4]oxadiazol-5-yl)-vinyl]-cyclohexyl}-propyl)-amine
145. [1-(4-{2-[3-(2,4-difluorophenyl)-[1,2,4]oxadiazol-5-yl]-vinyl}-cyclohexyl)-3-phenylpropyl]-dimethylamine
146. [1-(4-{2-[3-(4-methoxybenzyl)-[1,2,4]oxadiazol-5-yl]-vinyl}-cyclohexyl)-3-phenylpropyl]-dimethylamine
147. [1-(4-{2-[3-(4-chlorobenzyl)-[1,2,4]oxadiazol-5-yl]-vinyl}-cyclohexyl)-3-phenylpropyl]-dimethylamine
148. dimethyl-(phenyl-{4-[2-(3-phenyl-[1,2,4]oxadiazol-5-yl)-vinyl]-cyclohexyl}-methyl)-amine
149. [(4-{2-[3-(4-chlorobenzyl)-[1,2,4]oxadiazol-5-yl]-vinyl}-cyclohexyl)-phenylmethyl]-dimethylamine (more highly polar diastereomer)
150. [(4-{2-[3-(4-chlorobenzyl)-[1,2,4]oxadiazol-5-yl]-vinyl}-cyclohexyl)-phenylmethyl]-dimethylamine (more highly nonpolar diastereomer)
151. [(4-chlorophenyl)-(4-{2-[3-(2,4-difluorophenyl)-[1,2,4]oxadiazol-5-yl]-vinyl}-cyclohexyl)-methyl]-dimethylamine
152. [(4-chlorophenyl)-(4-{2-[3-(4-methoxybenzyl)-[1,2,4]oxadiazol-5-yl]-vinyl}-cyclohexyl)-methyl]-dimethylamine
153. [(4-{2-[3-(4-chlorobenzyl)-[1,2,4]oxadiazol-5-yl]-vinyl}-cyclohexyl)-(4-chlorophenyl)-methyl]-dimethylamine
154. [(4-{2-[3-(4-methoxybenzyl)-[1,2,4]oxadiazol-5-yl]-vinyl}-cyclohexyl)-thiophen-2-yl-methyl]-dimethylamine
155. [(4-{2-[3-(4-chlorobenzyl)-[1,2,4]oxadiazol-5-yl]-vinyl}-cyclohexyl)-thiophen-2-yl-methyl]-dimethylamine
156. ((3-fluorophenyl)-{4-[2-(3-phenyl-[1,2,4]oxadiazol-5-yl)-vinyl]-cyclohexyl}-methyl)-dimethylamine
157. [(3-fluorophenyl)-(4-{2-[3-(4-methoxybenzyl)-[1,2,4]oxadiazol-5-yl]-vinyl}-cyclohexyl)-methyl]-dimethylamine
158. ((4-fluorophenyl)-{4-[2-(3-p-tolyl-[1,2,4]oxadiazol-5-yl)-vinyl]-cyclohexyl}-methyl)-dimethylamine
159. [(4-{2-[3-(3,4-dimethoxyphenyl)-[1,2,4]oxadiazol-5-yl]-vinyl}-cyclohexyl)-(4-fluorophenyl)-methyl]-dimethylamine
160. dimethyl-(3-phenyl-1-{4-[2-(3-p-tolyl-[1,2,4]oxadiazol-5-yl)-vinyl]-cyclohexyl}-propyl)-amine
161. [1-(4-{2-[3-(3,4-dimethoxyphenyl)-[1,2,4]oxadiazol-5-yl]-vinyl}-cyclohexyl)-3-phenylpropyl]-dimethylamine
162. dimethyl-(phenyl-{4-[2-(3-p-tolyl-[1,2,4]oxadiazol-5-yl)-vinyl]-cyclohexyl}-methyl)-amine
163. [(4-{2-[3-(3,4-dimethoxyphenyl)-[1,2,4]oxadiazol-5-yl]-vinyl}-cyclohexyl)-phenylmethyl]-dimethylamine
164. ((4-chlorophenyl)-{4-[2-(3-p-tolyl-[1,2,4]oxadiazol-5-yl)-vinyl]-cyclohexyl}-methyl)-dimethylamine
165. [(4-chlorophenyl)-(4-{2-[3-(3,4-dimethoxyphenyl)-[1,2,4]oxadiazol-5-yl]-vinyl}-cyclohexyl)-methyl]-dimethylamine
166. dimethyl-(thiophen-2-yl-{4-[2-(3-p-tolyl-[1,2,4]oxadiazol-5-yl)-vinyl]-cyclohexyl}-methyl)-amine
167. [(4-{2-[3-(3,4-dimethoxyphenyl)-[1,2,4]oxadiazol-5-yl]-vinyl}-cyclohexyl)-thiophen-2-yl-methyl]-dimethylamine
168. ((3-fluorophenyl)-{4-[2-(3-p-tolyl-[1,2,4]oxadiazol-5-yl)-vinyl]-cyclohexyl}-methyl)-dimethylamine
169. [(4-{2-[3-(3,4-dimethoxyphenyl)-[1,2,4]oxadiazol-5-yl]-vinyl}-cyclohexyl)-(3-fluorophenyl)-methyl]-dimethylamine
170. [(4-{2-[3-(3-chlorophenyl)-[1,2,4]oxadiazol-5-yl]-vinyl}-cyclohexyl)-(4-fluorophenyl)-methyl]-dimethylamine
171. [(4-{2-[3-(4-tert.-butylphenyl)-[1,2,4]oxadiazol-5-yl]-vinyl}-cyclohexyl)-(4-fluorophenyl)-methyl]-dimethylamine
172. [(4-{2-[3-(4-tert.-butylphenyl)-[1,2,4]oxadiazol-5-yl]-vinyl}-cyclohexyl)-(4-fluorophenyl)-methyl]-dimethylamine
173. ((4-fluorophenyl)-{4-[2-(3-m-tolyl-[1,2,4]oxadiazol-5-yl)-vinyl]-cyclohexyl}-methyl)-dimethylamine
174. [1-(4-{2-[3-(3-chlorophenyl)-[1,2,4]oxadiazol-5-yl]-vinyl}-cyclohexyl)-3-phenylpropyl]-dimethylamine
175. [1-(4-{2-[3-(4-tert.-butylphenyl)-[1,2,4]oxadiazol-5-yl]-vinyl}-cyclohexyl)-3-phenylpropyl]-dimethylamine (more highly polar diastereomer)
176. [1-(4-{2-[3-(4-tert.-butylphenyl)-[1,2,4]oxadiazol-5-yl]-vinyl}-cyclohexyl)-3-phenylpropyl]-dimethylamine (more highly nonpolar diastereomer)
177. dimethyl-(3-phenyl-1-{4-[2-(3-m-tolyl-[1,2,4]oxadiazol-5-yl)-vinyl]-cyclohexyl}-propyl)-amine (more highly polar diastereomer)
178. dimethyl-(3-phenyl-1-{4-[2-(3-m-tolyl-[1,2,4]oxadiazol-5-yl)-vinyl]-cyclohexyl}-propyl)-amine (more highly nonpolar diastereomer)
179. [(4-{2-[3-(3-chlorophenyl)-[1,2,4]oxadiazol-5-yl]-vinyl}-cyclohexyl)-phenylmethyl]-dimethylamine
180. [(4-{2-[3-(4-tert.-butylphenyl)-[1,2,4]oxadiazol-5-yl]-vinyl}-cyclohexyl)-phenylmethyl]-dimethylamine (more highly polar diastereomer)
181. [(4-{2-[3-(4-tert.-butylphenyl)-[1,2,4]oxadiazol-5-yl]-vinyl}-cyclohexyl)-phenylmethyl]-dimethylamine (more highly nonpolar diastereomer)
182. dimethyl-(phenyl-{4-[2-(3-m-tolyl-[1,2,4]oxadiazol-5-yl)-vinyl]-cyclohexyl}-methyl)-amine (more highly polar diastereomer)
183. dimethyl-(phenyl-{4-[2-(3-m-tolyl-[1,2,4]oxadiazol-5-yl)-vinyl]-cyclohexyl}-methyl)-amine (more highly nonpolar diastereomer)
184. [(4-{2-[3-(4-chlorophenyl)-[1,2,4]oxadiazol-5-yl]-vinyl}-cyclohexyl)-phenylmethyl]-dimethylamine (more highly polar diastereomer)
185. [(4-{2-[3-(4-chlorophenyl)-[1,2,4]oxadiazol-5-yl]-vinyl}-cyclohexyl)-phenylmethyl]-dimethylamine (more highly nonpolar diastereomer)
186. [(4-chlorophenyl)-(4-{2-[3-(3-chlorophenyl)-[1,2,4]oxadiazol-5-yl]-vinyl}-cyclohexyl)-methyl]-dimethylamine
187. [(4-{2-[3-(4-tert.-butylphenyl)-[1,2,4]oxadiazol-5-yl]-vinyl}-cyclohexyl)-(4-chlorophenyl)-methyl]-dimethylamine (more highly polar diastereomer)
188. [(4-{2-[3-(4-tert.-butylphenyl)-[1,2,4]oxadiazol-5-yl]-vinyl}-cyclohexyl)-(4-chlorophenyl)-methyl]-dimethylamine (more highly nonpolar diastereomer)

189. ((4-chlorophenyl)-{4-[2-(3-m-tolyl-[1,2,4]oxadiazol-5-yl)-vinyl]-cyclohexyl}-methyl)-dimethylamine (more highly polar diastereomer)
190. ((4-chlorophenyl)-{4-[2-(3-m-tolyl-[1,2,4]oxadiazol-5-yl)-vinyl]-cyclohexyl}-methyl)-dimethylamine (more highly nonpolar diastereomer)
191. [(4-chlorophenyl)-(4-{2-[3-(4-chlorophenyl)-[1,2,4]oxadiazol-5-yl]-vinyl}-cyclohexyl)-methyl]-dimethylamine
192. [(4-{2-[3-(3-chlorophenyl)-[1,2,4]oxadiazol-5-yl]-vinyl}-cyclohexyl)-thiophen-2-yl-methyl]-dimethylamine
193. [(4-{2-[3-(4-tert.-butylphenyl)-[1,2,4]oxadiazol-5-yl]-vinyl}-cyclohexyl)-thiophen-2-yl-methyl]-dimethylamine (more highly polar diastereomer)
194. [(4-{2-[3-(4-tert.-butylphenyl)-[1,2,4]oxadiazol-5-yl]-vinyl}-cyclohexyl)-thiophen-2-yl-methyl]-dimethylamine (more highly nonpolar diastereomer)
195. dimethyl-(thiophen-2-yl-{4-[2-(3-m-tolyl-[1,2,4]oxadiazol-5-yl)-vinyl]-cyclohexyl}-methyl)-amine
196. [(4-{2-[3-(4-chlorophenyl)-[1,2,4]oxadiazol-5-yl]-vinyl}-cyclohexyl)-thiophen-2-yl-methyl]-dimethylamine
197. [(4-{2-[3-(3-chlorophenyl)-[1,2,4]oxadiazol-5-yl]-vinyl}-cyclohexyl)-(3-fluorophenyl)-methyl]-dimethylamine
198. [(4-{2-[3-(4-tert.-butylphenyl)-[1,2,4]oxadiazol-5-yl]-vinyl}-cyclohexyl)-(3-fluorophenyl)-methyl]-dimethylamine (more highly polar diastereomer)
199. [(4-{2-[3-(4-tert.-butylphenyl)-[1,2,4]oxadiazol-5-yl]-vinyl}-cyclohexyl)-(3-fluorophenyl)-methyl]-dimethylamine (more highly nonpolar diastereomer)
201. ((3-fluorophenyl)-{4-[2-(3-m-tolyl-[1,2,4]oxadiazol-5-yl)-vinyl]-cyclohexyl}-methyl)-dimethylamine
202. [(4-{2-[3-(4-chlorophenyl)-[1,2,4]oxadiazol-5-yl]-vinyl}-cyclohexyl)-(3-fluorophenyl)-methyl]-dimethylamine
203. [(4-{2-[3-(2,3-dichlorophenyl)-[1,2,4]oxadiazol-5-yl]-vinyl}-cyclohexyl)-(4-fluorophenyl)-methyl]-dimethylamine
204. [(4-fluorophenyl)-(4-{2-[3-(4-trifluoromethoxyphenyl)-[1,2,4]oxadiazol-5-yl]-vinyl}-cyclohexyl)-methyl]-dimethylamine
205. [(4-{2-[3-(3,4-dimethoxybenzyl)-[1,2,4]oxadiazol-5-yl]-vinyl}-cyclohexyl)-(4-fluorophenyl)-methyl]-dimethylamine
206. [(4-{2-[3-(1,5-dimethyl-1H-pyrrol-2-yl)-[1,2,4]oxadiazol-5-yl]-vinyl}-cyclohexyl)-(4-fluorophenyl)-methyl]-dimethylamine
207. [1-(4-{2-[3-(2,3-dichlorophenyl)-[1,2,4]oxadiazol-5-yl]-vinyl}-cyclohexyl)-3-phenylpropyl]-dimethylamine
208. dimethyl-[3-phenyl-1-(4-{2-[3-(4-trifluoromethoxyphenyl)-[1,2,4]oxadiazol-5-yl]-vinyl}-cyclohexyl)-propyl]-amine (more highly polar diastereomer)
209. dimethyl-[3-phenyl-1-(4-{2-[3-(4-trifluoromethoxyphenyl)-[1,2,4]oxadiazol-5-yl]-vinyl}-cyclohexyl)-propyl]-amine (more highly nonpolar diastereomer)
210. [1-(4-{2-[3-(3,4-dimethoxybenzyl)-[1,2,4]oxadiazol-5-yl]-vinyl}-cyclohexyl)-3-phenylpropyl]-dimethylamine (more highly polar diastereomer)
211. [1-(4-{2-[3-(3,4-dimethoxybenzyl)-[1,2,4]oxadiazol-5-yl]-vinyl}-cyclohexyl)-3-phenylpropyl]-dimethylamine (more highly nonpolar diastereomer)
212. [1-(4-{2-[3-(1,5-dimethyl-1H-pyrrol-2-yl)-[1,2,4]oxadiazol-5-yl]-vinyl}-cyclohexyl)-3-phenylpropyl]-dimethylamine
213. [(4-{2-[3-(2,3-dichlorophenyl)-[1,2,4]oxadiazol-5-yl]-vinyl}-cyclohexyl)-phenylmethyl]-dimethylamine
214. [(4-{2-[3-(3,4-dimethoxybenzyl)-[1,2,4]oxadiazol-5-yl]-vinyl}-cyclohexyl)-phenylmethyl]-dimethylamine (more highly polar diastereomer)
215. [(4-{2-[3-(3,4-dimethoxybenzyl)-[1,2,4]oxadiazol-5-yl]-vinyl}-cyclohexyl)-phenylmethyl]-dimethylamine (more highly nonpolar diastereomer)
217. [(4-{2-[3-(1,5-dimethyl-1H-pyrrol-2-yl)-[1,2,4]oxadiazol-5-yl]-vinyl}-cyclohexyl)-phenylmethyl]-dimethylamine
218. [(4-chlorophenyl)-(4-{2-[3-(2,3-dichlorophenyl)-[1,2,4]oxadiazol-5-yl]-vinyl}-cyclohexyl)-methyl]-dimethylamine
219. [(4-chlorophenyl)-(4-{2-[3-(4-trifluoromethoxyphenyl)-[1,2,4]oxadiazol-5-yl]-vinyl}-cyclohexyl)-methyl]-dimethylamine
220. [(4-chlorophenyl)-(4-{2-[3-(3,4-dimethoxybenzyl)-[1,2,4]oxadiazol-5-yl]-vinyl}-cyclohexyl)-methyl]-dimethylamine
221. [(4-chlorophenyl)-(4-{2-[3-(1,5-dimethyl-1H-pyrrol-2-yl)-[1,2,4]oxadiazol-5-yl]-vinyl}-cyclohexyl)-methyl]-dimethylamine
222. [(4-{2-[3-(2,3-dichlorophenyl)-[1,2,4]oxadiazol-5-yl]-vinyl}-cyclohexyl)-thiophen-2-yl-methyl]-dimethylamine
223. dimethyl-[thiophen-2-yl-(4-{2-[3-(4-trifluoromethoxyphenyl)-[1,2,4]oxadiazol-5-yl]-vinyl}-cyclohexyl)-methyl]-amine
224. [(4-{2-[3-(1,5-dimethyl-1H-pyrrol-2-yl)-[1,2,4]oxadiazol-5-yl]-vinyl}-cyclohexyl)-thiophen-2-yl-methyl]-dimethylamine
225. [(4-{2-[3-(2,3-dichlorophenyl)-[1,2,4]oxadiazol-5-yl]-vinyl}-cyclohexyl)-(3-fluorophenyl)-methyl]-dimethylamine
226. [(3-fluorophenyl)-(4-{2-[3-(4-trifluoromethoxyphenyl)-[1,2,4]oxadiazol-5-yl]-vinyl}-cyclohexyl)-methyl]-dimethylamine (more highly polar diastereomer)
227. [(3-fluorophenyl)-(4-{2-[3-(4-trifluoromethoxyphenyl)-[1,2,4]oxadiazol-5-yl]-vinyl}-cyclohexyl)-methyl]-dimethylamine (more highly nonpolar diastereomer)
228. [(4-{2-[3-(3,4-dimethoxybenzyl)-[1,2,4]oxadiazol-5-yl]-vinyl}-cyclohexyl)-(3-fluorophenyl)-methyl]-dimethylamine (more highly polar diastereomer)
229. [(4-{2-[3-(3,4-dimethoxybenzyl)-[1,2,4]oxadiazol-5-yl]-vinyl}-cyclohexyl)-(3-fluorophenyl)-methyl]-dimethylamine (more highly nonpolar diastereomer)
231. [(4-{2-[3-(1,5-dimethyl-1H-pyrrol-2-yl)-[1,2,4]oxadiazol-5-yl]-vinyl}-cyclohexyl)-(3-fluorophenyl)-methyl]-dimethylamine
232. {(3-fluorophenyl)-[4-(3-phenyl-[1,2,4]oxadiazol-5-ylmethyl)-cyclohexyl]-methyl}-dimethylamine
233. {(4-fluorophenyl)-[4-(3-phenyl-[1,2,4]oxadiazol-5-ylmethyl)-cyclohexyl]-methyl}-dimethylamine
234. dimethyl-{phenyl-[4-(3-phenyl-[1,2,4]oxadiazol-5-ylmethyl)-cyclohexyl]-methyl}-amine
235. [{4-[3-(2,4-difluorophenyl)-[1,2,4]oxadiazol-5-ylmethyl]-cyclohexyl}-(3-fluorophenyl)-methyl]-dimethylamine
236. [{4-[3-(2,4-difluorophenyl)-[1,2,4]oxadiazol-5-ylmethyl]-cyclohexyl}-(4-fluorophenyl)-methyl]-dimethylamine
237. ((3-fluorophenyl)-{4-[3-(4-methoxybenzyl)-[1,2,4]oxadiazol-5-ylmethyl]-cyclohexyl}-methyl)-dimethylamine 238. ((4-fluorophenyl)-{4-[3-(4-methoxybenzyl)-[1,2,4]oxadiazol-5-ylmethyl]-cyclohexyl}-methyl)-dimethylamine
239. ({4-[3-(4-methoxybenzyl)-[1,2,4]oxadiazol-5-ylmethyl]-cyclohexyl}-phenylmethyl)-dimethylamine
240. [{4-[3-(4-chlorobenzyl)-[1,2,4]oxadiazol-5-ylmethyl]-cyclohexyl}-(3-fluorophenyl)-methyl]-dimethylamine
241. [{4-[3-(4-chlorobenzyl)-[1,2,4]oxadiazol-5-ylmethyl]-cyclohexyl}-(4-fluorophenyl)-methyl]-dimethylamine
242. [{4-[3-(3-chlorophenyl)-[1,2,4]oxadiazol-5-ylmethyl]-cyclohexyl}-(4-fluorophenyl)-methyl]-dimethylamine
243. ({4-[3-(3-chlorophenyl)-[1,2,4]oxadiazol-5-ylmethyl]-cyclohexyl}-phenylmethyl)-dimethylamine
244. [{4-[3-(2,3-dichlorophenyl)-[1,2,4]oxadiazol-5-ylmethyl]-cyclohexyl}-(3-fluorophenyl)-methyl]-dimethylamine
245. [{4-[3-(2,3-dichlorophenyl)-[1,2,4]oxadiazol-5-ylmethyl]-cyclohexyl}-(4-fluorophenyl)-methyl]-dimethylamine
246. ({4-[3-(2,3-dichlorophenyl)-[1,2,4]oxadiazol-5-ylmethyl]-cyclohexyl}-phenylmethyl)-dimethylamine
247. {(3-fluorophenyl)-[4-(3-p-tolyl-[1,2,4]oxadiazol-5-ylmethyl)-cyclohexyl]-methyl}-dimethylamine
248. {(4-fluorophenyl)-[4-(3-p-tolyl-[1,2,4]oxadiazol-5-ylmethyl)-cyclohexyl]-methyl}-dimethylamine
249. dimethyl-{phenyl-[4-(3-p-tolyl-[1,2,4]oxadiazol-5-ylmethyl)-cyclohexyl]-methyl}-amine
250. [{4-[3-(3,4-dimethoxyphenyl)-[1,2,4]oxadiazol-5-ylmethyl]-cyclohexyl}-(3-fluorophenyl)-methyl]-dimethylamine
251. [{4-[3-(3,4-dimethoxyphenyl)-[1,2,4]oxadiazol-5-ylmethyl]-cyclohexyl}-(4-fluorophenyl)-methyl]-dimethylamine
252. ({4-[3-(3,4-dimethoxyphenyl)-[1,2,4]oxadiazol-5-ylmethyl]-cyclohexyl}-phenylmethyl)-dimethylamine
253. [{4-[3-(4-tert.-butylphenyl)-[1,2,4]oxadiazol-5-ylmethyl]-cyclohexyl}-(3-fluorophenyl)-methyl]-dimethylamine
254. [{4-[3-(4-tert.butylphenyl)-[1,2,4]oxadiazol-5-ylmethyl]-cyclohexyl}-(4-fluorophenyl)-methyl]-dimethylamine
255. ({4-[3-(4-tert.-butylphenyl)-[1,2,4]oxadiazol-5-ylmethyl]-cyclohexyl}-phenylmethyl)-dimethylamine
256. {(3-fluorophenyl)-[4-(3-m-tolyl-[1,2,4]oxadiazol-5-ylmethyl)-cyclohexyl]-methyl}-dimethylamine
257. {(4-fluorophenyl)-[4-(3-m-tolyl-[1,2,4]oxadiazol-5-ylmethyl)-cyclohexyl]-methyl}-dimethylamine
258. dimethyl-{phenyl-[4-(3-m-tolyl-[1,2,4]oxadiazol-5-ylmethyl)-cyclohexyl]-methyl}-amine
259. [{4-[3-(4-chlorophenyl)-[1,2,4]oxadiazol-5-ylmethyl]-cyclohexyl}-(3-fluorophenyl)-methyl]-dimethylamine
260. ({4-[3-(4-chlorophenyl)-[1,2,4]oxadiazol-5-ylmethyl]-cyclohexyl}-phenylmethyl)-dimethylamine
261. ((3-fluorophenyl)-{4-[3-(4-trifluoromethoxyphenyl)-[1,2,4]oxadiazol-5-ylmethyl-cyclohexyl}-methyl)-dimethylamine
262. ((4-fluorophenyl)-{4-[3-(4-trifluoromethoxyphenyl)-[1,2,4]oxadiazol-5-ylmethyl-cyclohexyl}-methyl)-dimethylamine
263. dimethyl-(phenyl-{4-[3-(4-trifluoromethoxyphenyl)-[1,2,4]oxadiazol-5-ylmethyl-cyclohexyl}-methyl)-amine
264. ((4-fluorophenyl)-{4-[2-(3-phenyl-[1,2,4]oxadiazol-5-yl)-ethyl]-cyclohexyl}-methyl)-dimethylamine
265. dimethyl-(phenyl-{4-[2-(3-phenyl-[1,2,4]oxadiazol-5-yl)-ethyl]-cyclohexyl}-methyl)-amine
266. dimethyl-(3-phenyl-1-{4-[2-(3-phenyl-[1,2,4]oxadiazol-5-yl)-ethyl]-cyclohexyl}-propyl)-amine
267. ((3-fluorophenyl)-{4-[2-(3-phenyl-[1,2,4]oxadiazol-5-yl)-ethyl]-cyclohexyl}-methyl)-dimethylamine
268. [(4-fluorophenyl)-(4-{2-[3-(4-methoxybenzyl)-[1,2,4]oxadiazol-5-yl]-ethyl}-cyclohexyl)-methyl]-dimethylamine
269. [(4-{2-[3-(4-methoxybenzyl)-[1,2,4]oxadiazol-5-yl]-ethyl}-cyclohexyl)-phenylmethyl]-dimethylamine
270. [1-(4-{2-[3-(4-methoxybenzyl)-[1,2,4]oxadiazol-5-yl]-ethyl}-cyclohexyl)-3-phenylpropyl]-dimethylamine
271. [(3-fluorophenyl)-(4-{2-[3-(4-methoxybenzyl)-[1,2,4]oxadiazol-5-yl]-ethyl}-cyclohexyl)-methyl]-dimethylamine
272. [(4-{2-[3-(4-chlorobenzyl)-[1,2,4]oxadiazol-5-yl]-ethyl}-cyclohexyl)-(4-fluorophenyl)-methyl]-dimethylamine
273. [(4-{2-[3-(4-chlorobenzyl)-[1,2,4]oxadiazol-5-yl]-ethyl}-cyclohexyl)-phenylmethyl]-dimethylamine
274. [1-(4-{2-[3-(4-chlorobenzyl)-[1,2,4]oxadiazol-5-yl]-ethyl}-cyclohexyl)-3-phenylpropyl]-dimethylamine
275. [(4-{2-[3-(4-chlorobenzyl)-[1,2,4]oxadiazol-5-yl]-ethyl}-cyclohexyl)-(3-fluorophenyl)-methyl]-dimethylamine
276. [(4-{2-[3-(3-chlorophenyl)-[1,2,4]oxadiazol-5-yl]-ethyl}-cyclohexyl)-(4-fluorophenyl)-methyl]-dimethylamine
277. [(4-{2-[3-(3-chlorophenyl)-[1,2,4]oxadiazol-5-yl]-ethyl}-cyclohexyl)-phenylmethyl]-dimethylamine
278. [1-(4-{2-[3-(3-chlorophenyl)-[1,2,4]oxadiazol-5-yl]-ethyl}-cyclohexyl)-3-phenylpropyl]-dimethylamine
279. [(4-{2-[3-(3-chlorophenyl)-[1,2,4]oxadiazol-5-yl]-ethyl}-cyclohexyl)-(3-fluorophenyl)-methyl]-dimethylamine
280. [(4-{2-[3-(2,4-difluorophenyl)-[1,2,4]oxadiazol-5-yl]-ethyl}-cyclohexyl)-(4-fluorophenyl)-methyl]-dimethylamine
281. [(4-{2-[3-(2,4-difluorophenyl)-[1,2,4]oxadiazol-5-yl]-ethyl}-cyclohexyl)-phenylmethyl]-dimethylamine
282. [(4-{2-[3-(2,4-difluorophenyl)-[1,2,4]oxadiazol-5-yl]-ethyl}-cyclohexyl)-(3-fluorophenyl)-methyl]-dimethylamine
283. [(4-{2-[3-(3,4-dimethoxyphenyl)-[1,2,4]oxadiazol-5-yl]-ethyl}-cyclohexyl)-(4-fluorophenyl)-methyl]-dimethylamine
284. [(4-{2-[3-(3,4-dimethoxyphenyl)-[1,2,4]oxadiazol-5-yl]-ethyl}-cyclohexyl)-phenylmethyl]-dimethylamine
285. [1-(4-{2-[3-(3,4-dimethoxyphenyl)-[1,2,4]oxadiazol-5-yl]-ethyl}-cyclohexyl)-3-phenylpropyl]-dimethylamine
286. [(4-{2-[3-(3,4-dimethoxyphenyl)-[1,2,4]oxadiazol-5-yl]-ethyl}-cyclohexyl)-(3-fluorophenyl)-methyl]-dimethylamine
287. ((4-fluorophenyl)-{4-[2-(3-p-tolyl-[1,2,4]oxadiazol-5-yl)-ethyl]-cyclohexyl}-methyl)-dimethylamine
288. dimethyl-(phenyl-{4-[2-(3-p-tolyl-[1,2,4]oxadiazol-5-yl)-ethyl]-cyclohexyl}-methyl)-amine
289. dimethyl-(3-phenyl-1-{4-[2-(3-p-tolyl-[1,2,4]oxadiazol-5-yl)-ethyl]-cyclohexyl}-propyl)-amine
290. ((3-fluorophenyl)-{4-[2-(3-p-tolyl-[1,2,4]oxadiazol-5-yl)-ethyl]-cyclohexyl}-methyl)-dimethylamine 291. [(4-{2-[3-(4-tert.-butylphenyl)-[1,2,4]oxadiazol-5-yl]-ethyl}-cyclohexyl)-(4-fluorophenyl)-methyl]-dimethylamine
292. [(4-{2-[3-(4-tert.-butylphenyl)-[1,2,4]oxadiazol-5-yl]-ethyl}-cyclohexyl)-phenylmethyl]-dimethylamine
293. [1-(4-{2-[3-(4-tert.-butylphenyl)-[1,2,4]oxadiazol-5-yl]-ethyl}-cyclohexyl)-3-phenylpropyl]-dimethylamine
294. [(4-{2-[3-(4-tert.-butylphenyl)-[1,2,4]oxadiazol-5-yl]-ethyl}-cyclohexyl)-(3-fluorophenyl)-methyl]-dimethylamine
295. ((4-fluorophenyl)-{4-[2-(3-m-tolyl-[1,2,4]oxadiazol-5-yl)-ethyl]-cyclohexyl}-methyl)-dimethylamine
296. dimethyl-(phenyl-{4-[2-(3-m-tolyl-[1,2,4]oxadiazol-5-yl)-ethyl]-cyclohexyl}-methyl)-amine
297. dimethyl-(3-phenyl-1-{4-[2-(3-m-tolyl-[1,2,4]oxadiazol-5-yl)-ethyl]-cyclohexyl}-propyl)-amine
298. ((3-fluorophenyl)-{4-[2-(3-m-tolyl-[1,2,4]oxadiazol-5-yl)-ethyl]-cyclohexyl}-methyl)-dimethylamine
299. [(4-{2-[3-(4-chlorophenyl)-[1,2,4]oxadiazol-5-yl]-ethyl}-cyclohexyl)-(4-fluorophenyl)-methyl]-dimethylamine
300. [(4-{2-[3-(4-chlorophenyl)-[1,2,4]oxadiazol-5-yl]-ethyl}-cyclohexyl)-phenylmethyl]-dimethylamine
301. [1-(4-{2-[3-(4-chlorophenyl)-[1,2,4]oxadiazol-5-yl]-ethyl}-cyclohexyl)-3-phenylpropyl]-dimethylamine
302. [(4-{2-[3-(4-chlorophenyl)-[1,2,4]oxadiazol-5-yl]-ethyl}-cyclohexyl)-(3-fluorophenyl)-methyl]-dimethylamine
303. [(4-{2-[3-(2,3-dichlorophenyl)-[1,2,4]oxadiazol-5-yl]-ethyl}-cyclohexyl)-(4-fluorophenyl)-methyl]-dimethylamine
304. [(4-{2-[3-(2,3-dichlorophenyl)-[1,2,4]oxadiazol-5-yl]-ethyl}-cyclohexyl)-phenylmethyl]-dimethylamine
305. [1-(4-{2-[3-(2,3-dichlorophenyl)-[1,2,4]oxadiazol-5-yl]-ethyl}-cyclohexyl)-3-phenylpropyl]-dimethylamine
306. [(4-{2-[3-(2,3-dichlorophenyl)-[1,2,4]oxadiazol-5-yl]-ethyl}-cyclohexyl)-(3-fluorophenyl)-methyl]-dimethylamine
307. [(4-fluorophenyl)-(4-{2-[3-(4-trifluoromethoxyphenyl)-[1,2,4]oxadiazol-5-yl]-ethyl}-cyclohexyl)-methyl]-dimethylamine
308. dimethyl-[phenyl-(4-{2-[3-(4-trifluoromethoxyphenyl)-[1,2,4]oxadiazol-5-yl]-ethyl}-cyclohexyl)-methyl]-amine
309. dimethyl-[3-phenyl-1-(4-{2-[3-(4-trifluoromethoxyphenyl)-[1,2,4]oxadiazol-5-yl]-ethyl}-cyclohexyl)-propyl]-amine
310. [(3-fluorophenyl)-(4-{2-[3-(4-trifluoromethoxyphenyl)-[1,2,4]oxadiazol-5-yl]-ethyl}-cyclohexyl)-methyl]-dimethylamine
311. (4-((3-(4-fluorobenzyl)-1,2,4-oxadiazol-5-yl)methyl)cyclohexyl)(4-fluorophenyl)-N,N-dimethylmethanamine
312. (4-((3-(4-fluorobenzyl)-1,2,4-oxadiazol-5-yl)methyl)cyclohexyl)-N,N-dimethyl(phenyl)methanamine
313. (4-((3-(3-chlorobenzyl)-1,2,4-oxadiazol-5-yl)methyl)cyclohexyl)(3-fluorophenyl)-N,N-dimethylmethanamine
314. (4-((3-(3-chlorobenzyl)-1,2,4-oxadiazol-5-yl)methyl)cyclohexyl)(4-fluorophenyl)-N,N-dimethylmethanamine
315. (4-((3-(3-chlorobenzyl)-1,2,4-oxadiazol-5-yl)methyl)cyclohexyl)-N,N-dimethyl(phenyl)methanamine
316. (4-((3-(3-bromophenyl)-1,2,4-oxadiazol-5-yl)methyl)cyclohexyl)(3-fluorophenyl)-N,N-dimethylmethanamine
317. (4-((3-(3-bromophenyl)-1,2,4-oxadiazol-5-yl)methyl)cyclohexyl)(4-fluorophenyl)-N,N-dimethylmethanamine
318. (4-((3-(3-bromophenyl)-1,2,4-oxadiazol-5-yl)methyl)cyclohexyl)-N,N-dimethyl(phenyl)methanamine
319. (4-((3-(4-bromobenzyl)-1,2,4-oxadiazol-5-yl)methyl)cyclohexyl)(3-fluorophenyl)-N,N-dimethylmethanamine
320. (4-((3-(4-bromobenzyl)-1,2,4-oxadiazol-5-yl)methyl)cyclohexyl)(4-fluorophenyl)-N,N-dimethylmethanamine
321. (4-((3-(4-bromobenzyl)-1,2,4-oxadiazol-5-yl)methyl)cyclohexyl)-N,N-dimethyl(phenyl)methanamine
322. (3-fluorophenyl)-N,N-dimethyl(4-((3-(thiophen-2-ylmethyl)-1,2,4-oxadiazol-5-yl)methyl)cyclohexyl)methanamine
323. (4-fluorophenyl)-N,N-dimethyl(4-((3-(thiophen-2-ylmethyl)-1,2,4-oxadiazol-5-yl)methyl)cyclohexyl)methanamine
324. N,N-dimethyl(phenyl)(4-((3-(thiophen-2-ylmethyl)-1,2,4-oxadiazol-5-yl)methyl)cyclohexyl)methanamine
325. (4-((3-benzyl-1,2,4-oxadiazol-5-yl)methyl)cyclohexyl)(3-fluorophenyl)-N,N-dimethylmethanamine
326. (4-((3-benzyl-1,2,4-oxadiazol-5-yl)methyl)cyclohexyl)(4-fluorophenyl)-N,N-dimethylmethanamine
327. (4-((3-benzyl-1,2,4-oxadiazol-5-yl)methyl)cyclohexyl)-N,N-dimethyl(phenyl)methanamine
328. (3-fluorophenyl)-N,N-dimethyl(4-((3-phenethyl-1,2,4-oxadiazol-5-yl)methyl)cyclohexyl)methanamine
329. (4-fluorophenyl)-N,N-dimethyl(4-((3-phenethyl-1,2,4-oxadiazol-5-yl)methyl)cyclohexyl)methanamine
330. N,N-dimethyl(4-((3-phenethyl-1,2,4-oxadiazol-5-yl)methyl)cyclohexyl)(phenyl)methanamine
331. (4-((3-((1H-indol-3-yl)methyl)-1,2,4-oxadiazol-5-yl)methyl)cyclohexyl)(3-fluorophenyl)-N,N-dimethylmethanamine.

12. A pharmaceutical composition comprising a compound as claimed in claim 1, and at least one pharmaceutical carrier or pharmaceutical auxiliary substance.

13. A method of producing a compound as claimed in claim 1, said method comprising reacting an amide oxime compound corresponding to formula D in a reaction medium in the presence of a base with a saturated or unsaturated ester corresponding to formula A to yield a compound corresponding to formula I according to the following equation:

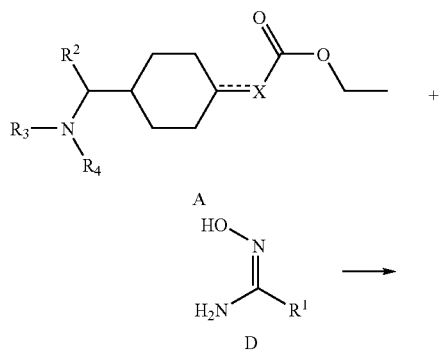

-continued

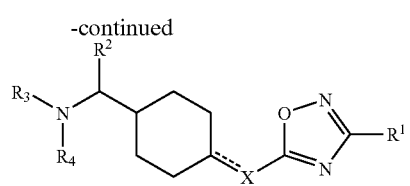

wherein R¹ through R⁴ and X have the meanings given in claim 1.

14. A method as claimed in claim 13, wherein the reaction is carried out in the presence of NaH as a base.

15. A method of treating a condition selected from the group consisting of pain, depression, urinary incontinence, diarrhea, pruritus, alcohol and drug abuse, drug dependency, lethargy and anxiety in a subject in need thereof, said method comprising administering to said subject a pharmaceutically effective amount of a compound as claimed in claim 1.

16. A method of treating pain in a subject in need thereof, said method comprising administering to said subject a pharmaceutically effective amount of a compound as claimed in claim 1.

17. A method as claimed in claim 16, wherein said pain is selected from the group consisting of acute pain, neuropathic pain and chronic pain.

* * * * *